US007842479B2

(12) United States Patent
Bayles et al.

(10) Patent No.: US 7,842,479 B2
(45) Date of Patent: Nov. 30, 2010

(54) METHODS FOR ALTERING ACETIC ACID PRODUCTION AND ENHANCING CELL DEATH IN BACTERIA

(75) Inventors: Kenneth W. Bayles, Omaha, NE (US); Toni G. Patton, Omaha, NE (US); Kelly C. Rice, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 130 days.

(21) Appl. No.: 11/597,013

(22) PCT Filed: May 20, 2005

(86) PCT No.: PCT/US2005/017604

§ 371 (c)(1),
(2), (4) Date: Nov. 17, 2006

(87) PCT Pub. No.: WO2006/065272

PCT Pub. Date: Jun. 22, 2006

(65) Prior Publication Data

US 2007/0231841 A1     Oct. 4, 2007

Related U.S. Application Data

(60) Provisional application No. 60/573,431, filed on May 21, 2004, provisional application No. 60/642,039, filed on Jan. 6, 2005.

(51) Int. Cl.
| | |
|---|---|
| C12P 21/06 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl. ............ 435/69.1; 435/183; 435/252.3; 435/320.1; 536/23.2

(58) Field of Classification Search .............. None
See application file for complete search history.

(56) References Cited

U.S. PATENT DOCUMENTS

| | | | |
|---|---|---|---|
| 5,139,938 | A | 8/1992 | Shimizu et al. |
| 5,733,723 | A | 3/1998 | van Eekelen et al. |
| 6,107,093 | A | 8/2000 | Ingram et al. |
| 6,150,133 | A | 11/2000 | Mead et al. |
| 6,348,582 | B1 | 2/2002 | Black et al. |
| 6,428,981 | B1 | 8/2002 | Joergensen et al. |
| 6,458,557 | B1 | 10/2002 | Miller et al. |
| 6,593,114 | B1 | 7/2003 | Kunsch et al. |
| 6,630,328 | B2 | 10/2003 | Quax et al. |

FOREIGN PATENT DOCUMENTS

| | | |
|---|---|---|
| WO | WO 98/58049 | 12/1998 |
| WO | WO 02/059148 | 8/2002 |
| WO | WO 02/094868 | 11/2002 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Airistidou et al., "Metabolic engineering of *Escherichia coli* to enhance recombinant protein production through acetate reduction," *Biotechnology Progress* 11(4) 475-478 (1995) (Abstract Only).
Arbige et al., "Fermentation of *Bacillus*," in *Bacillus subtilis and Other Gram-Positive Bacteria*, Hoch et al. (eds.), American Society for Microbiology, Washington, D.C. (1993), pp. 871-873.
Bayles, "Are the molecular stategies that control apoptosis conserved in bacteria?" *Trends in Microbiology* 11(7): 306-311 (2003).
Farmer and Liao, "Reduction of Aerobic Acetate Production by *Escherichia coli*," *Applied and Environmental Microbiology* 63(8): 3205-3210 (1997).
Ferrari et al., "Commercial Production of Extracellular Enzymes," in *Bacillus subtilis and Other Gram-Positive Bacteria*, Hoch et al. (eds.), American Society for Microbiology, Washington, D.C. (1993), pp. 917-931.
Fujimoto et al., "Analysis of Genetic Elements Controlling *Staphylococcus aureus lrgAB* Expression: Potential Role of DNA Topology in SarA Regulation," *Journal of Bacteriology* 182(17): 4822-4828 (2000).
Juty et al., "The *Klebsiella pneumoniae* cytomchrome *bd*' terminal oxidase complex and its role in microaerobic nitrogen fixation," *Microbiology* 143: 2673-2683 (1997).
March et al. "Expression of an Anaplerotic Enzyme, Pyruvate Carboxylase, Improves Recombinant Protein Production in *Escherichia coli*," *Applied and Environmental Microbiology* 68(11): 5620-5624 (2002).
Neubauer et al., "Metabolic load of recombinant protein production: inhibition of cellular capacities for glucose uptake and respiration after induction of a heterologous gene in *Escherichia coli*," *Biotechnology and Bioengineering* 83(1): 53-64 (2003) (Abstract Only).
Parry et al., *A Colour Atlas of Bacillus Species*, Wolfe Medical Publications Ltd (1983), pp. 239-244.
Patton et al. "The *Staphylococcus aureus cidC* gene encodes a pyruvate oxides that affects acetate metabolism and cell death in stationary phase," Abstract of presentation to American Society of Microbiology, 2004 Annual Meeting, publicly available at least as early as May 23, 2004.

(Continued)

*Primary Examiner*—Christian L Fronda
(74) *Attorney, Agent, or Firm*—Klarquist Sparkman, LLP.

(57) ABSTRACT

Methods of increasing cultured cell growth yields and/or protein production from bacterial cell cultures are provided. More particularly, mutant bacterial cells having an alteration in the expression or activity of the cidABC operon, a gene therein, or a homolog or a regulator thereof, and methods for reducing acetic acid/acetate production in cultures are provided, as are methods for increasing cultured cell growth yields and/or protein production employing such cells. Methods for enhancing bacterial cell death and methods for identifying agents that increase the susceptibility of bacteria to cell death are also provided.

15 Claims, 24 Drawing Sheets

OTHER PUBLICATIONS

Patton et al. "The *Staphylococcus aureus cidC* gene encodes a pyruvate oxides that affects acetate metabolism and cell death in stationary phase," *Molecular Microbiology* 56(6): 1664-1674 (2005).

Patton et al., "The role of proton motive force in expression of the *Staphylococcus aureus cid* and *lrg* operons," *Molecular Microbiology* 59(5): 1395-1404 (2006).

Perkins and Pero, "Vitamin Biosythesis," in *Bacillus subtilis and Its Closest Relatives: from Genes to Cells*, Sonenshein et al. (eds.), pp. 271-281, ASM Press, Washington, D.C., (2002).

Rice and Bayles, "Death's toolbox: examining the molecular components of bacterial programmed cell death," *Molecular Microbiology* 59(3): 729-738 (2003).

Rice et al., "Acetic Acid Induces Expression of the *Staphylococcus aureaus cidABC* and *lrgAB* Murein Hydrolase Regulator Operons," *Journal of Bacteriology* 187(3): 813-821 (2005).

Rice et al., "The *Staphylococcus aureus cidAB* Operon: Evaluation of Its Role in Regulation of Murein Hydrolase Activity and Penicillin Tolerance," *Journal of Bacteriology* 185(8): 2635-2643 (2003).

Rice et al., "Transcription of the *Staphylococcus aureus cid* and *lrg* Murein Hydrolase Regulators Is Affected by Sigma Factor B," *Journal of Bacteriology* 186(10): 3029-3037 (2004).

Somerville et al., "Correlation of Acetate Catabolism and Growth Yield in *Staphylococcus aureaus*: Implications for Host-Pathogen Interactions," *Infection and Immunity* 71(8): 4724-4732 (2003).

Tseng et al., "Effect of Microaerophilic Cell Growth Conditions on Expression of the Aerobic (*cyoABCDE* and *cydAB*) and Anaerobic (*narGHJI*, *frdABCD*, and *dmsABC*) Respiratory Pathway Genes in *Escherichia coli*," *Journal of Bacteriology* 178(4): 1094-1098 (1996).

Wang et al., "Analysis of Codon Usage Patterns of Bacterial Genomes Using the Self-Organizing Map," *Molecular Biology and Evolution* 18(5): 792-800 (2001).

Yang et al., "A LysR-Type Regulator, CidR, Is Required for Induction of the *Staphylococcus aureaus cidABC* Operon," Abstract of presentation to American Society of Microbiology, 2004 Annual Meeting, publicly available at least as early as May 23, 2004.

Yang et al., "A LysR-Type Regulator, CidR, Is Required for Induction of the *Staphylococcus aureaus cidABC* Operon," *Journal of Bacteriology* 187(17): 5893-5900 (2005).

Yang et al., "Characterization of the *Staphylococcus aureus* CidR regulon: elucidation of a novel role for acetoin metabolism in cell death and lysis," *Molecular Microbiology* 60(2): 458-468 (2006).

Yang et al., "Genetic and metabolic engineering," *Electronic Journal of Biotechnology* 1(3): 8 pages (Dec. 15, 1998).

Zamboni and Sauer, "Knockout of the high-coupling cytochrome $aa3$ oxidase reduces TCA cycle fluxes in *Bacillus subtilis*," *FEMS Microbiology Letters* 226: 121-126 (2003).

Zuber et al., "Peptide Antibiotics," in *Bacillus subtilis and Other Gram-Positive Bacteria*, Hoch et al. (eds.), American Society for Microbiology, Washington, D.C. (1993), pp. 897-900.

Accession No. AY581892, NCBI DNA Sequence: "*Staphylococcus aureus* CidR (cidR), CidA (cidA), CidB (cidB), and CidC (cidC) genes, complete cds," (Apr. 19, 2004) (4 pages).

\* cited by examiner

NZY

NZY w/ 35mM glucose

NZY w/ acetic acid

A

NZY

B

NZY w/ 35mM glucose

C

NZY w/ acetic acid

NZY w/ 35mM glucose

A

B

SEQUENCE LISTING

<160> NUMBER OF SEQ ID NOS: 52

<210> SEQ ID NO 1
<211> LENGTH: 1740
<212> TYPE: DNA
<213> ORGANISM: Staphylococcus aureus

<400> SEQUENCE: 1

```
atggcaaaaa taaaagcaaa tgaagcatta gttaaagcat tacaagcatg ggatatagat      60
cacttgtatg gtattccagg agactcaatc gacgcagtag tcgatagttt acgtacagtg     120
agagatcaat ttaaatttta tcatgtacgt catgaagaag tagcaagctt agcggctgct     180
ggttacacaa aattaactgg taaaatcggt gtggcattaa gtatcggtgg ccctggttta     240
attcatttat taaatggtat gtatgatgcc aaaatggata atgtaccgca attaatatta     300
tctggacaaa cgaatagtac agcacttgga acgaaagcat tccaagaaac aaatttacaa     360
aaattatgtg aagatgtagc cgtttataat caccaaattg aaaaaggtga caatgtgttt     420
gaaatcgtta acgaagcaat tcgtacggca tatgaacaaa aaggtgtagc tgttgttatt     480
tgtcctaacg acttattaac tgaaaaaatt aaagatacaa cgaataaacc agtagataca     540
tcaagaccaa cagtagtatc accaaaatat aaagacatca aaaaagcggt taaactaatt     600
aataaaagta aaaagcctgt catgttaatt ggtgtaggtg cgaaacatgc gaaagatgag     660
ctacgtgaat ttattgaaat ggctaaaatt cctgtcattc attcattacc agctaaaaca     720
atcttgccgg atgatcatcc atatagtatc ggtaacttag gtaaaatcgg taccaaaaca     780
tcttatcaaa caatgcagga agcggattta ttaattatgt tggtacaaa ctatccatat     840 gtggattact tacctaagaa aaatattaaa gccattcaaa ttgacacaaa tcctaaaaat     900
atcggacatc gtttcaatat taatgtagga attgttggag atagtaaaat tgcgttgcat     960
cagttaactg aaaatattaa acatgttgct gaaagaccat tcttaaacaa aacgttagaa    1020
cgtaaagcgg tttgggataa atggatggaa caagataaaa ataataatag taaaccatta    1080
cgtccagaac gattaatggc atcaatcaat aaatttatta aagatgatgc agtgatttca    1140
gcagatgtag gtacagcaac agtttggtca actcgatact taaaccttgg tgtaaataac    1200
aagttcatca tttcaagttg gttaggtaca atgggttgcg gtcttccagg tgcaattgca    1260
tcaaaaattg catatccaaa tagacaagcc atcgcaattg ctggtgacgg tgcattccaa    1320
atggtaatgc aagacttcgc tacagcagta caatatgatt taccttaac tgtatttgta    1380 cttaataaca aacagttagc atttattaaa tatgaacaac aagcagctgg tgaattagaa    1440
tatgcagttg atttttctga tatggatcat gcaaaatttg ctgaggcagc aggtggtaaa    1500
ggttatacaa ttaagagtgc tagcgaagta gatgctatag tcgaagaggc attagcacaa    1560
```

```
gatgtaccaa cgattgtaga tgtatatgtt gatcctaatg ctgcgccatt accaggtaaa    1620
attgtaaatg aagaagcgct tggttatggt aagtgggcat ttagatcaat tactgaagat    1680
aaacatttag atttagatca aattccacca atttcagtgg cagcaaaacg tttcttataa    1740
```

<210> SEQ ID NO 2
<211> LENGTH: 579
<212> TYPE: PRT
<213> ORGANISM: Staphylococcus aureus

<400> SEQUENCE: 2

```
Met Ala Lys Ile Lys Ala Asn Glu Ala Leu Val Lys Ala Leu Gln Ala
1               5                   10                  15

Trp Asp Ile Asp His Leu Tyr Gly Ile Pro Gly Asp Ser Ile Asp Ala
            20                  25                  30

Val Val Asp Ser Leu Arg Thr Val Arg Asp Gln Phe Lys Phe Tyr His
        35                  40                  45

Val Arg His Glu Glu Val Ala Ser Leu Ala Ala Ala Gly Tyr Thr Lys
    50                  55                  60

Leu Thr Gly Lys Ile Gly Val Ala Leu Ser Ile Gly Gly Pro Gly Leu
65                  70                  75                  80

Ile His Leu Leu Asn Gly Met Tyr Asp Ala Lys Met Asp Asn Val Pro
                85                  90                  95

Gln Leu Ile Leu Ser Gly Gln Thr Asn Ser Thr Ala Leu Gly Thr Lys
            100                 105                 110

Ala Phe Gln Glu Thr Asn Leu Gln Lys Leu Cys Glu Asp Val Ala Val
        115                 120                 125

Tyr Asn His Gln Ile Glu Lys Gly Asp Asn Val Phe Glu Ile Val Asn
    130                 135                 140

Glu Ala Ile Arg Thr Ala Tyr Glu Gln Lys Gly Val Ala Val Val Ile
145                 150                 155                 160

Cys Pro Asn Asp Leu Leu Thr Glu Lys Ile Lys Asp Thr Thr Asn Lys
                165                 170                 175

Pro Val Asp Thr Ser Arg Pro Thr Val Val Ser Pro Lys Tyr Lys Asp
            180                 185                 190

Ile Lys Lys Ala Val Lys Leu Ile Asn Lys Ser Lys Lys Pro Val Met
        195                 200                 205

Leu Ile Gly Val Gly Ala Lys His Ala Lys Asp Glu Leu Arg Glu Phe
    210                 215                 220

Ile Glu Met Ala Lys Ile Pro Val Ile His Ser Leu Pro Ala Lys Thr
225                 230                 235                 240

Ile Leu Pro Asp Asp His Pro Tyr Ser Ile Gly Asn Leu Gly Lys Ile
                245                 250                 255

Gly Thr Lys Thr Ser Tyr Gln Thr Met Gln Glu Ala Asp Leu Leu Ile
            260                 265                 270

Met Val Gly Thr Asn Tyr Pro Tyr Val Asp Tyr Leu Pro Lys Lys Asn
        275                 280                 285

Ile Lys Ala Ile Gln Ile Asp Thr Asn Pro Lys Asn Ile Gly His Arg
    290                 295                 300

Phe Asn Ile Asn Val Gly Ile Val Gly Asp Ser Lys Ile Ala Leu His
305                 310                 315                 320

Gln Leu Thr Glu Asn Ile Lys His Val Ala Glu Arg Pro Phe Leu Asn
                325                 330                 335

Lys Thr Leu Glu Arg Lys Ala Val Trp Asp Lys Trp Met Glu Gln Asp
            340                 345                 350
```

-continued

Lys Asn Asn Ser Lys Pro Leu Arg Pro Glu Arg Leu Met Ala Ser
        355                 360                 365

Ile Asn Lys Phe Ile Lys Asp Asp Ala Val Ile Ser Ala Asp Val Gly
    370                 375                 380

Thr Ala Thr Val Trp Ser Thr Arg Tyr Leu Asn Leu Gly Val Asn Asn
385                 390                 395                 400

Lys Phe Ile Ile Ser Ser Trp Leu Gly Thr Met Gly Cys Gly Leu Pro
                405                 410                 415

Gly Ala Ile Ala Ser Lys Ile Ala Tyr Pro Asn Arg Gln Ala Ile Ala
            420                 425                 430

Ile Ala Gly Asp Gly Ala Phe Gln Met Val Met Gln Asp Phe Ala Thr
        435                 440                 445

Ala Val Gln Tyr Asp Leu Pro Leu Thr Val Phe Val Leu Asn Asn Lys
    450                 455                 460

Gln Leu Ala Phe Ile Lys Tyr Glu Gln Gln Ala Ala Gly Glu Leu Glu
465                 470                 475                 480

Tyr Ala Val Asp Phe Ser Asp Met Asp His Ala Lys Phe Ala Glu Ala
                485                 490                 495

Ala Gly Gly Lys Gly Tyr Thr Ile Lys Ser Ala Ser Glu Val Asp Ala
            500                 505                 510

Ile Val Glu Glu Ala Leu Ala Gln Asp Val Pro Thr Ile Val Asp Val
        515                 520                 525

Tyr Val Asp Pro Asn Ala Ala Pro Leu Pro Gly Lys Ile Val Asn Glu
    530                 535                 540

Glu Ala Leu Gly Tyr Gly Lys Trp Ala Phe Arg Ser Ile Thr Glu Asp
545                 550                 555                 560

Lys His Leu Asp Leu Asp Gln Ile Pro Pro Ile Ser Val Ala Ala Lys
                565                 570                 575

Arg Phe Leu

<210> SEQ ID NO 3
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 3
ccccatatgc acaaagtcca atta                                          24

<210> SEQ ID NO 4
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 4
cccctcgagt tcataagcgt ctacacc                                       27

<210> SEQ ID NO 5
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 5
tgattttgtt gactgtcgtt                                              20

<210> SEQ ID NO 6
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 6
tcatgtgaca cttcgatacc                                              20

<210> SEQ ID NO 7
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 7
aggtacagca acagtttggt                                              20

<210> SEQ ID NO 8
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 8
cttgtgctag tgcctcttct                                              20

<210> SEQ ID NO 9
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 9
ccccatatgg tcgtgaaaca acaaaaagac gc                                32

<210> SEQ ID NO 10
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 10
cccctcgaga tcatgagctt gtgcctcctc                                   30

<210> SEQ ID NO 11
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 11
cttatctttg gaattcgtta taacggg                                      27

<210> SEQ ID NO 12
<211> LENGTH: 27
<212> TYPE: DNA
<213> ORGANISM: Artificial sequence

```
<220> FEATURE:
<223> OTHER INFORMATION: Oligonucleotide primer

<400> SEQUENCE: 12
aataaatgaa ttaaacccgg gccaccg                                              27

<210> SEQ ID NO 13
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 13
ggtcaaatcg atacttaaac cttgg                                                25

<210> SEQ ID NO 14
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 14
ccgcttccgt cgacaaaaaa gcaggc                                               26

<210> SEQ ID NO 15
<211> LENGTH: 36
<212> TYPE: DNA
<213> ORGANISM: Artificial sequence
<220> FEATURE:
<223> OTHER INFORMATION: Oligonucleotide primer

<400> SEQUENCE: 15
attaatttgg atccttaaaa tgatagacag aaaggg                                    36

<210> SEQ ID NO 16
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 16 cctcccttc tgtctagcat gctaaatatc taaa                                       34

<210> SEQ ID NO 17
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 17
cccccatggc aaaaataaaa gcaaatgaag c                                         31

<210> SEQ ID NO 18
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 18
cccctcgagt aagaaacgtt ttgctgc                                              27
```

```
<210> SEQ ID NO 19
<211> LENGTH: 994
<212> TYPE: DNA
<213> ORGANISM: Staphylococcus aureus

<400> SEQUENCE: 19
gtaaagcaat taaagatatt gaaaatgaaa tgggcacgcc cttatttgat agaagtaaaa      60
gacatttaat tcttaccgat gcaggtcaaa ttttttatga gaaaagtaaa gaaattgttg     120
cactgtatga ttatttacca tctgaaatgg aacgcttgaa tggactggaa acaggacata     180
taaacatggg catgtcggca gtcatgaata tgaagattct tatcaatatt cttggtgcat     240
tccatcaaca atatccaaat gttacatata atttgataga aaatggcggt aaaacaattg     300
aacagcaaat tatcaatgat gaagtagata taggcgtgac cactttgcca gtcgatcatc     360
atattttcga ttatactacc ctagataagg aagatttgcg acttatcgtg agcagagagc     420
atcgactcgc aaaatatgaa actgttaaac tcgaagattt agcaggtgaa gacttcattt     480
tatttaataa agacttttac ttgaatgata aaattattga aatgctaaa acgttggct      540 ttgttccgaa tactgtagcg caaatttcac aatggcatgt tatagaagat ttagttacga     600
atgaattagg tattagtatt ttaccaacat caatttcaga gcaactaaat ggagatgtga     660
agctgctacg cattgaagat gctcatgtac attgggaatt aggtgttgtt tggaagaagg     720
ataaacaatt aagtcatgcc acaacgaaat ggatagaatt tttgaaagac cgtttaggct     780
aacatattaa taaagcactc attatttaag gcgcatcatt acgtgggtca ttgaaataat     840
gagtgttttt ttgtgaaaat gaagtgaaat ttagagagcg tttccataga aaatagtaat     900
acaaactata aaaaagagt attttatat tgtgtacgcc atctttataa tagttattgt       960
aacaatttag acatatttag aaagggatgg cgcc                                 994

<210> SEQ ID NO 20
<211> LENGTH: 717
<212> TYPE: DNA
<213> ORGANISM: Aequorea Victoria

<400> SEQUENCE: 20
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcccgtt atccggatca tatgaaacgg     240
catgactttt tcaagagtgc catgcccgaa ggttatgtac aggaacgcac tatatctttc     300
aaagatgacg ggaactacaa gacgcgtgct gaagtcaagt ttgaaggtga tacccttgtt     360
aatcgtatcg agttaaaagg tattgatttt aaagaagatg gaaacattct cggacacaaa     420
ctcgagtaca actataactc acacaatgta tacatcacgg cagacaaaca aaagaatgga     480
atcaaagcta acttcaaaat tcgccacaac attgaagatg gatccgttca actagcagac     540
cattatcaac aaaatactcc aattggcgat ggccctgtcc ttttaccaga caaccattac     600
ctgtcgacac aatctgccct ttcgaaagat cccaacgaaa agcgtgacca catggtcctt     660
cttgagtttg taactgctgc tgggattaca catggcatgg atgagctcta caaataa       717

<210> SEQ ID NO 21
<211> LENGTH: 540
<212> TYPE: DNA
<213> ORGANISM: Staphylococcus aureus
```

<400> SEQUENCE: 21
tgataataac gcaagtgcaa ttgcgaatga tatgtcggcg aattttgatc aaagcttacc        60
tgttgaaatt gacgataaaa ttcacatgtt aaagcaacaa atattattg ggattggcac        120 acataatggt attacaacca tacatacaac gaatcataaa tacgaaacaa cagagccatt       180
gaatcgttat gaaaaacgat tgaatcccac ttattttata cgtattcatc gttcatatat       240
tattaacacg aaacacatta aagaagtgca acaatggttt aactatactt atatggtaat      300
attgacaaat ggtgtcaaga tgcaagttgg acgttcattt atgaaagatt ttaaagcgtc      360
gataggatta ctttaacagt aatccttttt tttatgcatt ttacctatga tattttgtat     420
ttcggactaa aaatcacgca aatcgaagtg agccatctat actttagtta aatcaaacgt     480
aggaggcaat ggtcgtgaaa caacaaaaag acgcatcaaa accagcacac ttttttcacc    540

<210> SEQ ID NO 22
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 22
ggccggatcc tcacttctct agggaaattg c                                      31

<210> SEQ ID NO 23
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 23
gcgcctgcag acatgcccat gtttatatgt cc                                     32

<210> SEQ ID NO 24
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 24
cccggtacca tccctttctc gagatgtcta aattg                                  35

<210> SEQ ID NO 25
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 25
ggctttgttc cgaattctgt agcgca                                            26

<210> SEQ ID NO 26
<211> LENGTH: 33
<212> TYPE: DNA
<213> ORGANISM: Artificial sequence
<220> FEATURE:
<223> OTHER INFORMATION: Oligonucleotide primer

<400> SEQUENCE: 26

-continued

```
cccggatccg taaaagctca atacctcacc tcg                           33
```

<210> SEQ ID NO 27
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 27

```
cccgaattcg gaaacgctct ctaaatttca c                             31
```

<210> SEQ ID NO 28
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 28

```
gcctccttgc ttaacgactt c                                        21
```

<210> SEQ ID NO 29
<211> LENGTH: 33
<212> TYPE: DNA
<213> ORGANISM: Artificial sequence
<220> FEATURE:
<223> OTHER INFORMATION: Oligonucleotide primer

<400> SEQUENCE: 29

```
gccgttgtcg acaattgtga taacctttca atc                           33
```

<210> SEQ ID NO 30
<211> LENGTH: 39
<212> TYPE: DNA
<213> ORGANISM: Artificial sequence
<220> FEATURE:
<223> OTHER INFORMATION: Oligonucleotide primer

<400> SEQUENCE: 30

```
agacatattt agaaagggat cccgccatgc acaaagtcc                     39
```

<210> SEQ ID NO 31
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 31

```
cccgaattcg tcacagttag atctaagtct tgctg                         35
```

<210> SEQ ID NO 32
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 32

```
aatacaggat ccccttcaga tgtagc                                   26
```

<210> SEQ ID NO 33
<211> LENGTH: 32
<212> TYPE: DNA
<213> ORGANISM: Artificial sequence

```
<220> FEATURE:
<223> OTHER INFORMATION: Oligonucleotide primer

<400> SEQUENCE: 33
cccatcgatt gcatgtacgt atgatgccgg ca                              32

<210> SEQ ID NO 34
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 34
cccctgcagt agttttatag ggcaagcgct ga                              32

<210> SEQ ID NO 35
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 35
ccccatatgg tcgtgaaaca acaaaagacg c                               31

<210> SEQ ID NO 36
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 36
cccctcgaga tcatgagctt gtgcctcct                                  29

<210> SEQ ID NO 37
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 37
agtacactgc agccgatatg                                            20

<210> SEQ ID NO 38
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 38
ctataggatc ataaccgatt g                                          21

<210> SEQ ID NO 39
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 39
ggtacattag gcacattaat ggc                                        23
```

<210> SEQ ID NO 40
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 40
ctctaatttc gtctgcaata tc                                          22

<210> SEQ ID NO 41
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 41
ctcggtaccc gttttcagtt ccttctatgt ca                               32

<210> SEQ ID NO 42
<211> LENGTH: 33
<212> TYPE: DNA
<213> ORGANISM: Artificial sequence
<220> FEATURE:
<223> OTHER INFORMATION: Oligonucleotide primer

<400> SEQUENCE: 42
ataggatcca gatctcttgt agcagcaggg att                              33

<210> SEQ ID NO 43
<211> LENGTH: 39
<212> TYPE: DNA
<213> ORGANISM: Artificial sequence
<220> FEATURE:
<223> OTHER INFORMATION: Oligonucleotide primer

<400> SEQUENCE: 43
ttcggatccc tcgagactag ttgtaactcc tctgccact                        39

<210> SEQ ID NO 44
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 44
atagtcgaca cgcgtgcttt catccttccg ttta                             34

<210> SEQ ID NO 45
<211> LENGTH: 36
<212> TYPE: DNA
<213> ORGANISM: Artificial sequence
<220> FEATURE:
<223> OTHER INFORMATION: Oligonucleotide primer

<400> SEQUENCE: 45
gtgagatcta tcgattttcg ttcgtgaata catgtt                           36

<210> SEQ ID NO 46
<211> LENGTH: 34
<212> TYPE: DNA
<213> ORGANISM: Artificial sequence
<220> FEATURE:
<223> OTHER INFORMATION: Oligonucleotide primer

```
<400> SEQUENCE: 46
gtcctcgagc atatgcaagg gtttattgtt ttct                        34

<210> SEQ ID NO 47
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 47
atcggtacca catcgcacta caatcgg                                27

<210> SEQ ID NO 48
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 48
gtcagatctt catacagtaa ccacctct                               28

<210> SEQ ID NO 49
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 49
gtgactagtt tgctactaaa gcggaaagg                              29

<210> SEQ ID NO 50
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 50
gtgacgcgtg ctttcatcct tccgttta                               28

<210> SEQ ID NO 51
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 51
gtcactagtc tgtagaggga acaatcgc                               28

<210> SEQ ID NO 52
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 52
atgacgcgta tcggatatga aagctgacc                              29
```

METHODS FOR ALTERING ACETIC ACID PRODUCTION AND ENHANCING CELL DEATH IN BACTERIA

CROSS REFERENCE TO RELATED APPLICATIONS

This is the U.S. National Stage of PCT International Application No. PCT/US2005/017604, filed May 20, 2005, which was published in English under PCT Article 21(2), which in turn claims the benefit of U.S. Provisional Application No. 60/573,431, filed May 21, 2004, and U.S. Provisional Application No. 60/642,039, filed Jan. 6, 2005. These applications are incorporated herein in their entirety.

STATEMENT OF GOVERNMENT SUPPORT

This invention was made in part with United States government support pursuant to NIH grant no. R01AI038901; NIH-NRRI grant no. P20RR15587; and Department of Defense grant no. DAAD 19-03-0191. The United States government may have certain rights in the invention.

FIELD

A first aspect of this disclosure relates to methods of increasing cultured cell growth yields and/or protein production from bacterial cell cultures. More particularly, this document relates to methods for reducing acetic acid/acetate production in cultures by altering the expression and/or activity of the cidABC operon, a gene therein, or a homolog or a regulator thereof, as well as cells and compositions for use in such methods. This document also relates to methods for enhancing bacterial cell death and methods for identifying agents that increase the susceptibility of bacteria to cell death.

BACKGROUND

Most bacterial species produce secreted proteins that function to exploit biological niches (e.g., host systems) or in the metabolism of a variety of environmental energy sources. The biotechnology industry has taken advantage of these organisms to produce secreted recombinant proteins of commercial value. An advantage of secreted proteins is that large quantities of recombinant proteins can be easily purified away from the bulk of the bacterial proteins that remain cell-associated. Gram-positive species, such as *Bacillus subtilis*, are particularly useful because of the absence of an outer cell membrane that can complicate the purification of secreted products.

A major limiting factor that the industry faces is the growth yield that can be achieved using these recombinant organisms. During aerobic, exponential growth in the presence of glucose, bacteria metabolize glucose via glycolysis and inhibit the TCA cycle. Consequently, the products of glycolysis are converted into acetate and secreted into the extracellular fluid for use once the glucose is depleted from the medium. This secreted acetate is converted into acetic acid, which becomes toxic at high levels, inducing cell death. Current industrial technology often relies on the removal of the secreted acetate during growth, thus allowing the bacteria to reach higher cell densities and produce increased protein yields. Unfortunately, the removal of acetate from the medium is costly and can outweigh the financial benefits of achieving higher growth yields. An alternative strategy involves achieving a careful balance between the amount of carbon source utilized and the amount of acetate secreted. However, the maximum growth potential that is possible with higher levels of glucose is, ultimately, negatively impacted by the increased cell death induced by toxic acetate byproducts that are generated by growth in the presence of this carbon source.

The cid and lrg operons of *S. aureus* affect extracellular murein hydrolase activity and penicillin tolerance (Brunskill and Bayles, *J. Bacteriol.* 178(3): 611-618, 1996; Groicher et al., *J. Bacteriol.* 182: 1794-1801, 2000; Rice et al., *J. Bacteriol.* 185: 2635-2643, 2003). Disruption of the lrg operon in the laboratory strain RN6390 increased extracellular murein hydrolase activity and decreased penicillin tolerance, whereas disruption of the cid operon decreased extracellular murein hydrolase activity and increased penicillin tolerance (Groicher et al., *J. Bacteriol.* 182: 1794-1801, 2000; Rice et al., *J. Bacteriol.* 185: 2635-2643, 2003).

The lrgA and cidA gene products display structural similarities to the bacteriophage holin family of proteins, which control the timing and onset of bacteriophage-induced cell lysis (Brunskill & Bayles, *J. Bacteriol.* 178(19): 5810-5812, 1996; Bayles, *Trends Microbiol.* 8(6): 274-278, 2000; Groicher et al., *J. Bacteriol.* 182: 1794-1801, 2000; Rice et al., *J. Bacteriol.* 185: 2635-2643, 2003). Based on these similarities, along with the phenotypic consequences of the cid and lrg mutations, it is likely that the lrgA and cidA gene products regulate murein hydrolase activity in a manner analogous to antiholin and holins (inhibitor and effector holins), respectively (Bayles, *Trends Microbiol.* 8(6): 274-278, 2000; Rice & Bayles, *Mol Microbiol* 50: 729-738, 2003).

In view of the relationship between acetic acid regulation and cell death, there exists a continuing need for methods, cells, and compositions that can be used to reduce acetic acid production in bacterial cell culture, thereby enabling growth to higher cell densities and increased protein yields. The present disclosure addresses this need and provides unexpected benefits with respect to controlling acetic acid metabolism and regulating cell death in bacteria.

SUMMARY OF THE DISCLOSURE

The cidC gene affects the production/secretion of acetic acid by bacterial cells. Inactivating this gene, or the pyruvate oxidase encoded thereby, either directly or indirectly, allows for growth of bacteria in the presence of glucose without the accumulation of deleteriously high levels of acetic acid in the culture medium. A result of this is enhanced survival and increased longevity in culture as compared to previously available strains. In addition, the mutant cells exhibit increased growth once stationary phase has been reached. Both the maintenance of higher cell numbers (biomass maintenance) and increased longevity contribute to the enhanced commercial potential of these mutant bacterial cells, and other bacterial cells comprising similar mutations in the cidC gene, the cidABC operon, or a homolog thereof.

The present disclosure also provides bacterial host cells, expression methods and systems for enhanced bacterial production and secretion of heterologous or homologous products, such as proteins. In one embodiment, a bacterial cell is genetically engineered to have a deletion or mutation in a cidABC gene or operon, or homolog thereof, such that the activity of the cidC pyruvate oxidase is reduced, thereby measurably reducing the production of acetic acid by that bacterial cell. In another embodiment, a bacterial cell is genetically engineered to comprise a mutation or deletion in another gene or operon, which influences the cidABC operon such that the activity of the cidC pyruvate oxidase is reduced, thereby measurably reducing the production of acetic acid by that bacterial cell.

The present disclosure provides methods for increasing the yield of a bacterial culture, measured for instance as production of a product, which method comprises obtaining a bacterium capable of expressing the product, which bacterium comprises a mutation that reduces the expression or function of at least one gene in a cidABC operon, e.g., a cidC gene, or homolog thereof; and culturing the mutant bacterium in the presence of glucose and under conditions suitable for expression of the product. In examples of such methods, the mutation results in a measurable reduction of acetic acid production by the bacterium.

It has also been determined that agents and conditions that increase expression of the products encoded by the cidABC operon increase the susceptibility of bacteria to cell death. Based on this property of the cidABC operon, compositions and methods useful for the identification of agents that enhance bacterial cell death are disclosed herein, as are methods for enhancing cell death. In an embodiment, an agent that induces expression of the cidABC operon is administered in combination with an agent with bactericidal (antibiotic) properties to increase the rate or extent of bacterial cell death.

The foregoing and other embodiments, features and advantages will become more apparent from the following detailed description of several embodiments, which proceeds with reference to the accompanying figures.

BRIEF DESCRIPTION OF THE FIGURES

FIG. 3A: Aliquots of 50 μg of extracellular proteins isolated from 16-hour cultures of UAMS-1 (wild-type; circles) and KB1050 (cidA mutant; triangles) grown in either the presence of 35 mM glucose (closed symbols) or in the absence of glucose (open symbols) were each added to a 1 mg·ml$^{-1}$ suspension of *M. luteus* cell walls, and the murein hydrolase activity of each sample was measured as a decrease in turbidity over a 4-hour time course experiment. These data represent the average of three independent experiments, and the error bars correspond to the standard errors of the means.

FIG. 4A: This graph depicts the CFU/ml of each culture before and after addition of rifampin. The time at which rifampin was added to each culture is indicated by an arrow.

FIG. 6A: Total cellular RNA was isolated from UAMS-1 grown to late exponential growth phase (4-hours post inoculum) in either NZY pH 7.5 (lane 1), NZY pH 7.5+35 mM glucose (lane 2), NZY pH 5.0 (HCl) (lane 3), NZY pH 5.0 (HAc) (lane 4), and 10 μg of each sample was separated through a 1% (wt/vol) agarose-formaldehyde gel, transferred to a nylon membrane, and hybridized to cidA- and lrgA-specific DIG-labeled probes. The sizes of each transcript were determined by comparison to an RNA ladder (Invitrogen) run on the same gel.

FIG. 8A: the transcription start site is indicated by asterisks, whereas putative −10 and −35 elements are underlined. The putative GTG start codon is in bold and the predicted ribosome binding site is double underlined. Transcripts spanning cidABC (3.0 kb) and cidBC (2.7 kb) are indicated above corresponding genes.

(FIG. 17A) Six hundred microliters of supernatants from 16-hours cultures of UAMS-1 and KB1097 grown in the presence of 35 mM glucose were each used to determine acetoin production levels. The development of a red color was monitored for 30 minutes at room temperature, and the $OD_{540}$ was measured. The level of acetoin production in UAMS-1 culture supernatant was normalized to that of wild-type stain UAMS-1. These data are the average of three independent experiments. The error bars on the graph correspond to the standard errors of the means.

FIG. 18A illustrates results of a quantitative cell wall hydrolysis assay, whereas (FIG. 18A) One hundred micrograms of extracellular proteins isolated from 16-hour cultures of UAMS-1 (wild-type; circles), KB1050 (cidA mutant; down-triangles), KB1090 (cidR mutant; squares), and KB1097 (alsSD mutant; up-triangles) grown in the presence of 35 mM glucose were each added to a 1.0 mg/ml suspension of *M. luteus* cells, and the murein hydrolase activity of each sample was measured as a decrease in turbidity over a 4-hour time course experiment. These data are the average of three independent experiments. The error bars on the graph correspond to the standard errors of the means. (FIG. 18B) Fifteen micrograms of extracellular proteins, isolated from 16-hour cultures of UAMS-1, KB1050, KB1090, and KB1097 grown in the presence of 35 mM glucose, was separated in a sodium dodecyl sulfate-polyacrylamide gel electrophoresis gel containing 1 mg/ml of *M. luteus* cell wall, followed by an overnight incubation at 37° C. in a buffer containing Triton X-100 and staining with methylene blue. This zymogram is representative of results obtained from three independent experiments. The migration of molecular mass markers (in kilodaltons) are indicated to the left of the gel.

BRIEF DESCRIPTION OF THE SEQUENCE LISTING

Figure 1:
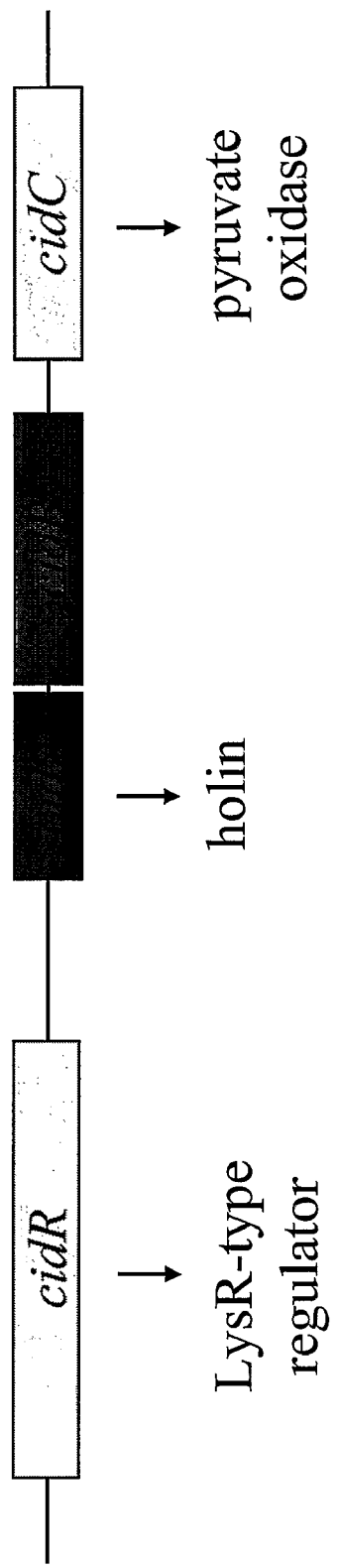
FIG. 1 is a schematic representation of the cidABC operon, including the cidR gene.

The Sequence Listing is submitted as an ASCII text file in the form of the file named 68410-04_RepSeqList.txt (~200,000 bytes), created on Sep. 17, 2010, which is incorporated by reference herein.

SEQ ID NO: 1 is the nucleotide sequence of *S. aureus* cidC (from the cidABC operon, in AY581892, which is incorporated herein by reference):

SEQ ID NO: 2 is the amino acid sequence of *S. aureus* cidC:

SEQ ID NOs: 3-10 are oligonucleotide primers used in Example 1:

SEQ ID NOs: 11-18 are oligonucleotide primers used in Example 2.

SEQ ID NO: 19 is the polynucleotide sequence of the cidA promoter.

SEQ ID NO: 20 is the coding sequence of green fluorescent protein.

SEQ ID NO: 21 is the polynucleotide sequence of the lrgAB promoter.

SEQ ID NOs: 22-30 are oligonucleotide primers used in Example 3.

SEQ ID NOs: 31-40 are oligonucleotide primers used in Example 4.

SEQ ID NOs: 41-52 are oligonucleotide primers used in Example 5.

SEQ ID NO: 53 is the nucleotide sequence surrounding the *S. aureus* cidR transcription start site.

DETAILED DESCRIPTION

Various aspects of the present disclosure are based on the observation that expression of the cidABC and lrgAB operons of *Staphylococcus aureus*, as well as murein hydrolase activity and tolerance to antibiotics, such as rifampicin, vincomycin and penicillin, are responsive to by-products of carbohydrate metabolism. The *S. aureus* lrg and cid operons encode homologous proteins that regulate extracellular murein hydrolase activity and penicillin tolerance in a diametrically-opposing manner. It has been postulated that CidA and LrgA act in a manner analogous to bacteriophage holins and antiholins, respectively, and that these proteins ultimately serve as molecular control elements of bacterial cell death. Although cidBC transcription is abundant in sigma B proficient strains, cidABC transcription is only minimally expressed under standard growth conditions. Transcription of cidABC and lrgAB is induced by elevated (0.75% wt/vol or 35 mM) glucose as cells approach stationary phase. Under these conditions, murein hydrolase activity, along with sensitivity to rifampin, are greatly increased. These effects are not observed with a cidA mutant strain, indicating that the increased murein hydrolase activity and antibiotic sensitivity observed are dependent on enhanced cidABC expression. Acetic acid accumulation in the culture supernatant, a by-product of glucose metabolism, is responsible for the increase in cidABC and lrgAB expression.

I. Overview of Several Embodiments

A first embodiment is a bacterial cell (e.g., a gram-positive or gram-negative cell) comprising a mutation in a cidABC operon or homolog thereof, which mutation measurably reduces acetate production by the cell when the cell is grown in medium containing a metabolizable carbon source, such as glucose. In examples of such cells, the mutation measurably reduces acetate production by the cell, in comparison to an isogenic cell not comprising the mutation, when grown in medium containing a metabolizable carbon source, such as, at least about 0.5% glucose or at least about 20-25 mM glucose.

Another embodiment is a method for producing a polypeptide (or other product), which method involves cultivating a mutant bacterial cell (e.g., a gram-positive or gram-negative cell) comprising a mutation in a cidABC operon or homolog thereof, which mutation measurably reduces acetate production by the mutant bacterial cell in comparison to an isogenic cell not having the mutation; and isolating the polypeptide from the culture medium, wherein the mutant bacterial cell further comprises a nucleic acid encoding the polypeptide. Examples of this method yield at least a 10% increase (or more) in polypeptide (or other product) production compared to cultivating an isogenic bacterial cell that does not comprise the mutation in the cidABC operon or homolog thereof. Other examples of this method yield at least a 10% increase (or more) in biomass compared to cultivating an isogenic bacterial cell that does not comprise the mutation in the cidABC operon or homolog thereof. For instance, some methods will provide at least a 25% increase in biomass compared to cultivating an isogenic bacterial cell that does not comprise the mutation in the cidABC operon or homolog thereof.

In examples of the methods for producing a polypeptide (or other product), the mutation measurably reduces acetate production by the mutant bacterial cell, in comparison to an isogenic cell not comprising the mutation, when grown in medium comprising at least about 20 mM glucose or other metabolizable carbon source.

Yet another embodiment is a method for increasing yield in a bacterial cell culture (e.g., a gram-positive or gram-negative cell culture), comprising culturing a bacterial cell comprising a mutation in a cidC gene or homolog thereof encoding a pyruvate oxidase, wherein the mutation measurably reduces acetate production by the bacterial cell in comparison to an isogenic cell not having the mutation, and wherein the reduced acetate production results in increased yield.

In examples of the method for increasing yield in a bacterial cell, the increased yield is measured as an increase in bacterial biomass, an increase in production of the product, an increase in turbidity, an increase in optical density, or a combination of two or more thereof. By way of example, methods yield at least a 10% increase (or more) in yield compared to an isogenic bacterial cell that does not comprise the mutation in the cidABC operon or homolog thereof. In others, the method yields at least a 10% increase (or a 25% increase, or more) in bacterial biomass compared to an isogenic bacterial cell culture that does not comprise the mutation in the cidABC operon or homolog thereof.

The mutation in certain of the provided methods measurably reduces acetate production by the bacterial cell comprising the mutation, in comparison to an isogenic cell not comprising the mutation, when grown in medium comprising at least 0.5% glucose.

Particular cells provided herein, and cells used in the methods described herein, are cells that comprise a mutation in a cidC gene or homolog thereof encoding a pyruvate oxidase. For instance, the mutation in some cases is a knockout mutation, an inactivation mutation, or a functional mutation in the cidC gene or homolog thereof encoding a pyruvate oxidase. Optionally, the pyruvate oxidase encoded by the cidC gene or homolog thereof is at least 45% identical to prototypical *S. aureus* CidC (SEQ ID NO: 2). In particular examples, the cidC gene or homolog thereof is selected from Table 1.

It is particularly contemplated that the bacterial cell in embodiments described herein is an *Actinomyces* species, a *Bacillus* species, a *Bifidobacteria* species, a *Clostridium* species, a *Corynebacterium* species, a *Escherichia* species, a *Lactobacillus* species, a *Lactococcus* species, a *Propionibacteria* species, a *Pseudomonas* species, a *Staphylococcus* species, a *Streptomyces* species, or a *Streptoverticillium* species cell. Specific example bacterial cells are selected from the group consisting of: *E. coli, S. aureus, Streptomyces coelicolor, B. alcalophilus, B. amyloliquefaciens, B. brevis, B. cereus, B. circulans, B. clausii, B. coagulans, B. firmus, B. lautus, B. lentus, B. licheniformis, B. megaterium, B. nocardia, B. polymyxa, B. popilliae, B. pulvifaciens, B. pumilus, B. sphaericus, B. stearothermophilus, B. subtilis*, and *B. thuringiensis*.

Another aspect of the disclosure relates to methods for enhancing cell death in bacteria. Expression of the cidABC operon is induced by conditions and agents that increase bacterial sensitivity to cell death, for example, cell death induced by exposure to antibiotics. Based on this discovery, methods are described for identifying agents that enhance bacterial cell death. A cell containing a reporter construct in which a detectable reporter (that is, a reporter that is directly detectable or a reporter that is indirectly detectable by the production of a detectable product) is operably linked to the transcription regulatory sequences of the cidABC operon is contacted with an agent, and expression of the reporter is evaluated. Agents that induce expression of the reporter by inducing expression regulated by the cidABC promoter are expected to increase susceptibility of the bacterial cell to cell death. For example, in an embodiment, methods are provided for identifying agents that cause cell death directly (that is, that result in bacterial cell death in the absence of any additional agent). In another embodiment, methods are provided for identifying agents that increase the sensitivity of bacteria to killing by antibiotics and other bactericidal agents. It is contemplated that such agents can be administered, e.g., in combination with an antibiotic, to improve the efficacy of anti-bacterial therapy.

II. Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural references unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

Acetate/Acetic Acid: Acetic acid has the structure $CH_3COOH$. An "acetate" is either (1) a salt of an acetic acid in which the terminal hydrogen atom is replaced by a metal (e.g., $Cu(CH_3COO)_2$), or (2) an ester of an acetic acid in which the terminal hydrogen is replaced by a radical (e.g., alkyl, aryl, etc) as in ethyl acetate ($CH_3COOC_2H_5$). Thus, structurally acetate/acetic acid is $CH_3COO$—R, wherein R is H or a metal, alkyl, aryl, etc. (in other words, the acetate/acetic acid moiety is $CH_3COO$—R).

It is understood in the art that acetate can exist in a variety of ionization states depending upon the surrounding conditions, if in solution, or out of solution from which they are prepared if in solid form. The use of a term herein, such as, for example, acetic acid, to designate such molecules is intended to include all ionization states of the organic molecule referred to. Thus, for example, both "acetic acid" and "acetate" refer interchangeably herein to the same moiety, and are not intended to specify particular ionization states.

Methods for measuring the amount of acetate are known to those of ordinary skill in the art, and include but are not limited to the methods described herein.

Antisense, Sense, and Antigene: Double-stranded DNA (dsDNA) has two strands, a 5' to 3' strand, referred to as the plus strand, and a 3' to 5' strand (the reverse complement), referred to as the minus strand. Because RNA polymerase adds nucleic acids in a 5' to 3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. Antisense molecules can be used to suppress expression from a specific target gene.

cDNA: A DNA molecule lacking internal, non-coding segments (e.g., introns) and regulatory sequences that determine transcription. By way of example, cDNA can be synthesized in the laboratory by reverse transcription from messenger RNA extracted from cells.

The term "cell death" or "bacterial cell death" includes bacterial cell death that results from a genetically encoded cell death process that causes self destruction in response to signals specific to the metabolic state of the cell, the environmental conditions in which the cell resides, and/or cell cycle specific effectors. This phenomenon is sometimes referred to in the literature as "programmed cell death."

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Non-limiting examples of conservative amino acid substitutions include: Ala for Ser; Arg for Lys; Asn for Gln or His; Asp for Glu; Cys for Ser; Gln for Asn; Glu for Asp; His for Asn or Gln; Ile for Leu or Val; Leu for Ile or Val; Lys for Arg, Gln or Glu; Met for Leu or Ile; Phe for Met, Leu or Tyr; Ser for Thr; Thr for Ser; Trp for Tyr; Tyr for Trp or Phe; and Val for Ile or Leu;

DNA (deoxyribonucleic acid): DNA is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

Enriched: The term "enriched" means that the concentration of a material is at least about 2, 5, 10, 100, or 1000 times its natural concentration (for example), advantageously at least 0.01% by weight. Enriched preparations of about 0.5%, 1%, 5%, 10%, and 20% by weight are also contemplated.

Functional deletion: A mutation, partial or complete deletion, insertion, or other variation made to a gene sequence, which inhibits production of the gene product, and/or renders the gene product non-functional. For example, functional deletion of cidC in *S. aureus*, or PoxB in *E. coli*, prevents or reduces the production of acetate from pyruvate by pyruvate oxidase, which is encoded by the cidC gene. This functional deletion of cidC in *S. aureus* inactivates the encoded pyruvate oxidase, which results in increased growth and higher biomass and other yields of the *S. aureus* in the presence of glucose in the growth medium.

Holins: Bacterial or bacteriophage-encoded proteins that function to control murein hydrolase activity and, ultimately, the lytic potential of the bacterial cell. They have been proposed to be the primary regulators of bacterial cell death.

The term "homologous protein" refers to a protein or polypeptide native or naturally occurring in a (bacterial) cell. It is also contemplated herein that the bacterium in some embodiments produces a homologous protein via recombinant DNA technology. For instance, in some such examples, the bacterial host cell comprises a deletion or interruption of the nucleic acid encoding the naturally occurring homologous protein, such as a protease, and further comprises a nucleic acid encoding the homologous protein re-introduced in a recombinant form (either autonomously replicating or integrated into the bacterial genome).

Hybridization: Nucleic acid molecules that are complementary to each other hybridize by hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA or PNA target. An oligonucleotide need not be 100% complementary to its target nucleic acid sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, for example under physiological conditions in the case of in vivo assays, or under conditions in which the assays are performed.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. in *Molecular Cloning: A Laboratory Manual*, Cold Spring Harbor Laboratory Press (1989), chapters 9 and 11, herein incorporated by reference.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification can be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: Detectable marker or reporter molecules, which can be attached to nucleic acids, proteins, or other molecules. Typical labels include fluorophores, radioactive isotopes, ligands, chemiluminescent agents, metal sols and colloids, and enzymes. Methods for labeling nucleic acids, and guidance in the choice of labels useful for various purposes, are discussed, e.g., in Sambrook et al., in *Molecular Cloning: A Laboratory Manual*, Cold Spring Harbor Laboratory Press (1989) and Ausubel et al, in *Current Protocols in Molecular Biology*, Greene Publishing Associates and Wiley-Intersciences (1987).

Murein hydrolase: Also referred to as peptidoglycan hydrolase or autolysin. Any one of a family of enzymes that cleave specific bonds within the bacterial cell wall. These enzymes include N-acetylglucosaminidases, N-acetylmuramyl-L-alanine amidases, lytic transglycosylases, D,D-endopeptidases, and carboxypeptidases.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which can result in the misreading of a large number of codons (and often leads to abnormal termination of the encoded product due to the presence of a stop codon in the alternative frame). One specific contemplated mutation is a so-called "knockout mutation," which removes (deletes) essentially all of the coding sequence of a gene or otherwise renders it incapable of serving as a template for production of a message transcript.

Nucleic acid: A deoxyribonucleotide or ribonucleotide polymer in either single or double stranded form, and unless otherwise limited, encompassing known analogues of natural nucleotides that hybridize to nucleic acids in a manner similar to naturally occurring nucleotides.

Nucleic acid molecules representing genes: Any nucleic acid, for example DNA (intron or exon or both), cDNA or RNA, of any length suitable for use as a probe or other indicator molecule, and that is informative about the corresponding gene.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear single-stranded polynucleotide sequence ranging in length from 2 to about 5,000 bases, for example a polynucleotide (such as DNA or RNA) which is at least 6 nucleotides, for example at least 10, 12, 15, 18, 20, 25, 50, 100, 200, 1,000, or even 5,000 nucleotides long. Oligonucleotides are often synthetic but can also be produced from naturally occurring polynucleotides.

An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Such analog molecules can also bind to or interact with polypeptides or proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): A series of nucleotide triplets (codons) coding for amino acids without any internal termination codons. These sequences are usually translatable into a peptide.

Peptide Nucleic Acid (PNA): An oligonucleotide analog with a backbone comprised of monomers coupled by amide (peptide) bonds, such as amino acid monomers joined by peptide bonds.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different isolates, or different geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNases, and so forth).

The term "polynucleotide" or "nucleic acid sequence" refers to a polymeric form of nucleotides at least 10 bases in length. Nucleotides can be ribonucleotides, deoxyribonucleotides, or modified forms of either nucleotide. The term includes single and double forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide.

The term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide, for example such a fragment which exhibits at least one useful epitope. The term "functional fragments of a polypeptide" refers to all fragments of a polypeptide that retain an activity of the polypeptide.

As used herein, the term "product" refers to any naturally occurring or recombinantly introduced product obtainable from the bacterium. Such products include but are not limited to proteins (such as enzymes), peptides, anti-microbial compounds, antibiotics, antigens, antibodies, surfactants, and chemical products.

Purified: The term purified does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid can be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

A recombinant protein is one that is encoded by nucleic acid which has been introduced into the microorganism. The nucleic acid can be introduced, on an expression vector having signals capable of expressing the protein encoded by the introduced nucleic acid or the nucleic acid can be integrated into the microorganism chromosome. The recombinant protein can be heterologous to the microorganism or homologous to the microorganism. As used herein, the term "heterologous protein" refers to a protein or polypeptide that does not naturally occur in a gram-positive host cell.

Examples of recombinant proteins include enzymes such as hydrolases (e.g., proteases, cellulases, amylases, carbohydrases, glucoamylases, and lipases); isomerases (e.g., racemases, epimerases, tautomerases, and mutases); transferases; kinases; oxidases; and phophatases. Also contemplated are therapeutically significant proteins or peptides, such as growth factors, cytokines, ligands, receptors, inhibitors, vaccines, and antibodies. The recombinant protein itself can be a naturally occurring protein, or one that is mutated, by way of point mutation, short or long deletion or insertion, or fusion to another protein or peptide, for instance.

RNA: A typically linear polymer of ribonucleic acid monomers, linked by phosphodiester bonds. Naturally occurring RNA molecules fall into three classes, messenger (mRNA, which encodes proteins), ribosomal (rRNA, components of ribosomes), and transfer (tRNA, molecules responsible for transferring amino acid monomers to the ribosome during protein synthesis). Total RNA refers to a heterogeneous mixture of all three types of RNA molecules.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., two *Bacillus* sequences), compared to species more distantly related (e.g., a *Bacillus* sequence compared to a *Corynebacterium* sequence). Typically, orthologs are at least 40% similar (conserved) at the amino acid level when comparing bacterial orthologous sequences. More closely related bacterial genus and species will share more similarity and higher sequence identity, both that the nucleotide and amino acid level.

Methods of alignment of sequences for comparison are well known. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad Sci. USA* 85:2444, 1988; Higgins & Sharp, Gene, 73:237-44, 1988; Higgins & Sharp, CABIOS 5:151-3, 1989; Corpet et al., *Nuc. Acids Res.* 16:10881-90, 1988; Huang et al., *Computer Appls. Biosci.* 8, 155-65, 1992; and Pearson et al., *Meth. Mol. Biol.* 24:307-31, 1994. Altschul et al., *J. Mol Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx. Each of these sources also provides a description of how to determine sequence identity using this program.

Homologous sequences are typically characterized by possession of at least 40%, 50%, 60%, 70%, 75%, 80%, 90%, 95% or at least 98% sequence identity counted over the full length alignment with a sequence using the NCBI Blast 2.0, gapped blastp set to default parameters. Queries searched with the blastn program are filtered with DUST (Hancock and Armstrong, *Comput. Appl. Biosci.* 10:67-70, 1994). It will be appreciated that these sequence identity ranges are provided for guidance only; it is entirely possible that strongly significant homologs could be obtained that fall outside of the ranges provided.

Nucleic acid sequences that do not show a high degree of identity can nevertheless encode similar amino acid sequences, due to the degeneracy of the genetic code or sequence bias found in different bacterial species.

An alternative indication that two nucleic acid molecules are closely related is that the two molecules hybridize to each other under stringent conditions, as described under "specific hybridization."

Specific hybridization: Specific hybridization refers to the binding, duplexing, or hybridizing of a molecule only or substantially only to a particular nucleotide sequence when that sequence is present in a complex mixture (e.g., total cellular DNA or RNA). Specific hybridization can also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. (In: *Molecular Clonzing: A Laboratory Manual*, Cold Spring Harbor, N.Y., 1989 ch. 9 and 11). By way of illustration only, a hybridization experiment can be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Traditional hybridization with a target nucleic acid molecule labeled with [$^{32}$P]-dCTP is generally carried out in a solution of high ionic strength such as 6×SSC at a temperature that is 20-25° C. below the melting temperature, $T_m$, described below. For Southern hybridization experiments where the target DNA molecule on the Southern blot contains 10 ng of DNA or more, hybridization is typically carried out for 6-8 hours using 1-2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule can be estimated from the following equation (Bolton and McCarthy, *Proc. Natl. Acad. Sci. USA* 48:1390, 1962):

$$T_m = 81.5° C. - 16.6(\log_{10}[Na^+]) + 0.41(\% G+C) - 0.63(\% \text{formamide}) - (600/l)$$

where l=the length of the hybrid in base pairs.

This equation is valid for concentrations of Na$^+$ in the range of 0.01 M to 0.4 M, and it is less accurate for calculations of Tm in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies can be made as follows: For this example, it is assumed that the filter will be washed in 0.3×SSC solution following hybridization, thereby: [Na+]=0.045 M; % GC=45%; Formamide concentration=0; l=150 base pairs; Tm=81.5−16.6(log$_{10}$[Na+])+(0.41×45)−(600/150); and so Tm=74.4° C.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques can be utilized and that variations in experimental conditions will necessitate alternative calculations for stringency.

Stringent conditions can be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is selected not to be perfectly complementary to a particular target sequence.

Transcription levels can be quantitated absolutely or relatively. Absolute quantitation can be accomplished by inclusion of known concentrations of one or more target nucleic acids (for example control nucleic acids or with a known amount the target nucleic acids themselves) and referencing the hybridization intensity of unknowns with the known target nucleic acids (for example by generation of a standard curve).

Subject: Living, multicellular vertebrate organisms, a category that includes both human and veterinary subjects for example, mammals, birds and primates.

Transformed: A transformed cell is a cell into which has been introduced a nucleic acid molecule by molecular biology or recombinant DNA techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector can include nucleic acid sequences that permit it to replicate in a host cell, such as an origin of replication. A vector can also include one or more selectable marker genes and other genetic elements known in the art.

The term "wild-type" refers to the customary type of a cell (or molecule) before manipulation or mutation, or the functionally active general form. Thus, a wild-type form of a protein is the form of the protein found in a cell before manipulation or mutation, and a wild-type form of a bacterium is the form of a bacterium that is found in nature or recognized as a representative strain in the laboratory. An isogenic cell line is one that is essentially genetically identical to another, but for one or more specified mutations. The comparison cell, though, need not itself be wild-type.

Although methods and materials similar or equivalent to those described herein can be used in the practice or testing of the present invention, suitable methods and materials are described below. In addition, the materials, methods, and examples are illustrative only and not intended to be limiting.

III. Reducing Acetic Acid Production/Secretion to Achieve High Cell Density Bacterial Cultures The inventors have identified a *Staphylococcus aureus* gene, cidC, that affects the secretion of acetic acid. Disabling this gene, or the pyruvate oxidase encoded thereby, or a plurality of genes (including the cidC gene) in the cidABC operon, either directly or indirectly, allows for growth of bacteria in the presence of glucose without the conversion of acetate to acetic acid and the concomitant accumulation of deleteriously high levels of acetic acid in the culture medium. The result of this is bacterial cell growth to levels far beyond what is achievable using previously available cell strains. The mutant cells also exhibit better longevity, survival and increased cell division (growth) once the cultures have reached stationary phase. Increased growth in stationary phase correlates with the ability of these mutants to metabolize acetate in the culture medium, providing the additional benefit of increased growth efficiency as well as reduced toxicity in culture with elevated glucose. Both the maintenance of higher cell numbers per volume culture in stationary phase, and increased longevity, contribute to the enhanced commercial potential of these mutant bacterial cells, and other bacterial cells comprising similar naturally occurring and/or engineered mutations in the cidC gene, the cidABC operon, or a homolog thereof.

For example, one specific mutant strain of a *Staphylococcus aureus* (which has an engineered knockout mutation in the cidC gene) resulted in the maintenance of density (biomass) in stationary phase at more than twice the levels of the parental strain. Additionally, viability of the cultures was maintained during stationary phase, in contrast to wild type bacteria, which exhibit a decline in biomass and rapid loss in viability once stationary phase has been reached. Thus, over time in stationary phase, the mutant strain exhibits a substantial increase in biomass as compared to a decline in both biomass and viability observed in wild type isogenic cultures. Since this gene is conserved in most bacterial species, including a *B. subtilis*, it is expected that similar results will be seen when cidC or its homolog is disabled in these organisms as well. Table 1 lists non-limiting examples of proteins that are homologous to the *S. aureus* CidC protein, described herein as the prototypical CidC protein. It is specifically contemplated that mutant bacteria comprising a mutant in the gene encoding any one of these CidC homologs would exhibit reduced acetic acid production.

The present disclosure provides bacterial host cells, expression methods and systems for the enhanced bacterial production and secretion of recombinant (e.g., heterologous) or endogenous products, such as proteins. In one embodiment, a bacterial cell is genetically engineered to have a deletion or mutation in a cidABC gene or operon, or homolog thereof, such that the activity of the cidC pyruvate oxidase is reduced, thereby measurably reducing the production of acetic acid by that bacterial cell. In another embodiment, a bacterial cell is genetically engineered to comprise a mutation or deletion in another gene or operon, which influences the cidABC operon such that the activity of the cidC pyruvate oxidase is reduced, thereby measurably reducing the production of acetic acid by that bacterial cell.

IV. Homologs of the Prototypical cidC Gene or cidABC Operon and Proteins Encoded Thereby It is contemplated that the methods described herein can be carried out in any bacterial cell, by inactivating or knocking out the gene encoding the protein homolog of CidC in that cell, or by otherwise inactivating the expression or activity of this protein or another protein of the cidABC operon. The cidABC operon from *S. aureus* is shown in FIG. 1.

As discussed herein, CidC-like proteins and homologs are a group of proteins that bear sequence homology and/or functional homology to the prototypical *S. aureus* CidC protein (SEQ ID NO: 2). Table 1 provides a non-limiting list of representative CidC-like proteins.

TABLE 1

Sequence Alignment for *S. aureus* CidC protein (accession #: AAS89981)

| Accession No. | Definition/Name | Organism | Identities (%) | Positives (%) |
|---|---|---|---|---|
| NP_373063 | hypothetical protein SAV2539 | *Staphylococcus aureus* subsp. *aureus* Mu50 | 99 | 100 |
| NP_375651 | hypothetical protein, similar to pyruvate oxidase | *Staphylococcus aureus* subsp. *aureus* N315 | 99 | 100 |
| D90058 | hypothetical protein SA2327 | *Staphylococcus aureus* | 99 | 100 |
| BAB43630 | SA2327 | *Staphylococcus aureus* subsp. *aureus* N315 | 99 | 100 |
| BAB58701 | pyruvate oxidase | *Staphylococcus aureus* subsp. *aureus* Mu50 | 99 | 100 |
| NP_647277 | ORFID: MW2460~ hypothetical protein, similar to pyruvate oxidase | *Staphylococcus aureus* subsp. *aureus* MW2 | 98 | 99 |
| BAB96325 | MW2460 | *Staphylococcus aureus* subsp. *aureus* MW2 | 98 | 99 |
| NP_765658 | pyruvate oxidase | *Staphylococcus epidermidis* ATCC 12228 | 84 | 93 |
| AAO05745 | pyruvate oxidase | *Staphylococcus epidermidis* ATCC 12228 | 84 | 93 |
| NP_470073 | similar to pyruvate oxidase | *Listeria innocua* Clip11262 | 57 | 73 |
| AB1524 | pyruvate oxidase homolog lin0730 | *Listeria innocua* | 57 | 73 |
| CAC95962 | Lin0730 | *Listeria innocua* | 57 | 73 |
| NP_464249 | similar to pyruvate oxidase | *Listeria monocytogenes* EGD-e | 57 | 72 |
| AB1165 | pyruvate oxidase homolog lmo0722 | *Listeria monocytogenes* | 57 | 72 |
| CAC98800 | Lmo0722 | *Listeria monocytogenes* | 57 | 72 |
| ZP_00232899 | pyruvate oxidase | *Listeria monocytogenes* str. 1/2a F6854 | 57 | 72 |
| EAL07281 | pyruvate oxidase | *Listeria monocytogenes* str. 1/2a F6854 | 57 | 72 |
| YP_013362 | pyruvate oxidase | *Listeria monocytogenes* str. 4b F2365 | 56 | 71 |
| AAT03539 | pyruvate oxidase | *Listeria monocytogenes* str. 4b F2365 | 56 | 71 |
| ZP_00229481 | pyruvate oxidase | *Listeria monocytogenes* str. 4b H7858 | 55 | 71 |
| EAL10741 | pyruvate oxidase | *Listeria monocytogenes* str. 4b H7858 | 55 | 71 |
| NP_694331 | pyruvate oxidase | *Oceanobacillus iheyensis* HTE831 | 46 | 66 |
| BAC15365 | pyruvate oxidase | *Oceanobacillus iheyensis* HTE831 | 46 | 66 |
| NP_388315 | similar to pyruvate oxidase | *Bacillus subtilis* subsp. *subtilis* str. 168 | 46 | 65 |
| G69769 | pyruvate oxidase homolog ydaP | *Bacillus subtilis* | 46 | 65 |
| BAA19271 | similar to pyruvate oxidase and acetolactate synthase | *Bacillus subtilis* | 46 | 65 |
| CAB12241 | ydaP | *Bacillus subtilis* subsp. *subtilis* str. 168 | 46 | 65 |
| ZP_00070215 | COG0028: Thiamine pyrophosphate-requiring enzymes | *Oenococcus oeni* MCW | 46 | 66 |
| NP_978735 | pyruvate oxidase | *Bacillus cereus* ATCC 10987 | 45 | 66 |
| AAS41343 | pyruvate oxidase | *Bacillus cereus* ATCC 10987 | 45 | 66 |
| NP_832091 | pyruvate oxidase | *Bacillus cereus* ATCC 14579 | 45 | 66 |
| AAP09292 | pyruvate oxidase | *Bacillus cereus* ATCC 14579 | 45 | 66 |
| ZP_00070667 | COG0028: Thiamine pyrophosphate-requiring enzymes | *Oenococcus oeni* MCW | 47 | 66 |
| ZP_00070627 | COG0028: Thiamine pyrophosphate-requiring enzymes | *Oenococcus oeni* MCW | 43 | 66 |

TABLE 1-continued

Sequence Alignment for *S. aureus* CidC protein (accession #: AAS89981)

| Accession No. | Definition/Name | Organism | Identities (%) | Positives (%) |
|---|---|---|---|---|
| NP_342490 | acetolactate synthase large subunit homolog (ilvB-3) | *Sulfolobus solfataricus* P2 | 38 | 58 |
| A90253 | hypothetical protein ilvB-3 | *Sulfolobus solfataricus* | 38 | 58 |
| AAK41280 | acetolactate synthase large subunit homolog (ilvB-3) | *Sulfolobus solfataricus* | 38 | 58 |
| NP_786786 | pyruvate oxidase | *Lactobacillus plantarum* WCFS1 | 38 | 58 |
| CAD65664 | pyruvate oxidase | *Lactobacillus plantarum* WCFS1 | 38 | 58 |
| NP_436635 | putative pyruvate oxidase protein | *Sinorhizobium meliloti* 1021 | 35 | 58 |
| G95853 | probable pyruvate oxidase protein | *Sinorhizobium meliloti* (*Rhizobium meliloti*) | 35 | 58 |
| CAC48495 | putative pyruvate oxidase protein | *Sinorhizobium meliloti* (*Rhizobium meliloti*) | 35 | 58 |
| NP_784586 | pyruvate oxidase | *Lactobacillus plantarum* WCFS1 | 34 | 54 |
| CAD63431 | pyruvate oxidase | Lactobacilius plantarum WCFS1 | 34 | 54 |
| NP_344275 | acetolactate synthase large subunit homolog (ilvB-5) | *Sulfolobus solfataricus* P2 | 36 | 58 |
| B90476 | hypothetical protein ilvB-5 | *Sulfolobus solfataricus* | 36 | 58 |
| AAK43065 | acetolactate synthase large subunit homolog (ilvB-5) | *Sulfolobus solfataricus* | 36 | 58 |
| NP_268201 | pyruvate oxidase | *Lactococcus lactis* subsp. *lactis* I11403 | 35 | 57 |
| D86880 | pyruvate oxidase (EC 1.2.3.3) | *Lactococcus lactis* subsp. *lactis* | 35 | 57 |
| AAK06142 | pyruvate oxidase (EC 1.2.3.3) | *Lactococcus lactis* subsp. *lactis* | 35 | 57 |
| NP_394277 | pyruvate dehydrogenase (cytochrome) related protein | *Thermoplasma acidophilum* DSM 1728 | 37 | 57 |
| CAC11945 | pyruvate dehydrogenase (cytochrome) related protein | *Thermoplasma acidophilum* | 37 | 57 |
| ZP_00000927 | COG0028: Thiamine pyrophosphate-requiring enzymes | *Ferroplasma acidarmanus* | 36 | 57 |
| NP_784584 | pyruvate oxidase | *Lactobacillus plantarum* WCFS1 | 35 | 55 |
| CAD63429 | pyruvate oxidase | *Lactobacillus plantarum* WCFS1 | 35 | 55 |
| NP_786788 | pyruvate oxidase | *Lactobacillus plantarum* WCFS1 | 34 | 56 |
| P37063 | Pyruvate oxidase (Pyruvic oxidase) (POX) | *Lactobacillus plantarum* | 34 | 56 |
| CAD65666 | pyruvate oxidase | *Lactobacillus plantarum* WCFS1 | 34 | 56 |
| 1POW_A | Chain A, pyruvate oxidase (E.C.1.2.3.3) (Wild Type) | *Lactobacillus plantarum* | 34 | 56 |
| 1POW_B | Chain B, pyruvate oxidase (E.C.1.2.3.3) (Wild Type) | *Lactobacillus plantarum* | 34 | 56 |
| 1POX_A | Chain A, pyruvate oxidase (E.C.1.2.3.3) mutant with Pro 178 replaced by Ser, Ser 188 replaced by Asn, and Ala 458 replaced by Val (P178s, S188n, A458v) | *Lactobacillus plantarum* | 34 | 56 |

TABLE 1-continued

Sequence Alignment for *S. aureus* CidC protein (accession #: AAS89981)

| Accession No. | Definition/Name | Organism | Identities (%) | Positives (%) |
|---|---|---|---|---|
| 1POX_B | Chain B, pyruvate oxidase (E.C.1.2.3.3) mutant with Pro 178 replaced by Ser, Ser 188 replaced by Asn, and Ala 458 replaced by Val (P178s, S188n, A458v) | *Lactobacillus plantarum* | 34 | 56 |
| ZP_00047198 | COG0028: Thiamine pyrophosphate-requiring enzymes | *Lactobacillus gasseri* | 33 | 55 |
| ZP_00070341 | COG0028: Thiamine pyrophosphate-requiring enzymes | *Oenococcus oeni* MCW | 31 | 50 |
| NP_786039 | pyruvate oxidase | *Lactobacillus plantarum* WCFS1 | 33 | 54 |
| CAD64890 | pyruvate oxidase | *Lactobacillus plantarum* WCFS1 | 33 | 54 |
| NP_286643 | pyruvate oxidase | *Escherichia coli* O157:H7 EDL933 | 33 | 55 |
| NP_308984 | pyruvate oxidase | *Escherichia coli* O157:H7 | 33 | 55 |
| E90748 | pyruvate oxidase | *Escherichia coli* | 33 | 55 |
| A85599 | pyruvate oxidase poxB | *Escherichia coli* | 33 | 55 |
| AAG55253 | pyruvate oxidase | *Escherichia coli* O157:H7 EDL933 | 33 | 55 |
| BAB34380 | pyruvate oxidase | *Escherichia coli* O157:H7 | 33 | 55 |
| NP_415392 | pyruvate oxidase | *Escherichia coli* K12 | 33 | 54 |
| P07003 | Pyruvate dehydrogenase (Pyruvate oxidase) (POX) | *Escherichia coli* | 33 | 54 |
| DEECPC | pyruvate dehydrogenase (cytochrome) (EC 1.2.2.2) | *Escherichia coli* | 33 | 54 |
| CAA27725 | pyruvate oxidase | *Escherichia coli* | 33 | 54 |
| BAA35585 | Pyruvate dehydrogenase (cytochrome) (EC 1.2.2.2) | *Escherichia coli* K12 | 33 | 54 |
| AAC73958 | pyruvate oxidase | *Escherichia coli* K12 | 33 | 54 |
| NP_706752 | pyruvate oxidase | *Shigella flexneri* 2a str. 301 | 33 | 54 |
| NP_836526 | pyruvate oxidase | *Shigella flexneri* 2a str. 2457T | 33 | 54 |
| AAN42459 | pyruvate oxidase | *Shigella flexneri* 2a str. 301 | 33 | 54 |
| AAP16332 | pyruvate oxidase | *Shigella flexneri* 2a str. 2457T | 33 | 54 |
| AAB59106 | pyruvate oxidase | *Escherichia coli* | 32 | 54 |
| NP_455425 | pyruvate dehydrogenase | *Salmonella enterica* subsp. *enterica serovar* Typhi str. CT18 | 32 | 54 |
| NP_805761 | pyruvate dehydrogenase | *Salmonella enterica* subsp. *enterica serovar* Typhi Ty2 | 32 | 54 |
| AG0608 | pyruvate dehydrogenase | *Salmonella enterica* subsp. *enterica serovar* Typhi | 32 | 54 |
| CAD05337 | pyruvate dehydrogenase | *Salmonella enterica* subsp. *enterica serovar* Typhi | 32 | 54 |
| AAO69610 | pyruvate dehydrogenase | *Salmonella enterica* subsp. *enterica serovar* Typhi Ty2 | 32 | 54 |
| NP_459912 | pyruvate dehydrogenase/oxidase | *Salmonella typhimurium* LT2 | 32 | 54 |
| AAL19871 | pyruvate dehydrogenase/oxidase FAD and thiamine PPi cofactors, cytoplasmic in absence of cofactors | *Salmonella typhimurium* LT2 | 32 | 54 |

TABLE 1-continued

Sequence Alignment for *S. aureus* CidC protein (accession #: AAS89981)

| Accession No. | Definition/Name | Organism | Identities (%) | Positives (%) |
|---|---|---|---|---|
| AAB59102 | pyruvate oxidase | *Escherichia coli* | 32 | 54 |
| AAB59108 | pyruvate oxidase | *Escherichia coli* | 32 | 54 |
| AAB59101 | pyruvate oxidase | *Escherichia coli* | 32 | 54 |
| AAB59105 | pyruvate oxidase | *Escherichia coli* | 32 | 54 |
| AAB59109 | pyruvate oxidase | *Escherichia coli* | 32 | 54 |
| NP_631461 | putative pyruvate dehydrogenase (pyruvate oxidase) | *Streptomyces coelicolor* A3(2) | 33 | 54 |
| CAB76331 | putative pyruvate dehydrogenase (pyruvate oxidase) | *Streptomyces coelicolor* A3(2) | 33 | 54 |
| AAB59103 | pyruvate oxidase | *Escherichia coli* | 32 | 54 |
| NP_962189 | hypothetical protein MAP3255 | *Mycobacterium avium* subsp. *paratuberculosis* str. k10 | 33 | 55 |
| AAS05803 | hypothetical protein MAP3255 | *Mycobacterium avium* subsp. *paratuberculosis* str. k10 | 33 | 55 |
| NP_752934 | pyruvate dehydrogenase | *Escherichia coli* CFT073 | 32 | 55 |
| AAN79477 | pyruvate dehydrogenase | *Escherichia coli* CFT073 | 32 | 55 |
| AAB59104 | pyruvate oxidase | *Escherichia coli* | 32 | 54 |
| ZP_00088061 | COG0028: Thiamine pyrophosphate-requiring enzymes | *Pseudomonas fluorescens* PfO-1 | 33 | 54 |
| AAB59107 | pyruvate oxidase | *Escherichia coli* | 32 | 54 |
| NP_404951 | pyruvate dehydrogenase | *Yersinia pestis* CO92 | 32 | 54 |
| NP_670121 | pyruvate oxidase | *Yersinia pestis* KIM | 32 | 54 |
| NP_992603 | pyruvate dehydrogenase | *Yersinia pestis* biovar Medievalis str. 91001 | 32 | 54 |
| AH0165 | pyruvate dehydrogenase | *Yersinia pestis* | 32 | 54 |
| CAC90187 | pyruvate dehydrogenase | *Yersinia pestis* CO92 | 32 | 54 |
| AAM86372 | pyruvate oxidase | *Yersinia pestis* KIM | 32 | 54 |
| AAS61480 | pyruvate dehydrogenase | *Yersinia pestis* biovar Medievalis str. 91001 | 32 | 54 |
| NP_250798 | probable decarboxylase | *Pseudomonas aeruginosa* PAO1 | 33 | 53 |
| ZP_00062558 | COG0028: Thiamine pyrophosphate-requiring enzymes | *Leuconostoc mesenteroides* subsp. *mesenteroides* ATCC 8293 | 30 | 49 |
| NP_823255 | putative pyruvate dehydrogenase | *Streptomyces avermitilis* MA-4680 | 32 | 50 |
| ZP_00123951 | COG0028: Thiamine pyrophosphate-requiring enzymes | *Pseudomonas syringae* pv. *syringae* B728a | 30 | 53 |
| NP_773926 | pyruvate oxidase | *Bradyrhizobium japonicum* USDA 110 | 32 | 50 |
| ZP_00139793 | COG0028: Thiamine pyrophosphate-requiring enzymes | *Pseudomonas aeruginosa* UCBPP-PA14 | 33 | 52 |
| NP_792322 | pyruvate dehydrogenase | *Pseudomonas syringae* pv. tomato str. DC3000 | 30 | 53 |
| NP_630260 | pyruvate dehydrogenase | *Streptomyces coelicolor* A3(2) | 32 | 51 |
| NP_640580 | pyruvate dehydrogenase | *Xanthomonas axonopodis* pv. *citri* str. 306 | 31 | 53 |
| NP_345231 | pyruvate oxidase | *Streptococcus pneumoniae* TIGR4 | 31 | 51 |
| ZP_00092935 | COG0028: Thiamine pyrophosphate-requiring enzymes | *Azotobacter vinelandii* | 27 | 45 |
| AAP87106 | SpxB | *Streptococcus pneumoniae* | 31 | 51 |
| AAB40976 | pyruvate oxidase | *Streptococcus pneumoniae* | 31 | 52 |
| NP_358236 | pyruvate oxidase | *Streptococcus pneumoniae* R6 | 31 | 51 |

TABLE 1-continued

Sequence Alignment for *S. aureus* CidC protein (accession #: AAS89981)

| Accession No. | Definition/Name | Organism | Identities (%) | Positives (%) |
|---|---|---|---|---|
| ZP_00032024 | COG0028: Thiamine pyrophosphate-requiring enzymes | *Burkholderia fungorum* | 23 | 38 |
| AAC69578 | pyruvate oxidase | *Streptococcus oralis* | 30 | 52 |
| ZP_00217943 | COG0028: Thiamine pyrophosphate-requiring enzymes | *Burkholderia cepacia* R18194 | 30 | 50 |
| ZP_00118061 | COG0028: Thiamine pyrophosphate-requiring enzymes | *Cytophaga hutchinsonii* | 31 | 53 |
| NP_635601 | pyruvate dehydrogenase | *Xanthomonas campestris* pv. *campestris* str. ATCC 33913 | 30 | 53 |
| NP_253984 | pyruvate dehydrogenase (cytochrome) | *Pseudomonas aeruginosa* PAO1 | 30 | 54 |
| ZP_00186913 | COG0028: Thiamine pyrophosphate-requiring enzymes | *Rubrobacter xylanophilus* DSM 9941 | 29 | 47 |
| NP_889392 | putative pyruvate dehyrdogenase | *Bordetella bronchiseptica* RB50 | 32 | 51 |
| ZP_00186915 | COG0028: Thiamine pyrophosphate-requiring enzymes | *Rubrobacter xylanophilus* DSM 9941 | 32 | 51 |
| ZP_00225002 | COG0028: Thiamine pyrophosphate-requiring enzymes | *Burkholderia cepacia* R1808 | 30 | 51 |
| NP_965831 | pyruvate oxidase | *Lactobacillus johnsonii* NCC 533 | 31 | 49 |
| NP_884874 | putative pyruvate dehyrdogenase | *Bordetella parapertussis* 12822 | 31 | 50 |
| ZP_00031932 | COG0028: Thiamine pyrophosphate-requiring enzymes | *Burkholderia fungorum* | 28 | 48 |
| ZP_00029290 | COG0028: Thiamine pyrophosphate-requiring enzymes | *Burkholderia fungorum* | 27 | 43 |
| NP_275619 | pyruvate dehydrogenase/ acetolactate synthase | *Methanothermobacter thermautotrophicus* str. Delta H | 25 | 43 |
| ZP_00169346 | COG0028: Thiamine pyrophosphate-requiring enzymes | *Ralstonia eutropha* JMP134 | 30 | 49 |
| ZP_00224498 | COG0028: Thiamine pyrophosphate-requiring enzymes | *Burkholderia cepacia* R1808 | 29 | 49 |
| AAM12352 | pyruvate dehydrogenase | *Bradyrhizobium japonicum* | 31 | 48 |
| NP_601811 | thiamine pyrophosphate-requiring enzyme | *Corynebacterium glutamicum* ATCC 13032 | 32 | 51 |
| NP_127022 | acetolactate synthase, large subunit | *Pyrococcus abyssi* GE5 | 30 | 50 |
| NP_578664 | acetolactate synthase | *Pyrococcus furiosus* DSM 3638 | 29 | 50 |
| NP_682086 | acetohydroxy acid synthase | *Thermosynechococcus elongatus* BP-1 | 32 | 50 |
| NP_613816 | Acetolactate synthase, large subunit | *Methanopyrus kandleri* AV19 | 30 | 49 |
| NP_228358 | acetolactate synthase, large subunit | *Thermotoga maritima* MSB8 | 29 | 48 |
| NP_940284 | Putative pyruvate dehydrogenase | *Corynebacterium diphtheriae* NCTC 13129 | 30 | 50 |
| NP_632694 | Acetolactate synthase large subunit | *Methanosarcina mazei* Go1 | 31 | 47 |
| AAL99356 | acetohydroxy acid synthase large subunit; acetolactate synthase large subunit | *Geobacillus stearothermophilus* | 28 | 49 |
| ZP_00077013 | COG0028: Thiamine pyrophosphate-requiring enzymes | *Methanosarcina barkeri* | 31 | 48 |
| NP_213319 | acetolactate synthase large subunit | *Aquifex aeolicus* VF5 | 32 | 48 |

TABLE 1-continued

Sequence Alignment for *S. aureus* CidC protein (accession #: AAS89981)

| Accession No. | Definition/Name | Organism | Identities (%) | Positives (%) |
|---|---|---|---|---|
| NP_070548 | acetolactate synthase, large subunit (ilvB-1) | *Archaeoglobus fulgidus* DSM 4304 | 30 | 48 |
| NP_276558 | acetolactate synthase, large subunit | *Methanothermobacter thermautotrophicus* str. Delta H | 28 | 48 |
| NP_390709 | acetolactate synthase (acetohydroxy-acid synthase) (large subunit) | *Bacillus subtilis* subsp. *subtilis* str. 168 | 28 | 49 |
| NP_926225 | acetohydroxyacid synthetase large subunit | *Gloeobacter violaceus* PCC 7421 | 31 | 42 |
| NP_765210 | acetolactate synthase large subunit | *Staphylococcus epidermidis* ATCC 12228 | 28 | 47 |
| NP_050806 | acetohydroxyacid synthetase large subunit | chloroplast *Guillardia theta* | 30 | 49 |
| ZP_00022647 | COG0028: Thiamine pyrophosphate-requiring enzymes | *Ralstonia metallidurans* | 29 | 49 |

The CidC-like group of proteins includes glyoxylate carboligases (conserved domain COG3960.1, COG), thiamine pyrophosphate-requiring enzymes (conserved domain COG0028.1, IlvB), pyruvate decarboxylase and related thiamine pyrophosphate-requiring enzymes (conserved domain COG3961.1, COG3961), and acetolactate synthases (conserved domain COG3962.1, COG3962).

In particular, it is contemplated that so-called cidC homologs or cidC-like proteins will comprise one or more conserved thiamine pyrophosphate enzyme (TPP) binding domains. This can include a Thiamine pyrophosphate enzyme, N-terminal TPP binding domain (pfam02776.11, TPP_enzyme_N), a thiamine pyrophosphate enzyme, central domain (pfam00205.11, TPP_enzyme_M), and a Thiamine pyrophosphate enzyme, C-terminal TPP binding domain (pfam02775.11, TPP_enzyme_C), for instance, or at least two such domains, or at least one such domain.

Based on the teaching provided herein, one of ordinary skill in the art is now able to identify a homologous gene or operon in another bacterial cell, for instance by DNA sequence homology to the prototypical cidC gene and protein described herein (SEQ ID NO: 1 and SEQ ID NO: 2, respectively), delete or inactivate that gene or protein, and thereby produce a bacterial cell capable of reduced acetic acid secretion, increased yield (for instance, biomass yield or yield of a heterologous or homologous product of interest) according to the methods provided.

V. Inactivation of a cidABC Operon, Gene, or Homolog Thereof in a Bacterial Cell Producing a bacterial cell with a reduced capacity for production and/or secretion of acetic acid involves, in certain provided embodiments, the replacement and/or inactivation of a naturally occurring gene (such as one or more gene of the cidABC operon (including the cidC gene), or a homolog thereof, or another gene that influences expression or activity of gene(s) of the cidABC operon) from the genome of the bacterial cell. In a preferred embodiment, the mutation is a non-reverting mutation.

One method for mutating such a nucleic acid is to clone the nucleic acid, or part thereof, modify the nucleic acid by site directed or random mutagenesis, and reintroduce the mutated nucleic acid into the cell on a plasmid or other vector. By homologous recombination, the mutated gene can be introduced into the chromosome.

Another method for inactivating the activity of a cidABC operon gene, or a homolog thereof, or another gene that influences expression or activity of gene(s) of the cidABC operon, is through deleting all or part of the chromosomal copy of the gene. In an embodiment, the entire gene is deleted, the deletion occurring in such as way as to make reversion to a functional form of the gene impossible. In another embodiment, a partial deletion is produced. In another embodiment, nucleic acid encoding the catalytic amino acid residues is deleted. Active site mutations can be generated in any CidC-like protein by comparison to known active site mutations in, for instance, the cidC gene or the gene encoding PoxB mutants. Table 2 provides example mutations in PoxB that influence PoxB activity.

TABLE 2

Enzymatic activities of PoxB mutant proteins

| Mutations | PoxB activity (units/mg) | | Activity ratio (Pyr/AKB) |
|---|---|---|---|
| | Pyruvate | AKB | |
| None (wild type) | 11 | 1.6 | 6.9 |
| A467K/M468Q/E469W/M470Q | <0.005 | <0.005 | — |
| M468Q | 9.4 | 1.4 | 6.7 |
| E469W | <0.005 | <0.005 | — |
| L253F/V380A | 0.83 | 1.8 | 0.46 |
| V380S | 0.55 | 0.73 | 0.75 |
| V380G | 0.04 | 0.99 | 0.04 |
| L253F/V466S | <0.005 | <0.005 | — |

Knockout deletion of a naturally occurring target gene, such as a cidC gene or homolog thereof, can be carried out as follows. A cidC gene is isolated (e.g., by amplification of genomic DNA) and inserted into a cloning vector, including a portion of nucleic acid sequence upstream and downstream of the coding sequence of the cidC gene itself. The coding region of the gene is then deleted from the vector in vitro, leaving behind a sufficient amount of the 5' and 3' flanking sequences to provide for homologous recombination with the naturally occurring gene in the bacterial cell. The modified vector is then transformed into the target bacterial cell, where it integrates into the chromosome via homologous recombination in the flanking regions. This method leads to a bacterial strain in which the cidC gene has been deleted. Essentially similar methods can be used to knockout another gene of the cidABC operon (such as the cidA gene), or another gene that influences the expression or activity of one or more genes of this operon (such as the cidR gene), or one or more genes of another operon involved in glucose metabolism (such as an alsSD operon gene). Such methods are well known to those of ordinary skill in the art. Exemplary methods for knocking out bacterial genes, including a cidC gene, are provided in the EXAMPLES section hereinbelow.

In certain embodiments, the vector used in an integration method is a plasmid. A selectable marker optionally can be included in the vector, to allow for simple identification of recombinant microorganisms. As will be appreciated by one of ordinary skill in the art, it is beneficial for the vector to be one that can be selectively integrated into the chromosome, for instance introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants can be selected for growth at high temperatures in the presence of the selectable marker, such as an antibiotic. By way of example, integration mechanisms are described in U.S. Pat. No. 5,733, 723 (Stable gene amplification in chromosomal DNA of prokaryotic microorganisms), which is incorporated herein by reference in its entirety.

Another method of inactivating the naturally occurring gene in a bacterial cell is to mutagenize the chromosomal copy of the gene, for instance by transforming a bacterium of interest with mutagenic oligonucleotides. Alternatively, the chromosomal gene can be replaced with a mutant gene by homologous recombination.

Still other ways of inactivating the cidABC operon involve inhibiting cidABC operon activity at other points in the progression from activation of transcription of the cidABC operon gene, transcription of the cidABC operon gene, post transcriptional message processing, translation of cidABC operon mRNA(s), post translational protein processing, to actual protein activity. Moreover, any agent or system capable of inhibiting cidABC operon activity is contemplated by this disclosure. Such agents include for example, small molecules, drugs, chemicals, compounds, siRNA, ribozymes, antisense oligonucleotides, cidABC operon inhibitory antibodies, cidABC operon inhibitory peptides (such as, cidABC operon peptide fragments), aptamers, or mirror image aptamers.

In some embodiments, the expression of a cidABC operon gene can be inhibited, for example, by targeting or manipulating trans acting activators or silencers or other genetic or protein factors that influence cidABC operon genomnic sequences (for example, CidR). In specific examples, trans acting activators can be prohibited from binding to their cis acting elements in the cidABC operon regulatory sequence, or the binding of trans acting silencers to their cognate sites in the cidABC operon regulatory sequence can be promoted or enhanced. Either event will result in suppression or inhibition of cidABC operon gene expression.

In other embodiments, cidABC operon gene expression, e.g., cidC expression, can be inhibited by interfering with cidABC operon mRNA transcription, processing, or translation, for example, using siRNA, ribozymes or antisense oligonucleotides. Antisense genes or molecules, or related molecules (such as siRNAs), can be engineered into or provided to the bacterium, for instance for expression under a constitutive or inducible promoter, to decrease or prevent expression of cidC or a homolog thereof, or another gene that directly or indirectly interferes with CidC activity. See, for instance, Wagner and Simons, *Annu Rev Microbiol.* 48:713-42, 1994 (incorporated herein by reference), discussing antisense RNA control in bacteria.

The methods disclosed herein therefore contemplate a reduction of cidABC operon activity by introducing into cells an antisense or other interfering construct based on the cidABC operon encoding sequence, including a cDNA sequence from the cidABC operon or flanking regions thereof. For antisense suppression, a nucleotide sequence from a cidABC operon encoding sequence, for example all or a portion of the cidC gene, is arranged in reverse orientation relative to the promoter sequence in the transformation vector.

The introduced sequence need not be a full-length operon or gene, or reverse complement thereof, and need not be exactly homologous to the equivalent sequence found in the cell type to be transformed. Generally, however, where the introduced sequence is of shorter length, a higher degree of homology to the native sequence will be needed for effective antisense suppression. The introduced antisense sequence in the vector can be at least 30 nucleotides in length, and improved antisense suppression will typically be observed as the length of the antisense sequence increases. The length of the antisense sequence in the vector advantageously can be greater than 100 nucleotides. For suppression of the cidC gene itself, for instance, transcription of an antisense construct results in the production of RNA molecules that are the reverse complement of mRNA molecules transcribed from the endogenous cidC gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Also contemplated herein are ribozymes, which are gene targeting agents useful for specific inhibition of gene expression (see, e.g., Zamecnik and Stephenson, *Proc. Natl. Acad. Sci.,* 75:280 284, 1978; Altman, *Proc. Natl. Acad. Sci.,* 90:10898 10900, 1993; Rossi, *Chem. Biol.,* 6:R33 R37, 1999; Trang et al., *Proc. Natl. Acad. Sci.,* 97:5812 5817, 2000; Kohler et al., *J Mol. Biol.* 285:1935-1950, 1999), for example, for the inhibition of cidABC operon gene expression.

The production and use of ribozymes is disclosed in U.S. Pat. No. 4,987,071 to Cech and U.S. Pat. No. 5,543,508 to Haselhoff. Further, RNA enzymes capable of cleaving specific substrate RNA are known in the art, including, for instance, the hairpin (Hampel et al., *Nucleic Acids Res.,* 18:299 304, 1990; Yu et al., *Proc. Natl. Acad. Sci.,* 90:6340 6344, 1993), the hammerhead (Forster and Symons, *Cell,* 50:9 16, 1987; Uhlenbeck, *Nature,* 328:596 600, 1987; Cantor et al., *Proc. Natl. Acad. Sci.,* 90:10932 10936, 1993), the axehead (Branch and Robertson, *Proc. Natl. Acad. Sci.,* 88:10163 10167, 1991), the group I intron (Hampel et al., *Nucleic Acids Res.,* 18:299 304, 1990), and RNase P (Yuan et al., *Proc. Natl. Acad. Sci.,* 89:8006 8010, 1992).

The substrate binding region of RNA enzymes can be modified, using methods well known in the art, to be complementary to a portion of a target RNA, such as cidABC operon mRNA. When delivered to cells expressing the target RNA, the RNA enzyme will then form a complex with and cleave the target RNA. The target specific ribozyme can then dissociate from the cleaved substrate RNA, and repeatedly hybridize to and cleave additional substrate RNA molecules, ultimately inhibiting the expression and activity of any protein encoded by the target RNA.

A ribozyme useful for specifically cleaving cidABC operon mRNA can be designed by selecting, for example, at least 5, at least 10, at least 15, at least 20, at least 30 consecutive nucleotides of cidABC operon mRNA(s) as a substrate for cidABC operon specific ribozyme cleavage.

Oligonucleotides, such as single stranded DNA or RNA oligonucleotides, including, for example, aptamers or antisense oligonucleotides, often are synthesized by chemical methods, such as those implemented on automated oligonucleotide synthesizers. However, oligonucleotides can be made by a variety of other methods, including in vitro recombinant DNA mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

Certain methods disclosed herein contemplate inhibition of cidABC operon polypeptides by, for example, CicC inhibitory antibodies, inhibitory peptides (such as, CidC peptide fragments), aptamers or mirror image aptamers.

Antibodies that inhibit at least one cidABC operon associated activity (such as, for instance, the activity of pyruvate oxidase) can be monoclonal or polyclonal; though, monoclonal inhibitory antibodies are preferred. Monoclonal or polyclonal antibodies can be produced to specifically recognize and bind a cidABC operon protein or a fragment thereof as a first step in producing inhibitory antibodies. Optimally, antibodies raised against these proteins or peptides would specifically detect the protein or peptide with which the antibodies are generated. That is, an antibody generated to a CidC protein or a fragment thereof would recognize and bind the CidC protein/peptide and would not substantially recognize or bind to other proteins found in target cells.

The determination that an antibody specifically detects a target protein is made by any one of a number of standard immunoassay methods; for instance, the Western blotting technique (Sambrook et al., *Molecular Cloning: A Laboratory Manual*, New York: Cold Spring Harbor Laboratory Press, 1989). Antibodies can be screened for those that inhibit a cidABC operon activity.

Monoclonal or polyclonal antibody to the protein can be prepared, for example, using any of the detailed procedures described in Harlow and Lane (*Antibodies, A Laboratory Manual*, New York: Cold Spring Harbor Laboratory Press, 1988). In specific examples, a monoclonal antibody to an epitope of a cidABC operon protein identified can be prepared from murine hybridomas according to the classical method of Kohler and Milstein (*Nature*, 256:495 497, 1975) or derivative methods thereof.

Some method embodiments disclosed herein contemplate polypeptide or peptide agents that measurably reduce at least one biological activity of the cidABC operon, for example peptides that can inhibit a CidC activity. Inhibitory peptides are typically less than about 250 amino acid residues in length, for example, less than about 200 amino acid residues, less than about 150 amino acid residues, less than about 100 amino acid residues, less than about 75 amino acid residues, less than about 50 amino acid residues, less than about 40 amino acid residues, or less than about 30 amino acid residues in length. In some embodiments, inhibitory peptides are dominant negative fragments of a cidABC operon polypeptide.

Specific binding oligonucleotides (such as, aptamers and mirror image aptamers (a.k.a., Spiegelmers™) are oligonucleotides with high affinity and high specificity for a wide variety of target molecules (as reviewed in Jayasena, *Clin. Chem.*, 45(9):1628 1650, 1999), including, for example, polypeptides, peptides, metal ions, organic dyes, drugs, amino acids, cofactors, nucleotides, antibiotics, nucleotide base analogs, and aminoglycosides. In particular examples, a specific binding oligonucleotide binds to a cidABC operon polypeptide and inhibits its activity.

Specific binding oligonucleotides for a particular target are typically selected from a large "library" of unique nucleic acid molecules (often as many as $10^{14}$-$10^{15}$ different compounds or more). Each oligonucleotide molecule in the library contains a unique nucleotide sequence that can, in principle, adopt a unique three dimensional shape. The target specific oligonucleotides are thought to present a surface that is complementary to the target molecule. Chemically modified oligonucleotides can be included in oligonucleotide libraries, for example, 2,6-diaminopyrimidine, xanthine, 2,4-difluorotoluene, 6-methylpurine, 5-(1-pentynyl-2-deoxyuridine), pyrimidines modified with 2' $NH_2$ and 2' F functional groups.

The library of nucleotide sequences is exposed to the target (such as, a protein, small molecule, or supramolecular structure) and allowed to incubate for a period of time. Where a mirror image aptamer (commonly known as a Spiegelmer) is the desired product, the oligonucleotide library is exposed to an enantiomeric form of the natural target. The molecules in the library with weak or no affinity for the target will, on average, remain free in solution while those with some capacity to bind will tend to associate with the target. The specific oligonucleotide/target complexes are then separated from the unbound molecules in the mixture by any of several methods known in the art. Target bound oligonucleotides are separated and amplified using common molecular biology techniques to generate a new library of oligonucleotide molecules that is substantially enriched for those that can bind to the target. The enriched library is used to initiate a new cycle of selection, partitioning and amplification.

After several cycles (for example 5-15 cycles) of the complete process, the library of oligonucleotide molecules is reduced from $10^{14}$-$10^{15}$ or more unique sequences to a small number that bind tightly to the target of interest. Individual oligonucleotide molecules in the mixture are then isolated, and their nucleotide sequences are determined. In most cases, isolated target specific oligonucleotides are further refined to eliminate any nucleotides that do not contribute to target binding or oligonucleotide structure. Target specific oligonucleotides (referred to as aptamers) truncated to their core binding domain typically range in length from 15 to 60 nucleotides.

Once a sequence is identified, the target specific oligonucleotide can be prepared by any known method, including synthetic, recombinant, and purification methods. Any one target specific oligonucleotide can be used alone or in combination with other oligonucleotides specific for the same target. Where an enantiomeric form of the target was combined with the library, as discussed above, the L form of the isolated oligonucleotide sequence(s) is synthesized to generate a mirror-image aptamer, which is specific for the naturally occurring target. Representative methods of making aptamers specific for non DNA binding proteins are described, for example, in U.S. Pat. No. 5,840,867, and in Jayasena, *Clin. Chem.*, 45(9):1628 1650, 1999. cidABC operon specific aptamers or mirror image aptamers can then be screened for those that inhibit cidABC operon activity.

It will be understood by one of ordinary skill that the mutant bacteria described herein optionally can comprise additional deletions or mutations, such as mutations or deletions of proteases (e.g., apr, npr, epr, mpr or others known to those of skill in the art). Such additional mutations in some instances further enhance the production of recombinant protein from the mutant bacterium.

Effective inactivation as intended herein can be readily determined by growing the resultant mutant bacterium and measuring acetic acid production, for instance using a method described herein. Absolute loss of CidC activity is not believed to be necessary, though it is believed that reduction of CidC activity is proportional to acetic acid production. Thus, the less CidC activity in the mutant cell, the lower the acetic acid production in the resultant culture (and therefore the better the growth of the culture, the higher the yields, and so forth). In certain embodiments, a 10% or greater reduction in CidC activity (or the activity of a CidC-like protein) is desired. In other embodiments, the reduction is at least 25%, at least 40%, at least 50%, at least 60%, at least 70%, or more. In particular embodiments, the activity of the CidC-like protein is reduced by at least 80%, at least 90%, at least 95% or more, compared to an isogenic bacterium not mutated as described herein. Particular mutant bacteria will have less than 5% of the wild type activity of CidC (or the ortholog found in that bacterium), less than 3%, or less than 1% of the wild type activity. Specific example methods are provided herein for quantifying acetic acid production from a bacterial culture.

Also contemplated herein are methods for providing mutation of a low passage bacterium relatively soon prior to its introduction into a fermentation system, with the expectation that the acetic acid-reducing mutation will be re-introduced into a low passage strain as necessary to maintain optimal effects during fermentation.

VI. Bacterial Cells

Provided herein are methods for generating and using mutant bacteria, which beneficially produce and/or secrete less acetic acid in the presence of glucose, or another metabolizable carbon source, than do isogenic non-mutant bacteria. The specific bacterium used is not believed to be essential. Thus, although certain examples provided herein are described in the context of *S. aureus* or *E. coli*, other bacteria are contemplated. The bacterium used can be influenced by a number of factors, including for instance whether a cidC homolog has been identified (see, for instance, Table 1); whether the bacterium is well or poorly adapted to production of the product of interest; available laboratory or fermentation facilities; and so forth.

Other bacteria that can be used in methods provided herein include, but are not limited to, members of the genus *Actinomyces, Bifidobacteria, Bacillus, Corynebacterium, Clostridium, Escherichia, Lactobacillus, Lactococcus, Propionibacteria, Pseudomonas, Staphylococcus Streptomyces,* or *Streptoverticillium.* Specifically, the following bacteria are contemplated: *E. coli, S. aureus, Streptomyces coelicolor, B. alcalophilus, B. amyloliquefaciens, B. brevis, B. cereus, B. circulans, B. clausii, B. coagulans, B. firmus, B. lautus, B. lentus, B. licheniformis, B. megaterium, B. nocardia, B. polymyxa, B. popilliae, B. pulvifaciens, B. pumilus, B. sphaericus, B. stearothermophilus, B. subtilis,* and *B. thuringiensis*.

By way of example, bacteria able to produce and secrete proteins encoded by heterologous genes are used extensively for the industrial production of high value-added pharmaceutical proteins. Most commonly used bacteria include *E. coli* and a number of *Bacillus* species, including those listed herein.

In contrast to a gram-negative organism such as *E. coli*, gram-positive bacteria such as *Bacillus* spp. have the capacity to secrete proteins readily into the surrounding medium. Gram-positive microorganisms are therefore commonly used for large-scale industrial fermentation. They are beneficial because they can secrete fermentation products into the culture media. In gram-positive bacteria, secreted proteins are exported across a cell membrane and a cell wall, and then are subsequently released into the medium where they often obtain their native conformation. Members of the group *Bacillus* are therefore beneficially used in methods described herein, and are specifically contemplated as appropriate bacteria that can be mutagenized so as to reduce production and/or secretion of acetic acid.

The genus *Bacillus* is understood to include all members known to those of skill in the art, including but not limited to *B. alcalophilus, B. amyloliquefaciens, B. brevis, B. cereus, B. circulans, B. clausii, B. coagulans, B. firmus, B. lautus, B. lentus, B. licheniformis, B. megaterium, B. nocardia, B. polymyxa, B. popilliae, B. pulvifaciens, B. pumilus, B. sphaericus, B. stearothermophilus, B. subtilis,* or *B. thuringiensis*.

In certain embodiments, it is beneficial for the bacterium from which the mutant is generated to be a low passage isolate. It has been observed, and is recognized by practitioners, that laboratory bacterial strains that have been maintained in culture can accumulate alterations that change their genetics, biochemistry, and physiology. It is contemplated that such accumulated changes can adversely affect the ability of the mutations discussed herein to influence acetic acid production/secretion. Thus, in some laboratory strains, the effects of inactivating a CidC protein may not be as extreme as shown herein for a recently isolated, low passage strain. With this in mind, also contemplated herein are methods for providing mutation of a low passage bacterium soon prior to its introduction into a fermentation system, with the expectation that the acetic acid-reducing mutation will be re-introduced into a low passage strain as necessary to maintain optimal effects during fermentation.

The specific cultivation strategies and conditions permitting production of a product of interest from the mutant bacterial cells described herein can be any of the numerous cultivation protocols known to the skilled person. Similarly, the specific strategy for isolating the product of interest can be any of the numerous isolation protocols known to the skilled person. In spite of this, examples of bacterial cells, cultivation strategies and conditions, and isolation systems are provided.

VII. Expression of Nucleic Acid Molecules and Polypeptides

The expression and purification of proteins can be performed using standard techniques. Examples of such methods are discussed or referenced herein. Partial or full-length cDNA sequences, which encode a desired product protein or fusion protein, can be ligated into bacterial expression vectors. Methods for expressing large amounts of protein from a cloned sequence introduced into *E. coli, S. aureus*, Streptomyces coelicolor, *B. alcalophilus, B. amyloliquefaciens, B. brevis, B. cereus, B. circulans, B. clausii, B. coagulans, B. firmus, B. lautus, B. lentus, B. licheniformis, B. megaterium, B. nocardia, B. polymyxa, B. popilliae, B. pulvifaciens, B. pumilus, B. sphaericus, B. stearothermophilus, B. subtilis*, or *B. thuringiensis*, or other bacterial cells can be utilized for the production and purification of proteins.

Methods and plasmid vectors for producing fusion proteins and intact native proteins in culture are well known in the art, and specific methods are described in Sambrook et al. (In *Molecular Cloning: A Laboratory Manual*, Ch. 17, CSHL, New York, 1989). Such fusion proteins can be made in large amounts and are easy to purify. Native proteins can be produced in bacteria by placing a strong, regulated promoter and an efficient ribosome-binding site upstream of the cloned gene. If low levels of protein are produced, additional steps can be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989).

Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Myriad other suitable expression vector systems will be known to one of ordinary skill in the art.

Expression vectors used in expressing proteins in mutant bacteria provided herein comprise at least one promoter, which promoter is functional in the host cell. In one embodiment, the promoter is the wild-type promoter for the selected protein. In another embodiment, the promoter is heterologous to the protein, but still functional in the host cell. In particular embodiments, the nucleic acid encoding the protein is stably integrated or otherwise stably maintained in the genome of the mutant bacterium.

Optionally, the expression vector contains a multiple cloning site region, which comprises at least one restriction endonuclease site unique to the vector, to facilitate recombinant nucleic acid manipulation. Optionally, the vector also comprises one or more selectable markers (genes capable of expression in the mutant bacterium, and which allow for ease of selection of transformed cells). Examples selectable markers include but are not limited to antibiotics, such as, erythromycin, actinomycin, chloramphenicol and tetracycline.

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

A cDNA sequence (or portions derived from it) or a mini gene (a cDNA with an intron and its own promoter) can be introduced into prokaryotic expression vectors by conventional techniques. These vectors are designed to permit the transcription of the cDNA in prokaryotic cells by providing regulatory sequences that initiate and enhance the transcription of the cDNA and in some embodiments ensure its proper secretion.

The host cell, which can be transfected with the vector of this disclosure, can be selected from the group consisting of *Actinomyces, Bifidobacteria, Bacillus, Corynebacterium, Clostridium, Lactobacillus, Lactococcus, Propionibacteria, Pseudomonas, Staphylococcus Streptomyces*, or *Streptoverticillium* bacteria. Specifically contemplated host cells include *E. coli, S. aureus, Streptomyces coelicolor, B. alcalophilus, B. amyloliquefaciens, B. brevis, B. cereus, B. circulans, B. clausii, B. coagulans, B. firmus, B. lautus, B. lentus, B. licheniformis, B. megaterium, B. nocardia, B. polymyxa, B. popilliae, B. pulvifaciens, B. pumilus, B. sphaericus, B. stearothermophilus, B. subtilis*, or *B. thuringiensis*.

It is specifically contemplated herein that nucleic acids introduced into the provided host cells (mutant bacteria) can be altered so they better fit codon usage bias of the particular organism into which the molecule is to be introduced. See, for instance, Wang et al., *Mol. Biol. Evol.*, 18(5):792-800, 2001. Bacteria particularly have a wide range of GC content and this reflects the types of amino acids they have and the codons they use for these amino acids; codon bias can be a significant obstacle for efficient expression of heterologous genes in, for instance, *E. coli* hosts. Alteration of the codon usage in heterologous expression constructs, in order to make codon usage in the resultant sequence more similar to the host, is well known to those of ordinary skill in the art, and can facilitate high level production of proteins from bacterial cultures. See, for instance, U.S. Pat. No. 6,538,127 (describing changing codon bias to improve protein expression in *E. coli*).

VIII. Transformation

A variety of bacterial cell types can be used for the production of mutant cells as described herein, and thus for use in the product production methods provided. General transformation procedures are well known to those of ordinary skill in the art. Example methods can be found in chapter 9 of Ausubel et al., in *Current Protocols in Molecular Biology*, Greene Publishing Associates and Wiley-Intersciences (1987).

The transfer of DNA into cells is now a conventional technique. In various embodiments, vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors.

In a certain embodiment, the mutant bacterial cell is a gram-positive microorganism. Examples of such microorganism are bacteria of the genus *Bacillus*. In such examples, an expression vector used in methods provided herein is one capable of replicating within the *Bacillus* host cell. Suitable replicating plasmids for *Bacillus* are described in Chapter 3 of *Molecular Biological Methods for Bacillus*, Ed. Harwood and Cutting, John Wiley & Sons, 1990, incorporated herein by reference. Suitable replicating plasmids for *B. subtilis* are listed on page 92, for instance.

In another embodiment, nucleic acid encoding a protein to be expressed in a bacterium of the present invention is stably integrated into the microorganism genome. Several strategies have been described in the literature for the direct cloning of DNA in *Bacillus*. For instance, plasmid marker rescue transformation can be used. This method involves the uptake of a donor plasmid by competent cells carrying a partially homologous resident plasmid (Contente et al., *Plasmid* 2:555-571, 1979; Haima et al., *Mol. Gen. Genet.* 223:185-191, 1990; Weinrauch et al., *J. Bacteriol.* 154(3):1077-1087, 1983; and Weinrauch et al., *J. Bacteriol.* 169(3):1205-1211, 1987). The incoming donor plasmid recombines with the homologous region of the resident "helper" plasmid in a process that mimics chromosomal transformation.

Transformation by protoplast transformation is described for *B. subtilis* in Chang and Cohen (*Mol. Gen. Genet.* 168:111-115, 1979); for *B. megaterium* in Vorobjeva et al. (*FEMS Microbiol. Letters* 7:261-263, 1980); for *B. amyloliquefaciens* in Smith et al. (1986) Appl. and Env. Microbiol. 51:634; for *B. thuringienis* in Fisher et al. (*Arch. Microbiol.* 139:213-217, 1981); and for *B. sphaericus* in McDonald (*J. Gen. Microbiol.* 130:203, 1984). Mann et al. (*Current Microbiol.* 13:131-135, 1986) reported on transformation of *Bacillus* protoplasts and Holubova (*Folia Microbiol.* 30:97, 1985) disclosed methods for introducing DNA into protoplasts using DNA containing liposomes.

IX. Fermentation of Cells to Produce Products of Interest

Methods are known to those of ordinary skill in the art, for growing bacteria cultures to produce products of interest. The method of growth is not important to many embodiments provided herein, though the greatest benefit of the mutant bacterial provided herein will be appreciated when the bacterial culture is grown in the presence of elevated glucose (e.g., 35 mM glucose). In general, the culture media and/or culture conditions (including the type and concentration of metabolizable carbon source) can be such that the microorganisms grow to an adequate density (e.g., which is notably higher than was previously achievable) and produce the desired product efficiently. For large-scale production processes, any method can be used such as those described elsewhere (*Manual of Industrial Microbiology and Biotechnology*, 2$^{nd}$ Edition, Editors: Demain and Davies, ASM Press; and Principles of Fermentation Technology, Stanbury and Whitaker, Pergamon).

Briefly, a large tank (e.g., a 100 gallon, 200 gallon, 500 gallon, or more tank) containing appropriate culture medium with, for example, a glucose carbon source is inoculated with a particular microorganism, particularly a mutant bacterium as provided herein. After inoculation, the microorganisms are incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose. Alternatively, different levels of glucose can be used.

Once transferred, the microorganisms can be incubated to allow for the production of the desired product(s), and/or derivatives thereof. Once produced, any method can be used to isolate the formed product, which methods of course can vary dependent on the desired product. For example, common separation techniques can be used to remove the biomass from the broth, and common isolation procedures (e.g., extraction, distillation, and ion-exchange procedures) can be used to obtain the product(s), and/or derivatives thereof from the microorganism-free broth. Alternatively, the product can be isolated while it is being produced, or it can be isolated from the broth after the product production phase has been terminated.

Contemplated products include, but are not limited to, naturally occurring products obtainable from a bacterium, such as organic acids, vitamins, anti-microbial compounds (such as antibiotics), antigens, surfactants, chemical products and enzymes, as well as products, such as proteins and polypeptides, which are encoded by recombinantly introduced nucleic acid. Also contemplated are engineered products, such as recombinant proteins. Such recombinant protein products can be either homologous or heterologous to the bacterium in which they are produced. Merely by way of example, contemplated recombinant proteins include hormones, enzymes, growth factors, cytokines, antibodies, enzymes (such as a protease, lipase, amylase, pullulanase, cellulase, glucose isomerase, lactase or protein disulfide isomerase), and insecticidal and other toxins.

One of ordinary skill in the art will appreciate that there are myriad methods for monitoring the production of desired products, and for harvesting the product from the bacterial culture. Though selected example methods are provided, these are in no way meant to be limiting.

X. Secretion of Recombinant Proteins

Secretion of a heterologous or homologous protein from a mutant bacterial cell can be detected and quantified using any of a number of well known and art recognized techniques. For instance either polyclonal or monoclonal antibodies specific for the target protein can be used. Examples of antibody-based methods include enzyme-linked immunosorbent assay (ELISA), radioimmunoassay (RIA) and fluorescent activated cell sorting (FACS). These and other assays are described, among other places, in Hampton et al. (1990, *Serological Methods, a Laboratory Manual*, APS Press, St Paul Minn.) and Maddox et al. (*J Exp Med* 158:1211, 1983).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, can be cloned into a vector for the production of an mRNA probe. Vectors useful in such methods are known in the art, many are commercially available, and they optionally can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and US Biochemical Corp (Cleveland Ohio) produce commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins can be produced as shown in U.S. Pat. No. 4,816,567.

XI. Purification of Expressed Proteins

Mutant bacterial cells transformed with polynucleotide sequence(s) encoding heterologous or homologous protein(s) or other products can be cultured under conditions suitable for the expression and recovery of the encoded product from the cell culture medium. The product, such as a protein, produced by a mutant bacterial cell of the present disclosure, in some embodiments will be secreted into the culture medium.

Optionally, the heterologous or homologous polynucleotide sequence can be fused to a nucleotide sequence encoding a polypeptide domain that facilitates purification of target proteins. Such purification facilitating domains include, but are not limited to, metal chelating peptides such as histidine-tryptophan modules that allow purification on immobilized metals (Porath, *Protein Expr Purif* 3:263-281, 1992), protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen, San Diego, Calif.) between the purification domain and the heterologous protein can be used to facilitate purification. Optionally, the purification facilitating domain can be engineered to be readily removable, for instance by protease digestion.

XII. Applications

The present disclosure provides genetically engineered, mutant bacterial cells comprising preferably non-revertable mutations or deletions or other inactivations in a naturally occurring gene of the cidABC operon or a homolog thereof, or a gene that influences the expression or activity of such a gene or homolog, such that activity of the cidC pyruvate oxidase is diminished or deleted altogether. Optionally, such mutant bacterial cells are further genetically engineered to produce a specific product, such as a recombinant protein or polypeptide or any other product, including those examples listed herein.

By inactivation of the cidABC operon, or a gene therein (such as cidC), or a homolog thereof, the resultant bacteria produces and/or secretes less acetic acid to the culture medium in the presence of a metabolizable carbon source, such as glucose (for instance, at least 0.1% glucose or more, such as 0.5% or more, 0.75% or more, 0.8% or more, and so forth, or at least about 5 mM glucose, at least about 10 mM glucose, at least about 15 mM glucose, at least about 20 mM glucose, at least about 25 mM glucose, at least about 30 mM glucose, at least about 35 mM glucose, or more) or comparable or equivalent concentrations of another metabolizable carbon source.

Reduction of acetic acid production/secretion is believed to directly or indirectly enable the resultant mutant bacterial culture to provide measurably higher yields than seen with an isogenic strain not having the mutant. Increased production/yield from the mutant bacterial cells described herein can be measured in a number of ways. These include, for instance, an increase in bacterial biomass relative to a wild type strain (e.g., by maintenance of biomass during stationary phase relative to a decline in biomass observed with the wild type strain during stationary phase), an increase in production of the product, an increase in turbidity, an increase in optical density, or a combination of two or more of these measures.

Thus, mutant cells provided herein grow to substantially higher density (e.g., 10% higher, 20% higher, 30% higher, 40% higher or more) than cells of an isogenic strain not having the mutation. In some embodiments, and at some points during growth of the culture, the mutant bacterial culture can reach cell densities (measured, for instance, by cell number or optical density) that are 50% greater than an isogenic bacterial strain lacking the mutation, or in some instances, 70% greater, 80% greater, 90% greater, or more. In particular embodiments, cell density is at least 100%, 120%, 150%, or 200% higher than seen with an isogenic strain.

Biomass yield also can be measured, for instance wet or dry mass of cells produced under chosen conditions, e.g., at a selected time point during culture. For example, biomass can be measured during stationary phase (for example, after 100 hours post-inoculation) in cultures grown in 35 mM glucose. As discussed above, it is contemplated that a range of increases of biomass production can be achieved. In various embodiments, therefore, biomass produced in a mutant culture, when compared to an isogenic strain not so mutated, will be at least 10% higher, at lest 20% higher, at least 25% higher, at least 30% higher, at least 40% higher, at least 50% higher, at least 80% higher, or higher still. In specific embodiments, the biomass production is 100% higher than in the isogenic strain, 125% higher, 150% higher, 200% higher, or even higher.

The increased cell growth and productivity of the described mutants is also believed to provide a mechanism for increased production of chosen product(s) from the mutant cells. Representative productions that can be produced from these cells are listed herein. Increased yield can be measured, for instance, as an increase in the amount of product or the amount of product harvestable from the culture. In various embodiments, product produced by a mutant culture, when compared to an isogenic strain not so mutated, will be at least 10% higher, at lest 20% higher, at least 25% higher, at least 30% higher, at least 40% higher, at least 50% higher, at least 80% higher, or higher still. In specific embodiments, the product production is 100% higher than in the isogenic strain, 125% higher, 150% higher, 200% higher, or even higher.

Ranges and values provided herein are intended to provide guidance rather than limitation, as will be appreciated by one of ordinary skill.

XIII. Enhancement of Bacterial Cell Death

Carbohydrate metabolism has a dramatic impact on murein hydrolase activity and antibiotic tolerance, and these effects can be attributed, at least in part, to changes in the expression of the cid and lrg operons. Growth of *S. aureus* in the presence of 35 mM glucose results in increased expression of both the cidABC and lrgAB transcripts during mid-exponential growth. Furthermore, extracellular murein hydrolase activity is increased and tolerance to rifampin is decreased in these cultures relative to growth in the absence of glucose. Collectively, these observations indicate that the cid operon positively regulates murein hydrolase activity and tolerance to antibiotics. The effect of excess glucose on cidABC and lrgAB transcription is due, at least in part to, the accumulation of acetic acid in the culture supernatant as a consequence of aerobic glucose metabolism. This effect is regulated by the cidR gene product (CidR), the first LysR-type transcriptional regulator (LTTR) regulator to be described in *S. aureus*. Regulation of cidABC transcription is dependent on the product of the cidR gene, which functions to regulate cidABC expression at the transcriptional level (e.g., in the presence of a coinducer molecule).

The cidABC operon plays an important role in the regulation of bacterial cell death. The cidABC operon is a major component of a bacterial cell death mechanism. For example, the expression of the genes of the cidABC operon enhances killing by antibiotic and bactericidal agents, such as penicillin, vancomycin, rifampicin and mitomycin C.

Without being bound by theory, a bacterial cell death system is likely to be induced by one or more signals common to damaged, nonreplicating cells. Although the details of this signal have not yet been elucidated, the cidABC operon, along with the lrgAB operon, are implicated as molecular components required for translating this signal and enhancing the sensitivity of the bacteria to cell death. For example, the cidA gene product, along with the lrgA gene product, are members of the holin family of proteins, and bear a remarkable functional similarity to the Bax and Bcl proteins of the eukaryotic apoptosis regulatory machinery. Bax and Bcl are also part of a large family of homologous proteins that, in this case, are ubiquitous throughout the eukaryotic world. Similar to bacterial holins, Bax can oligomerize within the mitochondrial membrane to form channels that result in the depolarization of the mitochondria. This leads to the release of cytochrome C oxidase that in turn triggers the caspase cascade, the central effector of apoptosis and the cellular disassembly that ensues. Like antiholins, Bcl can interact with Bax and prevent the oligomerization that leads to membrane depolarization. Although Bax and Bcl do not exhibit sequence similarity to any members of the holin family of proteins, this is not surprising since the holin family is the most diverse functional group of proteins known.

The cidABC operon, as well as the lrgAB operon, is involved as major component of a bacterial cell death mechanism. Strong evidence for this is the recent finding that these genes affect killing by a variety of bactericidal agents. For example, a bacterial strain with a knockout mutation the cid operon is more tolerant than parental cells to several different antibiotics and biocides, including rifampicin and mitomycin C.

In addition to the cidABC transcript from which CidA is produced, the cidABC operon gives rise to a second transcript, cidBC. Expression of cidBC transcripts is dependent on activity of the Sigma B transcription factor, which has recently been implicated in the bacterial response to stress. For example, transcription of cidBC is dramatically enhanced in the SH1000 strain (a Sigma B active strain) at all time points analyzed compared to the isogenic 8325-4 strain that produces inactive Sigma B. Thus, cidBC expression is part of the Sigma B regulon, indicating that it might be part of the cellular stress response.

Based on dilution plating experiments, Sigma B also impacts sensitivity to antibiotics. Using standard dilution plating procedures, wild type bacteria (e.g., SH1000 strain) are more resistant to the killing effects of rifampicin than bacteria that lack the Sigma B factor (e.g., strain 8325-4). Although both strains appeared to lose two log units of viable cell counts in two hrs, the Sigma B positive strain recovers nearly one log unit of cell viability after an additional 4 hours of incubation. In contrast, the Sigma B inactive strain continues to lose viability throughout the entire time course of the experiment.

In contrast, assessment of cell viability using the LIVE/ DEAD BacLite viability stain kit from Molecular Probes, Inc. demonstrated that the SH1000 strain is significantly more sensitive to the killing effects of antibiotics (such as rifampicin), exhibiting a two log loss of viability as early as two hours after exposure the antibiotic. The 8325-4 strain exhibits nearly 100% viability at two hours, and only a very slight decrease in viability at the four and six hour time points. This greater than 1,000-fold difference in viable cell counts determined using the two methods indicates that the 8325-4 strain is viable but nonculturable due to the rifampicin-inactivated RNA polymerase enzymes. It is likely that the dilution plating method could be overestimating the bactericidal activity of antibiotics on the 8325-4 strain because the damaged cells are viable but unable to form a countable colony on a plate. Furthermore, the discrepancy seen between the two viable cell count measurements is likely to be due to the presence of a fully functional bacterial cell death mechanism in the SH1000 strain versus a defective bacterial cell death mechanism in 8325-4.

In combination, these data provide the first evidence that the induction of the cidABC operon and the cell death mediated by this system are part of a global response to stress. Without being bound by theory, it is envisioned that the bacterial population could benefit from this by enabling the surviving cells to more effectively compete for nutrients (both preexisting and those liberated after autolysis) needed to overcome the stress.

Induction of the cid operon in bacteria makes the bacterial cells more susceptible to death-inducing agents. For example, growth of S. aureus in the presence of 35 mM glucose, which induces cidABC expression, causes the cells to be more effectively killed by bactericidal antibiotics such as penicillin, rifampicin and vancomycin. These results indicate that activation of the cid operon is a component of the cell death pathway, and suggests that agents that induce the cid operon can be used to increase bacterial cell death, for example, by enhancing the efficacy of bactericidal agents Thus, the treatment of bacterial infections (including Staphylococcal infections and Anthrax) with antibacterial agents could be improved by administering agents that stimulate cidABC expression in the bacteria (or alternatively, inhibit lrgAB). However, increasing the glucose concentration within the bloodstream to levels that would stimulate cidABC expression (35 mM) would likely have detrimental effects on the subject.

XIV. Methods for Identifying Agents that Increase Sensitivity of Bacterial Cells to Antibiotics Screening methods for identifying agents that increase the sensitivity of bacteria to cell death (and/or that can cause bacterial cell death) are a feature of this disclosure. For example, the methods provided herein can be used to identify agents that increase the susceptibility of bacteria to cell death and that can be more readily tolerated by a subject, such as a human or animal subject undergoing antibiotic therapy, than high levels of glucose.

For example, to identify additional compounds that stimulate cidABC expression, a polynucleotide sequence encoding a reporter is operably linked to a polynucleotide sequence including the transcription regulatory region of the cidABC operon or the lrgAB operon. A "reporter" is a molecule that serves as an indicator of a biological activity. In the context of the present disclosure, a reporter serves as an indicator of transcriptional activity unless otherwise indicated. Typically, a reporter is selected for ease of detection, e.g., by optical means. Common reporters include fluorescent proteins, such as green fluorescent protein (GFP) and numerous variants thereof. Other reporters include proteins with enzymatic activities that convert a fluorogenic or chromogenic substrate into a fluorescent or visible product, or that convert an isotopically labeled substrate into a radioactive product. Examples of such enzymatic reporters include firefly luciferase, chloramphenicol acetyltransferase (CAT), β-glucuronidase and β-galactosidase. A polynucleotide encoding a reporter can be operably linked to a transcription control sequence and introduced into cells. If the transcription control sequence is active in the cell, the reporter will be expressed, and its activity can be detected (qualitatively or quantitatively) using techniques known in the art. Reporters also include selectable markers, the activity of which can be measured as relative resistance or sensitivity to a selection agent, such as an antibiotic. Any of a number of reporters known in the art are suitable in this context.

Figure 24:
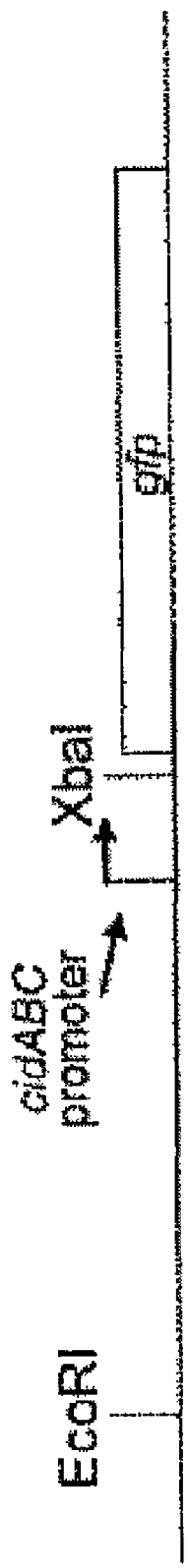
FIG. 24 is a schematic illustration of a reporter construct including approximately 1 kb of the cidA promoter region. Expression of the reporter, green fluorescent protein (GFP) is inducible by agents that regulate expression of the cidABC operon.

In one example, an approximately 1 kb DNA fragment containing the cidABC promoter region was fused to a polynucleotide sequence encoding green fluorescent protein (GFP). An exemplary construct is illustrated in FIG. 24. This construct exhibits glucose-inducible GFP expression and can be used to screen for agents that induce expression of this operon.

Typically, an effect of a test agent on expression of the reporter is detected as a relative increase or a relative decrease in reporter expression. The relative change in expression of the reporter can be a relative increase in expression of a reporter operably linked to the cidABC promoter. A relative increase in expression can be an increase in expression relative to a smaller increase, a constant level or a decrease in expression of the reporter in the control cell. Minor fluctuations in expression in control cells are typically accounted for by experimental error and/or nonspecific effects of cell culture. For example, the relative increase can be an increase in expression of at least 1.5× (times) the level of the reporter in the control cell. Typically the relative increase is at least about 2×, and often at least about 5× or more (for example at least about 10×) greater than a control cell. A relative increase in reporter expression is an indication that the agent increases sensitivity of a bacterial cell to the killing effects of an antibiotic.

Alternatively, the relative change in expression of the reporter can be a relative decrease in expression of a reporter operably linked to the lrgAB promoter. For example, a relative decrease in expression of the test cell as compared to a smaller decrease in expression in the control cell, or a constant level in the test cell compared to an increase in the control cell. Such a decrease in expression of the lrgAB reporter indicates that the test agent increases the sensitivity of a bacterial cell to the killing effects of an antibiotic. For example, a decrease in expression is usually a decrease of at least 1.5× (that is, 1.5× less than) the expression of a control cell. Typically the decrease is at least about 2×, or at least about 5× the level of a control. In some cases the decrease is at least about 10× or more, compared to the control cell.

Typically reporter assays involve detecting expression of the reporter at the level of the translated product either by quantitatively measuring reporter protein or by quantifying activity of the reporter. However, it is also possible to evaluate expression of the reporter at the level of transcription. Numerous methods for quantitatively evaluating RNA expression are known in the art, and include, for example, northern blotting, dot and/or slot blotting, quantitative PCR methods, transcription assays, and the like. Any of these methods can be employed in the context of the methods disclosed herein to evaluate expression of a reporter. Optionally, such RNA analyses can be performed in high throughput formats, including multiwell plates, microarrays and/or microfluidic formats.

If desired reporter protein can be detected using, for example western blotting or antibody arrays that are suitable for quantitatively measuring protein levels. More commonly, reporter expression is evaluated by measuring an activity of the reporter, such as fluorescence emission by the reporter or enzymatic activity, e.g., enzymatic conversion of a chromogenic or fluorogenic substrate into a colored or fluorescent product. As discussed above, reporters are typically readily detectable or assayable proteins. Numerous reporter genes, including those described above are commonly known, and methods of their use are standard in the art.

In particular embodiments, it is desirable to employ a reporter that is optically detectable, either directly or indirectly via detection of a visible or fluorescent product. Most commonly, the reporter is optically detected by detecting the reporter itself (e.g., GFP) or by detecting an optically detectable product formed as a result of an enzymatic activity of a reporter (such as luciferase). Exemplary protocols are provided, for example, in the manufacturer's directions for human placental alkaline phosphatase (SEAP), luciferase, or enhance green fluorescent protein (EGPF) available from BD Biosciences (Clontech); or galactosidase/luciferase, luciferase, or galactosidase available from Applied Biosystems (Foster City, Calif., USA); and available from various other commercial manufacturers of reporter gene products, or otherwise known in the art. For example, expression of GFPs can be detected by flow cytometry as described in, e.g., U.S. Pat. No. 5,938,738; Ropp et al., *Cytometry,* 21:309-317, 1995). Other suitable detection methods include a variety of multiwell plate fluorescence detection devices, e.g., the CYTOFLUOR 4000® multiwell plate reader from Applied Biosciences, and the detection of fluorescent cells using a microfluidic device (such as the 2100 Bioanalyzer from Agilent, Palo Alto) according to Manufacturer's instructions and protocols.

Agents that increase the sensitivity of a bacterial cell to killing by antibiotics can be identified by contacting cells containing the cidABC reporter construct with members of a library of compounds, such as a small molecule or other chemical compound library. Following exposure of the cell with a library member, expression of GFP (or another reporter) can be detected. An increase in the level of GFP indicates that the agent induces cid expression and enhances cell death. Alternatively, such agents can be identified by contacting cells containing the lrgAB reporter construct with members of a library of compounds, and detecting a decrease in GFP expression. In some cases, the library is screened with cells that include the cidABC reporter construct and with cells that contain the lrgAB reporter construct. The two constructs can be incorporated into different cells, or can be within the same cells. When the two reporter constructs are incorporated into the same cell(s), they typically include different reporters, e.g., GFP and luciferase, or two different variants of GFP, e.g., with distinguishable emission spectra. Thus, agents that increase the sensitivity of bacteria to cell death (for example, cell death induced by antibiotics) can be identified by screening cells that include a cidABC reporter construct and detecting an increase in reporter expression, or by screening cells that include a lrgAB reporter construct and detecting a decrease in reporter expression, or by screening on or more cells that include both the cidABC reporter construct and the lrgAB reporter construct, and detecting agents that increase and/or decrease expression of the reporters operably linked to the cidABC and lrgAB promoters, respectively. Additional assays can be performed to identify those agents that most effectively sensitize the bacteria to killing by a variety of bactericidal agents.

While methods for screening libraries are most commonly directed to the screening of libraries of chemical compositions, e.g., small molecules, the agents to be screened can include any compounds or compositions, including both inorganic and organic chemical compounds, as well as biological molecules, such as nucleic acid (for example, siRNA, antisense molecules, ribozymes) or polypeptides. These methods disclosed herein are particularly favorably employed to identify compounds that increase the efficacy of existing antibiotics. Such compounds are useful as an adjunct to or in combination with administration of antibiotics to, for example: 1) reduce the number of doses required to treat a bacterial infection; 2) reduce the risk that the bacteria could acquire or evolve to antibiotic resistance; and 3) reduce the cost of treating these infections by reducing complications due to resistance and by decreasing the number of doses.

For example, the methods disclosed herein are useful for screening libraries of agents to identify compounds that increase the sensitivity of bacterial cells to antibiotic induced killing. Such agents include, but are not limited to, natural products, chemical and biochemical compositions (such as peptides, polypeptides, and nucleic acids). For example, extracts and/or isolated or purified natural products derived from any of a myriad of sources, e.g., soil, water, microorganisms, plants, animals, can be evaluated for their ability to increase the sensitivity of bacterial cells to killing by antibiotics according to the methods disclosed herein. Similarly, isolated, synthetic peptides such as, for example, soluble peptides, including but not limited to members of random peptide libraries (see, e.g., Lam et al., Nature, 354:82-84, 1991; Houghten et al., Nature, 354:84-86, 1991), and combinatorial chemistry-derived molecular library, for instance, consisting of D and/or L configuration amino acids, or phosphopeptides (including, but not limited to, members of random or partially degenerate, directed phosphopeptide libraries; see, e.g., Songyang et al., Cell, 72:767-778, 1993) can be agents that increase the sensitivity of bacterial cells to antibiotic induced cell death. In addition, polypeptides, including but not limited to dominant negative polypeptides, fusion polypeptides, and binding proteins (including antibodies, such as, polyclonal, monoclonal, humanized, anti-idiotypic, chimeric or single chain antibodies, and Fab, F(ab')$_2$ and Fab expression library fragments, and epitope-binding fragments thereof), are all favorably evaluated using the methods disclosed herein. Furthermore, small organic or inorganic molecules (such as members of chemical combinatorial libraries) are also favorably evaluated as potential agents to enhance the killing properties of antibiotics.

Libraries useful for the disclosed screening methods are produced by methods including, but not limited to, spatially arrayed multipin peptide synthesis (Geysen et al., Proc Natl Acad Sci USA, 81:3998 4002, 1984), "tea bag" peptide synthesis (Houghten, Proc Natl Acad Sci USA, 82:5131 5135, 1985), phage display (Scott and Smith, Science, 249:386-390, 1990), spot or disc synthesis (Dittrich et al., Bioorg. Med. Chem. Lett., 8:2351 2356, 1998), or split and mix solid phase synthesis on beads (Furka et al., Int. J. Pept. Protein Res., 37:487 493, 1997; Lam et al., Chem. Rev., 97:411-448, 1997).

Typically, but not necessarily, high throughput screening methods involve providing a library containing a large number of potential modulators (e.g., specific binding compounds). For example, a library usually includes more than 100 members or compounds. More commonly, a library includes more than about 1000 members. Frequently, a library for use in the methods described herein includes more than about 5000 members, such as more than about 10,000 members. In some cases, the library includes more than about 50,000, more than about 100,000 or even more than about 500,000 or more than about 1 million different members. Such libraries are then screened in one or more assays, as described herein, to identify those library members (such as, chemical species or subclasses) that display a desired characteristic activity (such as, increasing transcription of the cidABC operon, or decreasing transcription of the lrgAB operon). The compounds thus identified can serve as conventional "lead compounds" or can, themselves, be used as potential or actual therapeutics.

A combinatorial library is a collection of diverse chemical (or biochemical) compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res., 37:487-493, 1991; Houghton et al., Nature, 354:84-88, 1991). Other chemistries for generating chemical diversity libraries can also be used. Such chemistries include, but are not limited to: peptides (e.g., PCT Publication No. WO 91/19735), encoded peptides (e.g., PCT Publication No. WO 93/20242), random bio-oligomers (e.g., PCT Publication No. WO 92/00091), vinylogous polypeptides (Hagihara et al., J. Am. Chem. Soc., 114:6568, 1991), nonpeptidal peptidomimetics with glucose scaffolding (Hirshmann et al., J. Am. Chem. Soc., 114:9217-9218, 1992), analogous organic syntheses of small compound libraries (Chen et al., J. Am. Chem. Soc., 116:2661, 1994), oligocarbamates (Cho et al., Science, 261:1303, 1993), and/or peptidyl phosphonates (Campbell et al., J. Org. Chem., 59:658, 1994), nucleic acid libraries (see Sambrook et al., Molecular Cloning, A Laboratory Manual, Cold Springs Harbor Press, N.Y., 1989; and Ausubel et al., Current Protocols in Molecular Biology, Green Publishing Associates and Wiley Interscience, 2001), peptide nucleic acid libraries (see, e.g., U.S. Pat. No. 5,539,083), antibody libraries (see, e.g., Vaughn et al., Nat. Biotechnol., 14:309-314, 1996; and PCT/US96/10287), carbohydrate libraries (see, e.g., Liang et al., Science, 274:1520-1522, 1996; and U.S. Pat. No. 5,593,853), small organic molecule libraries, and the like.

Devices for the preparation of combinatorial libraries are commercially available (see, e.g., 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

Computer modeling and searching technologies also permit identification of compounds, or the improvement of already identified compounds that can specifically bind to or indirectly modulate gene expression via the cidABC or lrgAB promoter. Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al., Acta Pharmaceutical Fennica, 97:159-166, 1988; Ripka, New Scientist, 54-57, 1988; McKinaly and Rossmann, Ann. Rev. Pharmacol. Toxicol., 29:111-122, 1989; Perry and Davies, *OSAR: Quantitative Structure-Activity Relationships in Drug Design*, Alan R. Liss, Inc., 1989, pp. 189-193; Lewis and Dean, *Proc. R. Soc. Lond.,* 236:125-140 and 141-162, 1989; and, with respect to a model receptor for nucleic acid components, Askew et al., *J. Am. Chem. Soc.,* 111:1082-1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, and are thus useful for modeling interactions with factors that bind to the cidABC and/or lrgAB promoters, they can be adapted to design of drugs that bind specifically to DNA or RNA, such as the agents that bind directly to the cidABC or lrgAB promoters.

Screening methods can include, but are not limited to, methods employing solid phase, liquid phase, cell-based or virtual (in silico) screening assays. The following assays relate to identifying compounds that interact with (e.g., specifically bind to) a factor that binds to the cidABC and/or lrgAB promoter, compounds that interfere with a protein-protein interaction involving a factor that binds to such a promoter, and to compounds which modulate gene expression via binding to these promoters directly. Compounds identified via assays such as those described herein are likely to be useful as agents that increase the sensitivity of bacterial cells, e.g., pathogenic bacterial cells, to killing by antibiotics. Thus, when administered in combination with antibiotics increase their therapeutic efficacy with respect to treating a bacterial infection.

EXAMPLES

The following examples are provided to illustrate certain particular features and/or embodiments. These examples should not be construed to limit the invention to the particular features or embodiments described. Each of the publications cited herein is incorporated by reference in its entirety.

Example 1

Acetic Acid Induces Expression of the *Staphylococcus aureus* cidABC and lrgAB Murein Hydrolase Regulator Operons Responsiveness of cidABC and lrgAB to growth in glucose was evaluated by norther blot analysis and biochemical assays. Expression of both cidABC and lrgAB was stimulated by growth in the presence of 35 mM glucose. This effect was found to be dependent on the accumulation of acetic acid in the culture supernatant, a consequence of glucose metabolism. Furthermore, extracellular murein hydrolase activity and rifampin sensitivity of UAMS-1 (a previously-characterized low-passage clinical isolate) was greatly enhanced when grown in the presence of 35 mM glucose. A variant of UAMS-1 with a mutation in the cidA gene displayed a complete loss of extracellular murein hydrolase activity as well as decreased sensitivity to rifampin, a phenotype very similar to the previously characterized cidA mutant of RN6390 (Rice et al., *J. Bacteriol.* 185: 2635-2643, 2003). However, unlike UAMS-1, decreased murein hydrolase activity was unaffected when the cidA mutant was cultured with 35 mM glucose, illustrating the importance of the cidA gene in the regulation of murein hydrolase activity. These results demonstrate that expression of both cidABC and lrgAB, as well as murein hydrolase activity and antibiotic sensitivity, are responsive to by-products of glucose metabolism.

Materials and Methods:

Bacterial strains and growth conditions. The *S. aureus* UAMS-1 strain used throughout this study was a recently-isolated osteomyelitis strain (Gillaspy et al., *Infect Immun* 63(9): 3373-3380, 1995). *S. aureus* KB1050 (cidA::Erm; $Em^R$) is a cidA mutant derivative of UAMS-1. All *S. aureus* strains were grown in either tryptic soy broth (TSB; Difco Laboratories, Detroit, Mich.) or NZY broth (3% [wt/vol] N-Z Amine A [Sigma Chemical Co., St. Louis, Mo.], 1% [wt/vol] yeast extract [Fisher Scientific, Fair Lawn, N.J.], adjusted to pH 7.5 unless otherwise indicated), and supplemented as necessary with 1.5% (wt/vol) granulated agar (Difco). Where specified below, NZY cultures were adjusted to pH 5.0 with either HCl or glacial acetic acid (HAc), and/or were supplemented with one of the following: glucose, potassium acetate (KAc), HAc. All of these supplements were stored as filter-sterilized stock solutions, and were diluted to the appropriate concentration in the culture medium at the time of inoculation. All of the cultures were grown in Erlenmeyer flasks at 37° C. with shaking at 250 RPM in a volume that equaled 8%-10% of the flask volume. All antibiotics were purchased from either Sigma Chemical Co. or Fisher Scientific and were used at the following concentrations: erythromycin (Em; 5 $\mu g \cdot ml^{-1}$), tetracycline (Tc; 5 $\mu g \cdot ml^{-1}$).

Allele replacement of the cidA gene in UAMS-1. KB1050, a cidA mutant derivative of UAMS-1, was created by using the plasmid pBF650 (described by Rice et al., *J. Bacteriol.* 185: 2635-2643, 2003). pBF650 was introduced into bacterial cells by electroporation (Schenk & Laddaga, *EMS Microbiol Lett* 73: 133-138, 1992) into UAMS-1. This was followed by growth at the non-permissive temperature (46° C.) in the presence of 2 $\mu g \cdot ml^{-1}$ erythromycin to select for cells in which the plasmid had integrated into the chromosome via homologous recombination. To promote a second recombination event, a single colony was inoculated into antibiotic-free TSB medium and grown at 30° C. for 5 days, with 1:1,000 dilutions into fresh antibiotic-free medium each day. After the fifth day, dilutions of the culture were spread on TSA medium to yield isolated colonies, which were subsequently screened for $Em^r$ and $Tc^s$. Verification that 142 bp (nt 2626675 to 2626533 of the *S. aureus* strain 8325 genome) had been deleted from the 5' end of the cidA gene was carried out by PCR amplification and Southern blot analyses.

Measurement of growth, pH, and acetic acid concentrations. Growth of all *S. aureus* cultures was monitored by measuring the optical density at 600 um ($O.D._{600}$) using an UltraSpec 4000 spectrophotometer (Pharracia-Biotech, Piscataway, N.J.). To harvest culture supernatants, 2-3 mil of each culture were centrifuged at 3,000 RPM for 15 minutes, and the culture supernatants were decanted into sterile test tubes. The pH of 1.5 ml aliquots of each supernatant was measured with an Accumet Basic pH meter (Fisher Scientific, Pittsburgh, Pa.). 100 µl aliquots of each supernatant were also stored at −80° C. until used for quantifying acetic acid concentrations using the acetic acid detection kit purchased from R-BioPharm, Inc. (Marshall, Mich.), following the manufacturer's protocols.

RNA isolation and Northern blot analysis. For all RNA isolations, overnight *S. aureus* cultures were used to inoculate Erlenmeyer flasks containing an 8%-10% volume of NZY to an initial $O.D._{600}$ of 0.1. The cultures were then grown for the period of time indicated for each experiment, and cells were harvested for RNA isolation by centrifugation. Total RNA was isolated using the TRIZOL reagent (Invitrogen Life Technologies, Carlsbad, Calif.) and the FASTPREP cell disruptor (QBiogene, Inc., Carlsbad, Calif.) as previously described (e.g., in Papakyriacou et al., *J. Infect. Dis.* 181:179, 2001; Cheung et al., *Anal. Biochem.* 222(2): 511-514, 1994; Rice et al., *Infect. Immun.* 69(1): 159-169, 2001). For Northern blot analysis, 5-10 µg of each RNA sample as indicated for each experiment was subjected to electrophoresis through a 1% (wt/vol) agarose gel containing 0.66 M formaldehyde and morpholine propane sulfonic (MOPS) running buffer (20 mM MOPS, 10 mM sodium acetate, 2 mM EDTA, pH 7.0). The RNA samples were subsequently transferred to nylon membrane (Micron Separations Inc., Westboro, Mass.) by overnight capillary transfer in 20×SSC (0.3 M $Na_3$-citrate, 3.0 M NaCl, pH 7.0), and fixed to the membrane by baking at 80° C. for at least 2 hours. Hybridization of the immobilized RNA with digoxygenin (DIG)-labeled DNA probes and subsequent washing and detection steps were performed using buffers and reagents of the DIG system (Roche Applied Science, Indianapolis, Ind.), following the manufacturer's recommendations for Northern blot analysis. DIG-labeled DNA probes were synthesized using the PCR-based DIG Probe Synthesis Kit (Roche) and the primer pairs cidA1-F-cidA1-R, cidB1-F-cidB1-R, and lrgA1-F-lrgA1-R, to synthesize cidA, cidB, and lrgA specific probes, respectively. The sequences of these primers are:

```
cidA1-F   5'-ccccatatgCACAAAGTCCAATTA-3';        (SEQ ID NO: 3)

cidA1-R   5'-cccctcgagTTCATAAGCGTCTACACC-3';    (SEQ ID NO: 4)

cidB1-F   5'-TGATTTGTTGACTGTCGTT-3';            (SEQ ID NO: 5)

cidB1-R   5'-TCATGTGACACTTCGATACC-3';           (SEQ ID NO: 6)

cidC2-F   5'-AGGTACAGCAACAGTTTGGT-3';           (SEQ ID NO: 7)

cidC2-R   5'-CTTGTGCTAGTGCCTCTTCT-3';           (SEQ ID NO: 8)

lrgA1-F   5'-ccccatatgGTCGTGAAACAACAAAAAGACGC-3'; (SEQ ID NO: 9)
and lrgA1-R   5'-cccctcgagATCATGAGCTTGTGCCTCCTC-3'. (SEQ ID NO: 10)
```

Murein hydrolase assays. Overnight *S. aureus* cultures were used to inoculate Erlenmeyer flasks containing an 8% volume of NZY to an initial $O.D._{600}$ of 0.1, and grown for 16 hours at 37° C. and 250 RPM. The culture supernatant (containing extracellular murein hydrolases) was harvested by centrifugation for 20 minutes and 1900×g, and concentrated approximately 6-fold in a Centricon-3 concentrator (Millipore, Bedford, Mass.). Protein concentrations of the concentrated extracellular proteins were determined using the Bradford Assay (Bio-Rad Laboratories, Hercules, Calif.), according to the manufacturer's recommended protocols. Quantitative cell wall hydrolysis assays were performed according to established procedures (see, e.g., Groicher et al., *J. Bacteriol.* 182: 1794-1801, 2000), except that 50 µg of concentrated extracellular proteins were used to lyse a suspension of 1 mg·$ml^{-1}$ *Micrococcus luteus* cell walls (Sigma), and the turbidity of the samples were determined by measuring their optical densities at 580 nm ($O.D._{580}$). Zymogram analysis of extracellular murein hydrolase activity was performed as described previously (Groicher et al., *J. Bacteriol.* 182: 1794-1801, 2000).

Rifampin sensitivity assays. Rifampin-induced killing of UAMS-1 and KB1050 were assessed by dilution plating (see, e.g., Groicher et al., *J. Bacteriol.* 182: 1794-1801, 2000; Rice et al., *J. Bacteriol.* 185: 2635-2643, 2003). Briefly, overnight *S. aureus* cultures were each diluted to an $O.D._{600}$ of 0.1 in 125 ml Erlenmeyer flasks containing 10 ml NZY broth, both in the presence and absence of 35 mM glucose. The cultures were then grown for 4 hours at 37° C. and 250 RPM prior to the addition of 2 µg·$ml^{-1}$ rifampin, and cell viability was monitored by dilution plating.

Light microscopy. Overnight cultures of UAMS-1 and KB1050 were each diluted to an $O.D._{600}$ of 0.1 in 125 ml Erlenmeyer flasks containing 10 ml NZY broth, both in the presence and absence of 35 mM glucose. The cultures were grown for eight hours at 37° C. and 250 RPM, and samples were harvested for light microscopy analysis. For preparation of microscope slides, a smear of each culture was heat-fixed to a standard glass slide, and stained with Gram's Crystal Violet for 1 minute, followed by destaining with $ddH_2O$. Slides of each culture were prepared in duplicate. The slides were then viewed under oil at 1000× magnification with an Olympus BX41 microscope (Olympus America, Inc., Melville, N.Y.) and images representative of each culture were captured using Magnafire SP (version 2.1B) software.

Figure 2:
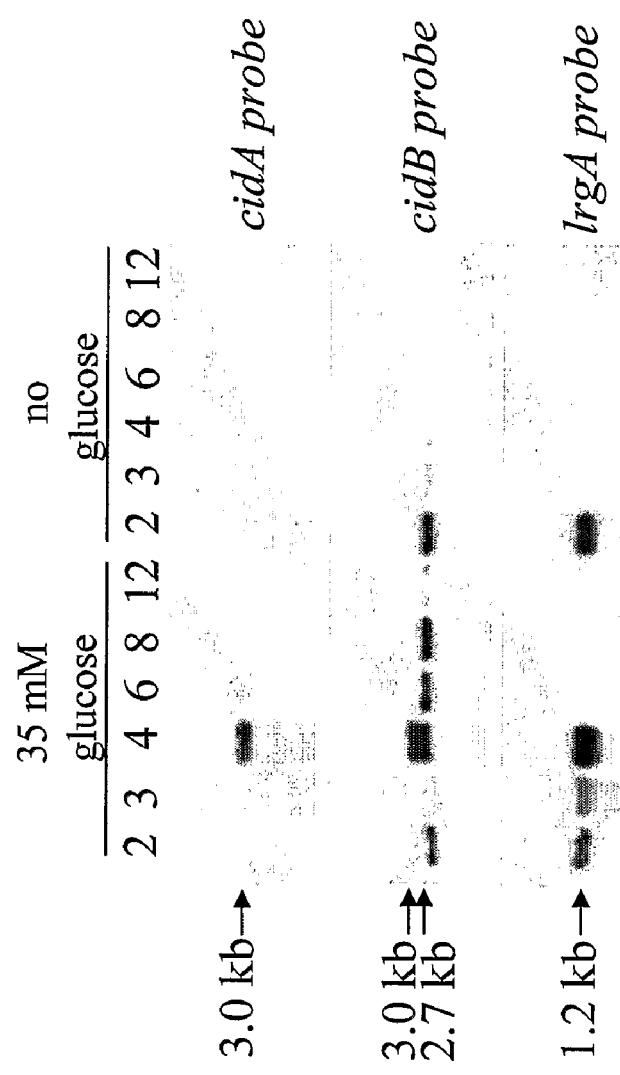
FIG. 2 is a Northern blot analysis of cid and lrg transcription in *S. aureus* UAMS-1. Total cellular RNA was isolated from UAMS-1 cultured in either the presence of 35 mM glucose or in the absence of glucose at 2, 3, 4, 6, 8, and 12 hours post-inoculum (as indicated above each lane of the blot). 10 μg of each RNA sample was separated through a 1% (wt/vol) agarose-formaldehyde gel, transferred to a nylon membrane, and hybridized to cidA-, cidB-, and lrgA-specific DIG-labeled probes. The sizes of each transcript were determined by comparison to an RNA ladder (Invitrogen) run on the same gel.

Results:

Transcription of cidABC and lrgAB are induced by glucose. To determine if cidABC transcription was induced by growth in the presence of excess glucose in *S. aureus*, a Northern blot analysis was performed on RNA samples from cultures of the clinical isolate UAMS-1 grown in both the presence and absence of 35 mM glucose (FIG. 2). Transcription of cidABC was not detectable by Northern blot analysis at any of the time points examined in the control (no-glucose) culture. However, in cultures containing glucose, cidABC was dramatically induced at 4 hours growth (late exponential phase), and declined to undetectable levels by 8 hours. A similar pattern of increased lrgAB expression was observed: lrgAB transcription was increased at 3 hours growth in the presence of glucose and disappeared after 4 hours, whereas the lrgAB transcript was not detected at these time points in the control culture. The 2.7-kb cidBC transcript also appeared to somewhat upregulated when UAMS-1 was grown in the presence of 35 mM glucose, but this effect was not nearly as dramatic as that observed for cidABC and lrgAB transcription. Further analysis revealed that increased cidABC and lrgAB transcription occurred in media containing a minimum of 20 mM glucose, indicating that this concentration represents a threshold level that results in high-level cidABC and lrgAB transcription.

Figure 3A:
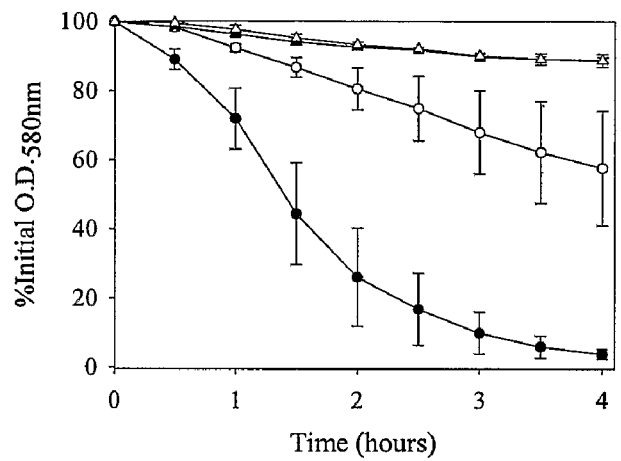
FIGS. 3A and B illustrates the results of a typical quantitative cell wall hydrolysis assay (FIG. 3A) and zymogram analysis (FIG. 3B) of extracellular murein hydrolase activities of UAMS-1 and KB1050.
Figure 3B:
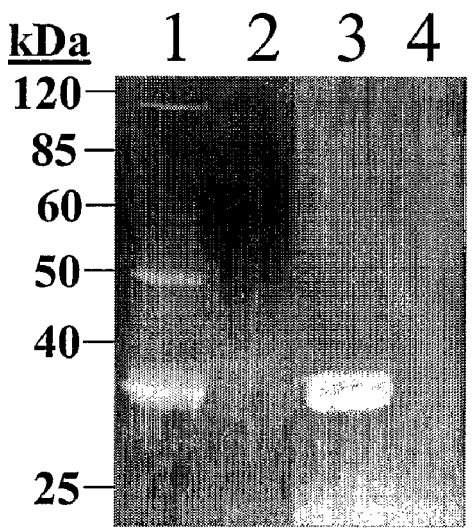
FIG. 3B: 15 μg of extracellular proteins, isolated from 16-hour cultures of UAMS-1 and KB1050 grown in either the presence of 35 mM glucose or in the absence of glucose, were separated in an SDS-PAGE gel containing 1 mg·ml$^{-1}$ *M. luteus* cell walls, followed by an overnight incubation at 37° C. in a buffer containing Triton-X 100 and staining with methylene blue. This zymogram is representative of results obtained from at least 3 independent experiments. The migration of molecular mass markers (in kilodaltons) are indicated to the left of the gel. Lane 1, UAMS-1 (no glucose); Lane 2, KB1050 (no glucose); Lane 3, UAMS-1 (35 mM glucose); Lane 4, KB1050 (35 mM glucose).

Effect of glucose on extracellular murein hydrolase activity. Mutation of cidA in the laboratory strain RN6390 resulted in decreased extracellular murein hydrolase activity (Rice et al., *J. Bacteriol.* 185: 2635-2643, 2003), suggesting that the cidA gene product acts as a positive regulator of murein hydrolase activity. Since cidABC expression is increased in cultures containing excess glucose, extracellular murein hydrolase activity was evaluated during growth in the presence of 35 mM glucose. It was predicted that the phenotype of decreased murein hydrolase activity associated with a cidA mutant would not be affected by growth in the presence of 35 mM glucose. Therefore, the cidA mutation was transferred to the clinical isolate UAMS-1, and both isogenic strains were subsequently assessed for extracellular murein hydrolase activity when grown in both the presence and absence of 35 mM glucose (FIG. 3A). As predicted, the extracellular murein hydrolase activity of UAMS-1 was dramatically increased when cultured in the presence of 35mM glucose, compared to the UAMS-1 no-glucose control (FIG. 3A). By the end of the cell wall hydrolysis assay (4 hours), the no-glucose NZY UAMS-1 sample had solubilized approximately 40% of the *M. luteus* cell walls, whereas the 35 mM glucose sample had solubilized nearly 100% of the cell walls. By zymogram analysis, 34-kDa, 50-kDa and 110-kDa extracellular murein hydrolases were observed in the culture supernatant of UAMS-1 grown in the absence of glucose (FIG. 3B, lane 1). When UAMS-1 was grown in the presence of 35 mM glucose, the 50-kDa and 110-kDa murein hydrolases disappeared, and the 34-kDa murein hydrolase appeared to be more intense (FIG. 3B, lane 3) relative to its counterpart in the no-glucose culture (FIG. 3B, lane 1). These observations indicate that the increase in the amount of the 34-kDa murein hydrolase is responsible for the increased activity in the quantitative cell wall hydrolysis assay of the UAMS-1 grown in 35 mM glucose (FIG. 3A). In contrast to the parental strain UAMS-1, KB1050 (cidA mutant) displayed a nearly complete loss of extracellular murein hydrolase activity (FIG. 3A), solubilizing less than 10% of the *M. luteus* cell walls. Furthermore, this loss of activity was unaffected by culturing this strain in the presence of 35 mM glucose. This loss of murein hydrolase activity was confirmed by zymogram analysis of the culture supernatants of KB1050 grown in the presence and absence of 35 mM glucose (FIG. 3B, lanes 2 and 4, respectively): in either case, there were no autolytic bands detected. Taken together, these observations demonstrate that the increased murein hydrolase activity observed in UAMS-1 grown in the presence of 35 mM glucose was dependent on the presence of an intact cidA gene.

Figure 4A:
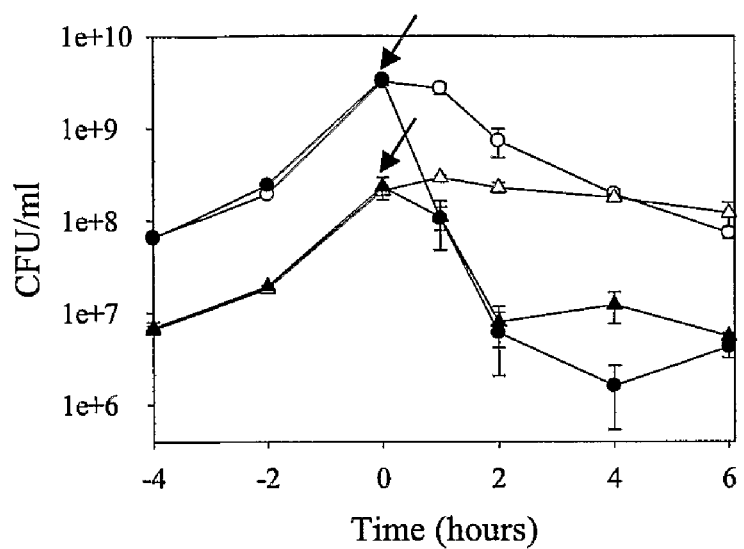
FIGS. 4A and B compare the effect of excess glucose on rifampin sensitivity between UAMS-1 and KB1050. Rifampin (2 μg·ml$^{-1}$) was added to late exponential phase cultures of UAMS-1 (wild-type; circles) and KB1050 (cidA mutant; triangles) grown in either the presence of 35 mM wt/vol glucose (closed symbols) or in the absence of glucose (open symbols), and viable cell counts of each culture were determined by dilution plating on TSA. These data represent the average of three independent experiments, and error bars correspond to the standard errors of the means.
Figure 4B:
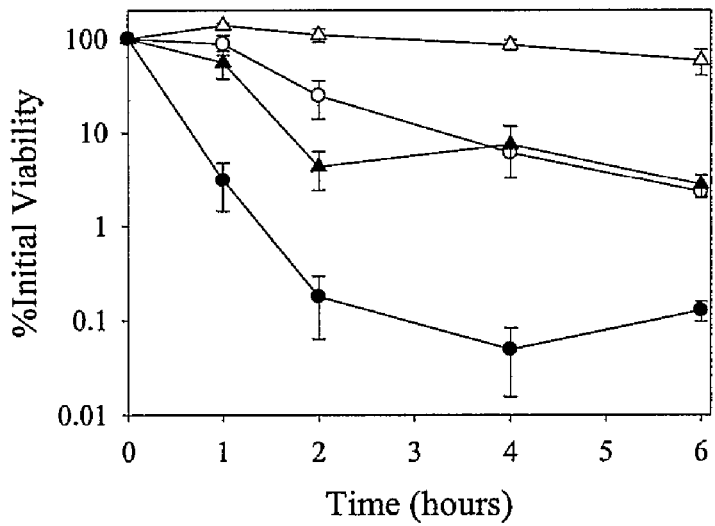
FIG. 4B: This graph depicts the % viability relative to the time of rifampin addition (referred to as the zero time point) for each culture.

Effect of excess glucose on antibiotic sensitivity. The cidA-mutant derivative of RN6390 also displayed increased tolerance to penicillin-induced killing relative to its parental strain (Rice et al., *J. Bacteriol.* 185: 2635-2643, 2003). Antibiotic-induced killing of UAMS-1 and KB1050 in the presence and absence of excess glucose was therefore evaluated (FIGS. 4A and B). The UAMS-1 strain produced β-lactamase and was therefore able to inactivate penicillin. However, the cidA mutation had a similar effect on killing induced by rifampin. Furthermore, since the observed increase in cidABC expression occurred during the mid-exponential growth phase in the presence of 35 mM glucose, rifampin sensitivity under these growth conditions was evaluated. As shown in FIG. 4A, the cidA mutant (KB1050) displayed increased rifampin tolerance relative to UAMS-1 when grown in the absence of glucose, yielding greater than one log unit higher viable cell counts compared to UAMS-1 after incubation with this antibiotic. These results were similar to the penicillin tolerance exhibited by the cidA mutant derivative of RN6390 (Rice et al., *J. Bacteriol.* 185: 2635-2643, 2003). In the presence of 35 mM glucose, conditions in which cidABC expression was induced, UAMS-1 displayed a dramatic increase in rifampin sensitivity, exhibiting a three log decrease in viable cell counts compared to just over one log decrease for UAMS-1 grown in the absence of glucose (FIG. 4B). Interestingly, the KB1050 strain grown in the presence of glucose also displayed increased rifampin sensitivity relative to its growth in the absence of glucose, but still exhibited decreased rifampin sensitivity relative to UAMS-1 grown in the presence of glucose (FIG. 4B). Collectively, these results illustrate that growth in the presence of excess glucose confers increased sensitivity to rifampin, and that the cidA gene product contributes to this effect.

Figure 5:
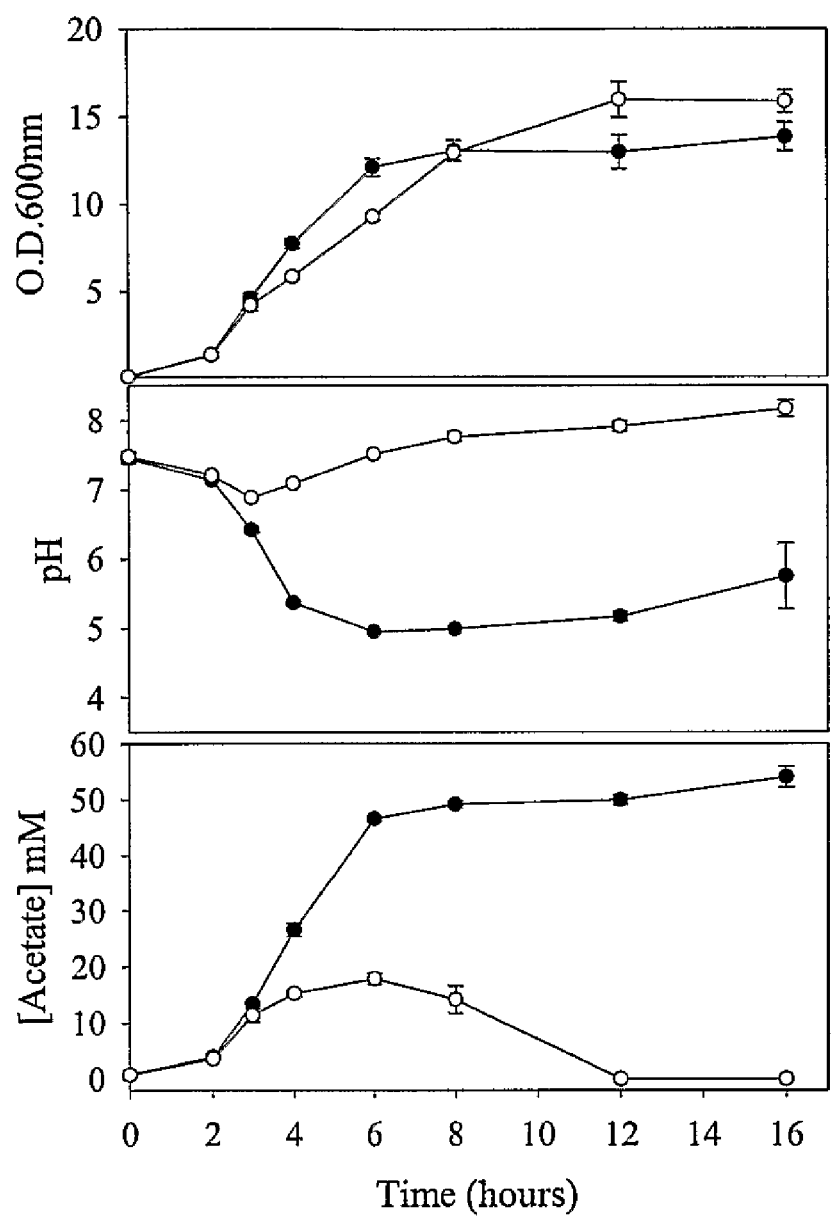
FIG. 5 is a series of graphs, comparing the growth rate (top panel), pH (middle panel), and [acetate] (bottom panel) in UAMS-1 cultures grown in the presence and absence of excess glucose. The growth rate, as determined by O.D.$_{600}$ (top graph), pH (middle graph), and acetate concentration (bottom graph) were measured in UAMS-1 cultures grown in either the presence of 35 mM glucose (closed circles) or in the absence of glucose (open circles). Each parameter represents the average of three independent experiments, and error bars correspond to the standard errors of the means.
Figure 6A:
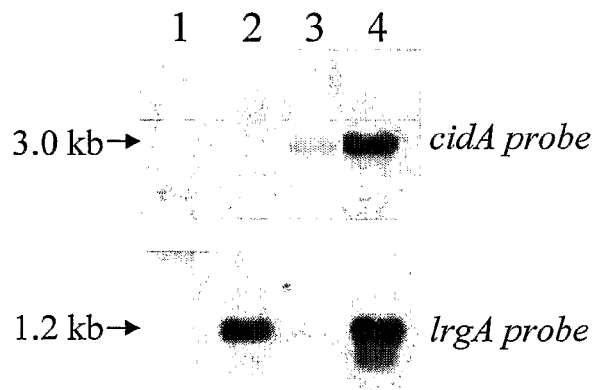
FIGS. 6A and B are Northern blot analyses illustrating that transcription of cidABC and lrgAB is increased by the presence of acetic acid in *S. aureus* UAMS-1.

Acetic acid accumulation induces cidABC and lrgAB expression. The growth yield (measured by optical density), pH, and acetate concentrations of both the glucose-containing cultures and the control (no glucose) cultures of UAMS-1 were monitored. As shown in FIG. 5, a dramatic drop in the pH (from 7.5 to approximately 5.0) as well as a sharp increase in acetate concentration (from 0 mM to approximately 25 mM) was observed after 4 hours growth (mid-exponential phase) in the 35 mM glucose cultures. In contrast, cells grown in the absence of glucose displayed only a slight change in both pH (from 7.5 to approximately 7.0) and acetate accumulation (from 0 mM to approximately 15 mM) at 4 hours growth. Therefore, it is likely that low pH and/or accumulation of acetate (in the form of acetatic acid) in cultures containing excess glucose is the signal that induces high-level expression of cidABC and lrgAB. To confirm this, a Northern blot analysis was performed on RNA isolated from UAMS-1 cells grown for 4 hours in either neutral (pH 7.5) or acidic (pH 5.0) glucose-free NZY medium (FIG. 6A). As expected, growth of UAMS-1 in neutral NZY broth did not increase the expression of either cidABC or lrgAB (FIG. 6A, lane 1), whereas growth in NZY broth that was supplemented with excess glucose resulted in increased expression of both transcripts (FIG. 6A, lane 2). Growth of UAMS-1 in NZY broth adjusted to pH 5.0 with HCl elevated the expression of cidABC relative to growth in neutral media, whereas the effect on lrgAB expression was less dramatic (FIG. 6A, lane 3). However, growth in NZY broth adjusted to pH 5.0 with acetic acid (HAc) had a pronounced positive effect on both cidABC and lrgAB expression (FIG. 6A, lane 4).

Figure 6B:
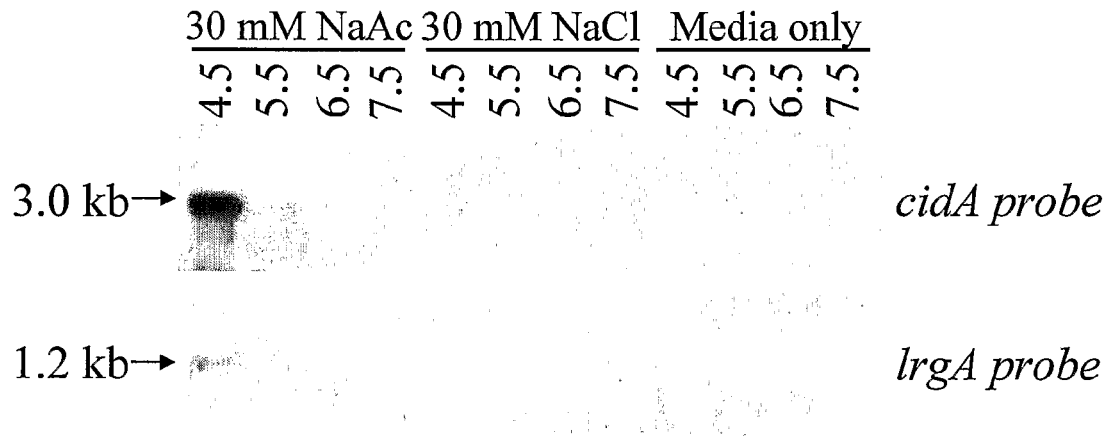
FIG. 6B illustrates the effect of pH on the ability of acetate to increase transcription of cidABC and lrgAB in *S. aureus* UAMS-1. Total cellular RNA was isolated from UAMS-1 grown to mid-exponential growth phase (4-hours post inoculum) in NZY at increasing pH values (from 4.5 to 7.5; as indicated above each lane of the blot), containing either 30 mM sodium acetate or 30 mM sodium chloride as indicated. 5 μg of each sample was separated through a 1% (wt/vol) agarose-formaldehyde gel, transferred to a nylon membrane, and hybridized to cidA- and lrgA-specific DIG-labeled probes. The sizes of each transcript were determined by comparison to an RNA ladder (Invitrogen) run on the same gel.

The concentration of acetate in NZY broth adjusted to pH 5.0 with acetic acid (HAc) (approximately 26 mM) is similar to that found at late exponential growth when UAMS-1 is cultured in the presence of 35 mM glucose (FIG. 6A). Given that the pKa of acetic acid is 4.76, these observations confirm that cidABC and lrgAB expression is induced in 35 mM-glucose cultures by the acid form of acetate (acetic acid) that accumulates as the culture approaches mid-exponential growth (4 hours post-inoculum). In this respect, the moderately increased expression of cidABC and lrgAB observed in NZY broth adjusted to pH 5.0 with HCl is likely to have been a result of the low levels of acetate that are normally found in NZY at this time point (see FIG. 6). To confirm that acetic acid is the signal responsible for stimulating cidABC and lrgAB expression, the ability of 30 mM acetate to induce cidABC and lrgAB expression was assessed by Northern blot analysis on cultures grown for four hours at a wide range of pH values (4.5 to 7.5) (FIG. 6B). Expression of both cidABC and lrgAB dramatically increased in the low-pH media containing 30 mM Na-acetate (pH 4.5-5.5; FIG. 6B, lanes 1-2), whereas expression of both of these transcripts was undetectable in the high-pH media containing 30 mM Na-acetate (pH 6.5-7.5; FIG. 6B, lanes 3-4). By comparison, cidABC and lrgAB expression were not detected at any of the pH values tested in media containing 30 mM NaCl (FIG. 6B, lanes 5-8), indicating that the presence of sodium is not contributing to upregulated cidABC and lrgAB expression. Similar to the results presented in FIG. 6A, lane 3, the cidABC and lrgAB transcripts were detectable at low levels only at the lowest pH tested (4.5; lane 9) in NZY media alone, suggesting that the presence of 30 mM NaCl may be slightly inhibitory to expression of cidABC and lrgAB.

Example 2

The *Staphylococcus aureus* cidC Gene Encodes a Pyruvate Oxidase and Affects the Production of Acetic Acid in Stationary Phase The cid operon expresses two overlapping transcripts. One transcript spans the cidB and cidC genes and is expressed in a sigma B-dependent manner. The other transcript spans all three genes and its expression is enhanced by growth in the presence of 35 mM glucose. Based on sequence comparison studies, the cidC gene encodes a pyruvate oxidase that catalyzes the oxidative decarboxylation of pyruvate to acetate and $CO_2$. The cidC gene product shares 33% identity with PoxB, the *Escherichia coli* pyruvate oxidase, and LpPOX, the *Lactobacillus plantarum* pyruvate oxidase (Rice et al., *J. Bacteriol.* 186(10):3029-3037, 2004). These two enzymes catalyze the decarboxylation of pyruvate although their end products are different (Russell & Gennis *J Biol Chem* 252:7877-7882, 1977; Tittmann et al., *Biochemistry* 39:10747-10754, 2000). The end products of the reaction catalyzed by PoxB is acetate and carbon dioxide (Russell & Gennis *J Biol Chem* 252:7877-7882, 1977), while the end products from the LpPox catalyzed reaction are hydrogen peroxide and acetyl phosphate (Tittmann et al., *Biochemistry* 39:10747-10754, 2000).

Pyruvate oxidase activity was confirmed using a ferricyanide-based spectrophotometric assay that measured pyruvate oxidase activity in crude membrane preparations from the clinical isolate UAMS-1, its cidC mutant derivative, and complemented strains. The cidC mutant produced decreased pyruvate oxidase activity relative to the parental and complemented strains. Acetate levels produced by these strains were also measured spectrophotometrically. A 16-hour time course assay revealed that the acetate concentrations increased up to 6 hours post-inoculation in both the UAMS-1 and cidC mutant cultures. However, the acetate levels of the cidC mutant culture began to decrease after 6 hours and the UAMS-1 culture maintained elevated levels up to 16 hours. The effects of the cidC mutation on murein hydrolase activity were also measured using quantitative cell wall hydrolysis assays. The cidC mutant exhibited an increase in extracellular murein hydrolase activity relative to UAMS-1, but only when grown in the presence of 35 mM glucose. Thus, 1) cidC encodes a protein with pyruvate oxidase activity, 2) cidC affects acetate (and acetic acid) accumulation in excess glucose conditions, and 3) cidC affects murein hydrolase activity possibly by affecting cidABC expression.

Materials and Methods:

Bacterial strains and growth conditions. The bacterial strains used in this study are listed in Table 3. *S. aureus* cultures were maintained on tryptic soy agar (TSA; Difco Laboratories, Detroit, Mich.) plates containing the appropriate antibiotic. Overnight cultures were grown in tryptic soy broth (TSB; Difco Laboratories) or filter-sterilized NZY broth (3% (wt/vol) N-Z Amine A [Sigma Chemical Co., St. Louis, Mo.], 1% (wt/vol) yeast extract [Fisher Scientific, Fair Lawn, N.J.] adjusted to pH 7.5). *E. coli* DH5α and BL21 (DE3) were grown in Luria-Bertani (LB) medium (Fisher Scientific). Unless otherwise stated, cultures were incubated at 37° C. with shaking at 250 RPM in volumes that did not exceed 20% of the flask volume. Antibiotics were purchased from either Sigma Chemical Co. or Fisher Scientific and were used in the following concentrations: erythromycin (Em; 2 µg·ml$^{-1}$), tetracycline (Tc; 5 µg·ml$^{-1}$), ampicillin (Ap; 50 µg·ml$^{-1}$), kanamycin (Km; 30 µg·ml$^{-1}$) and spectinomycin (Sp; 50 µg·ml$^{-1}$).

TABLE 3

Bacterial strains and plasmids

| Strain or Plasmid | Description | Reference or Source |
|---|---|---|
| Strains | | |
| *S. aureus* RN4220 | Highly transformable strain; restriction-deficient | Kreiswirth et al., Nature 305: 709-12, 1983 |
| *S. aureus* UAMS-1 | Clinical isolate | Gillaspy et al., Infect Immun 63: 3373-3380, 1995 |
| *S. aureus* KB1058 | UAMS-1 cidC::Em; Em$^r$ | This study |
| *E. coli* DH5α | Host strain for construction of recombinant plasmids | Hanahan, J Mol Biol 166: 557-580, 1983 |
| *E. coli* BL21 (DE3) | Host strain for pMF58 vector for expression studies. | Studier & Moffatt, J Mol Biol 189: 113-130, 1986 |
| Plasmids | | |
| pDG627 | Source of erythromycin cassette; Em$^r$ or Ap$^r$ | Guerout-Fleury et al., Gene 167: 335-336, 1995 |
| pCL52.2 | Temperature sensitive shuttle vector; Tc$^r$ and Sp$^r$ | Sau et al., J Bacteriol 179: 1614-1621, 1997 |
| pTP100 | Derivative of pCL52.2 containing the Em cassette flanked by cidC fragments; Tc$^r$ and Em$^r$ | This study |
| pAS5 | *S. aureus* xylose inducible expression vector; Ap$^r$ and Tc$^r$ | Staffan Arvidson, MTC Karolinska Institutet, Stockholm, Sweden |
| pTP58 | Derivative of pAS5 containing the cidC open reading frame; Ap$^r$ and Tc$^r$ | This study |
| pCR2.1 | *E. coli* PCR cloning vector; Ap$^r$ | Invitrogen |
| pCR58 | Derivative of pCR2.1 containing the cidC open reading frame; Ap$^r$ | This study |
| pUC18 | *E. coli* cloning vector; Ap$^r$ | Yanisch-Perron et al., Gene 33: 103-219, 1985 |
| pUC58 | Derivative of pUC18 containing the cidC open reading frame at the BamHI and SpHI sites; Ap$^r$ | This study |
| pUC58-2 | Derivative of pUC18 containing the cidC open reading frame at the EcoRI site; Ap$^r$ | This study |

TABLE 3-continued

Bacterial strains and plasmids

| Strain or Plasmid | Description | Reference or Source |
|---|---|---|
| pET24d | E. coli expression vector; Km$^r$ | Novagen (Madison, WI) |
| pMF58 | Derivative of pET24d containing the cidC open reading frame; Km$^r$ | This study |

DNA manipulations. S. aureus genomic DNA was isolated using established procedures (see, e.g., Dyer and Iandolo, Appl Environ Microbiol 46:283-285, 1983). Plasmid DNA was purified using the WIZARD®Plus SV DNA purification kit from Promega, Inc. (Madison, Wis.). Restriction endonucleases used in this study were purchased from Invitrogen Life Technologies (Carlsbad, Calif.). Transformation of E. coli DH5α and BL21 (DE3) was accomplished using procedures established in the art (see, e.g., Inoue et al. Gene 96:23-28, 1990). Introduction of DNA into S. aureus was accomplished by electroporation and bacteriophage-mediated transduction (see, e.g., Kraemer, Current Microbiology 21:373-376, 1990; Shafer & Iandolo, Infect Immun 25:902-911, 1979).

Allele replacement of the cidC gene. A cidC mutation was generated in UAMS-1 using an allele replacement strategy. An 846 bp DNA fragment spanning a region 5' to cidC was amplified using polymerase chain reaction (PCR) with the forward primer, Eco-up (5'-CTTATCTTTGGAATTCGT-TATAACGGG-3'; SEQ ID NO: 11) and the reverse primer, Sma-up (5'-AATAAATGAATTAAACCCGGGCCACCG-3'; SEQ ID NO: 12), incorporating EcoRI and SmaI restriction sites. This fragment was then ligated into the EcoRI and SmaI sites of the plasmid, pDG647 (Guerout-Fleury et al., Gene 167:335-336, 1995) upstream of the Em cassette. Next, an 867 bp 3' cidC fragment was amplified using the forward primer, Cla-dn (5'-GGTCAAATCGATACTTAAACCT-TGG-3'; SEQ ID NO: 13) and the reverse primer, Sal-dn (5'-CCGCTTCCGTCGACAAAAAAGCAGGC-3'; SEQ ID NO: 14), incorporating ClaI and SalI restriction sites. This was subsequently ligated downstream of the Em cassette into the ClaI and SalI sites of pDG647 containing the 5' cidC fragment. The 1.3 kb Em cassette flanked by cidC sequences was liberated by digestion with EcoRI and SalI and then ligated into the plasmid, pCL52.2 (Sau et al., J Bacteriol 179:1614-1621, 1997). This plasmid, designated pTP100, was then transformed into S. aureus strain RN4220 by electroporation and then into UAMS-1 by bacteriophage φ11-mediated transduction, spread onto TSA plates containing Em and incubated at 37° C. overnight. Colonies containing the pTP100 were transferred to TSA plates containing Em and incubated at 44° C. to select for cells in which the plasmid had integrated into the chromosome via homologous recombination. To promote a second recombination event, a single colony was inoculated into TSB without antibiotic and grown at 30° C. for five days, with 1:1000 dilutions into fresh antibiotic free media each day. After the fifth day, dilutions of the culture were spread on TSA medium to yield isolated colonies, which were subsequently screened for resistance to Em and sensitivity to Tc. Em$^R$ and Tc$^S$ isolates were analyzed further using PCR and southern blot analyses to confirm that the cidC gene was replaced with the Em cassette. The cidC mutant was designated KB1058.

Overexpression plasmid construction. Overexpression of cidC in UAMS-1 and KB1058 was achieved by PCR amplification of the cidC open reading frame using Platinum Pfx High Fidelity DNA polymerase (Invitrogen) and the primers, C2-Fbam (5'-ATTAATTTGGATCCTTAAAATGATAGA-CAGAAAGGG-3'; SEQ ID NO: 15) and cidB3-RSph (5'-CCTCCCTTTCTGTCTAGCATGCTAAATATCTAAA-3'; SEQ ID NO: 16) incorporating BamzHI and SpHI sites, respectively. The resulting DNA fragment was then ligated into the BamHI and SphI sites of pUC18 (Yanisch-Perron et al., Gene 33:103-219, 1985), generating pUC58, and sequenced to ensure that no mutations had been introduced during PCR amplification. The cidC DNA fragment was then isolated by digestion of pUC58 with BamHI and SphI and ligated into the xylose inducible expression vector, pAS5, giving rise to the plasmid, pTP58.

To express cidC in E. coli, the cidC open reading frame was PCR-amplified using Platinum Taq High Fidelity DNA polymerase (Invitrogen) and the primers, cidC-FHis (5'-CCCCCATGGCAAAAATAAAAGCAAATGAAGC-3'; SEQ ID NO: 17) and cidC-RHis (5'-CCCCTCGAGTAA-GAAACGTTTTGCTGC-3'; SEQ ID NO: 18), which incorporated NcoI and XhoI sites at the 5' and 3' ends of the PCR product, respectively. The resulting PCR product was ligated into the pCR2.1 vector provided with the T-A cloning kit (Invitrogen Life Technologies) according to the manufacturer's protocols, generating pCR58. The cloned cidC fragment was then excised from pCR58 by digestion with EcoRI, and ligated into the EcoRI site of pUC18, creating the plasmid, pUC58-2. Finally, the cidC gene was removed from pUC58 by digesting with NcoI and XhoI, and cloned into the corresponding sites of the IPTG-inducible expression vector, pET24d, (Novagen, Madison, Wis.), such that a 6× histidine tag would be attached to the carboxy terminus of the cidC gene product. The resulting plasmid was designated pMF58.

Pyruvate oxidase assays. Pyruvate oxidase activities produced by both S. aureus and E. coli strains were assayed using crude protein samples isolated as follows. Overnight S. aureus cultures were washed twice with 1 ml of TSB and then diluted 1:100 into 50 ml TSB in a 250 ml Erlenmeyer flask and incubated for 8 hours. Cells were harvested by centrifugation and resuspended in 10 ml of a freshly prepared buffer containing 0.1 M Na$_2$HPO$_4$ (pH 7.0), 0.1 KCl, 5 mM EDTA (pH8.0), 1 mM DTT, 1 mM PMSF, and 20 mM MgCl$_2$. The cells were lysed by incubating at 37° C. for 1 hour in the presence of 40 ug·ml$^{-1}$ lysostaphin, 13.65 kunitz units of DNase, and 5 μg·ml$^{-1}$ RNase. The lysed samples were centrifuged at 100,000×g in a Beckman Coulter Optima LE-80K Ultracentrifuge for 60 minutes. The resulting pellet was resuspended in 2 ml ME buffer (0.5 M NaCl, 10% glycerol, 20 mM Tris pH 8.0, 35 mM MgCl$_2$, and 1% Triton X-100) and incubated for 18 hours at 37° C. with 75 RPM. The detergent-insoluble material was harvested by centrifugation at 100,000×g in a Beckman Coulter Optima LE-80K Ultracentrifuge for 50 minutes. This supernatant was then used in pyruvate oxidase assays.

Starter cultures of a single colony of E. coli BL21 (DE3) containing either pET24d or pMF58 and grown in LB/Km/1% (wt/vol) glucose were diluted 1:100 into 100 mls of LB/Km/1% (wt/vol) glucose. After reaching an optical density (OD$_{600}$ nm) between 0.2 and 0.5, 0.5 mM isopropylthio-β-D-galactoside (IPTG) was added to the appropriate flasks. These cultures were then incubated for 5 hours at 37° C. with shaking at 250 RPM. Cells were harvested by centrifugation for 10 minutes at 7,900 RPM in a Beckman Coulter Avanti J-25 centrifuge (Fullerton, Calif.) and the cell pellets were stored at −80° C. Protein samples were obtained by resuspending the pellets in 10 ml of lysis buffer containing 500 mM NaCl, 20 mM Tris (pH7.9), 5 mg/ml DNase, 1% (wt/vol) Triton X-100, 2 mM PMSF, and 0.2 mg/ml lysozyme, followed by incubation without shaking at 30° C. for 15 minutes. The samples were sonicated with four 30-sec bursts on a Fisher Scientific Sonic Dismembrator Model 500. The cell lysates were harvested by centrifugation at 12,000 RPM (4° C.) for 30 minutes and stored in 20% (wt/vol) glycerol at −80° C.

The crude protein preparations of E. coli and S. aureus proteins were assayed for pyruvate oxidase activity using established procedures (see, eg., Chang & Cronan, J Bacteriol 151:1279-1289, 1982). Briefly, 200 μg of S. aureus or 100 μl of E. coli extracts were added to 800 μl of an assay mixture containing 500 μl of 0.2 M sodium phosphate buffer (pH 6), 50 μl of 0.2 M MgCl$_2$, 50 μl of 2 mM thiamine pyrophosphate chloride, and 200 μl of 1 M sodium pyruvate. The mixture was incubated at room temperature for 20 minutes and then 100 μl of 0.08 M K$_3$Fe(CN)$_6$ was added. The optical density of 450 nm was then measured using a Pharmacia Biotech Ultraspec 4000 spectrophotometer for a total of 30 minutes and the specific enzymatic activity was calculated using E$_{mM}$=0.218 cm$^{-1}$. Protein concentrations were determined using the Bradford assay according to manufacturer's instructions (Bio-Rad Laboratories, Hercules, Calif.).

16 hr Growth, acetate, and pH analysis. Overnight S. aureus cultures were diluted to an optical density at 600 nm (OD$_{600}$) of 0.1 into 25 ml NZY/35 mM glucose in a 250 ml flask and incubated at 37° C. with shaking at 250 RPM. Samples (1.5-2.5 ml) were collected every two hours for a total of 16 hours. 1.5-2.5 ml samples were centrifuged at 3,000 RPM in a Sorvall RT6000 table-top centrifuge (Newtown, Conn.) for pH and acetate analysis. 100 μl of culture supernatants were stored at −80° C. until acetate concentrations were determined and the pH was taken on an Accumet Basic pH meter (Fisher Scientific).

Determination of acetate concentration. Acetate concentrations were determined in culture supernatants at various time points over a period of 16 hours and in the assay supernatant after analysis for pyruvate oxidase activity. These supernatants were analyzed with a kit purchased from R-Biopharm, Inc. (Marshall, Mich.) and performed according to the manufacturer's instructions.

Long term growth analysis. Overnight S. aureus cultures were inoculated to an OD$_{600}$ of 0.1 into 40 ml NZY with and without 35 mM glucose in a 500 ml flask and incubated at 37° C. with shaking at 250 RPM. Growth was measured by plate counts and at an OD$_{600}$ every couple hours the first day and then every 24 hours thereafter.

RNA isolation. Overnight S. aureus cultures were inoculated to an OD$_{600}$ of 0.1 into 20 ml of NZY broth containing 35 mM glucose in a 250 ml flask and were incubated for 4 hours at 37° C. with shaking at 250 RPM. RNA was isolated with the RNeasy Mini Kit (250) (Qiagen, Valencia, Calif.) and used with modifications of the manufacturer's instructions. Briefly, 3 ml of the bacterial cultures were harvested at 3,000 RPM in a Sorvall RT6000 table top centrifuge (Newtown, Conn.). The bacterial pellet was resuspended in 900 μl of RLT buffer and 10 μl of β-mercaptoethanol was added. This solution was transferred to fast prep tubes containing glass beads and the cells were lysed in a FASTPREP FP120 instrument (Bio 101 Thermo Savant, Vista, Calif.) at a speed of 6.0 for 23 sec. Followed by centrifugation at 13,000 on a Biofuge pico (Heraeus Instruments, Inc. South Plainfield, N.J.) at 4° C. The supernatant was transferred to clean Eppendorf tubes and 500 μl of room temperature 100% ethanol was added and mixed gently. This mixture was added to the mini-column and centrifuged for 20 seconds at 13,000 RPM at room temperature. The remainder of the RNA isolation procedure, including DNase treatment, was performed according to the manufacturer's instructions.

Northern Blot Analysis. RNA samples (5 μg) were separated by electrophoresis in a 1% (wt/vol) agarose gel containing 0.66 M formaldehyde in morpholine propane sulfonic (MOPS) acid running buffer (20 mM MOPS, 10 mM sodium acetate, 2 mM EDTA, pH 7.0), followed by capillary transfer to nylon membrane (Micron Separations Inc., Westboro, Mass.) in 20×SSC (0.3 M Na$_3$-citrate, 3.0 M NaCl, pH 7.0). The transferred RNA was fixed to the membrane by baking at 80° C. for 2 hours. Hybridization and processing of the blots were carried out using components of the DIG system (Roche Applied Science, Indianapolis, Ind.) according to the manufacturer's recommendations for Northern blot analysis. Transcript sizes were estimated by comparison to a RNA molecular mass ladder (Sigma). Probes were synthesized using the PCR-based DIG probe Synthesis Kit (Roche) following the manufacturer's protocols. The primer pairs, cidA1-F (5'-CCCCATATGCACAAAGTCCAATTA-3'; SEQ ID NO: 3), and cidA1-R (5'-CCCCTCGAGTTCATAAGCGTCTA-CACC-3'; SEQ ID NO: 4), were used to generate a DIG-labeled probe corresponding to the cidA gene.

Cell wall hydrolysis assays. Cell wall hydrolysis assays were performed using established procedures (see, e.g., Mani et al., J Bacteriol. 175(5):1493-1499, 1993). Briefly, 50 or 100 μg of concentrated extracellular proteins were added to 100 mM Tris-HCl (pH 8.0) containing 1.0 mg·ml$^{-1}$ Micrococcus luteus cell walls (Sigma) and incubated at 37° C. with shaking at 250 RPM. The OD$_{580nm}$ was measured using a Pharmacia Biotech Ultraspec 4000 spectrophotometer.

Results:

Assay for pyruvate oxidase activity. To confirm that the cidC gene product exhibited pyruvate oxidase activity, a cidC mutant (strain KB1058) was generated and tested using a spectrophotometric assay. As shown in Table 4, the KB1058 strain exhibited reduced pyruvate oxidase activity (0.69 U/mg) compared to the parental strain, UAMS-1 (4.88 U/mg). Production of pyruvate oxidase activity could be restored (33.46 U/mg) by complementation with a plasmid, pTP58, that constitutively expresses the cidC gene. Activity was abolished by omitting the sodium pyruvate from the reactions or by heat-inactivating the proteins. These results indicate that the cidC gene product possesses pyruvate oxidase activity.

TABLE 4

Pyruvate oxidase activities of various S. aureus strains

| Strain | Genotype | Specific Activity (μmol/mg min) | Standard Error N = 4 |
| --- | --- | --- | --- |
| UAMS-1 (pAS5) | wild type | 4.88 | 1.01 |
| UAMS-1 (pTP58) | cidC overexpression | 25.98 | 13.93 |
| KB1058 (pAS5) | cidC mutant | 0.69 | 0.44 |
| KB1058 (pTP58) | complementation | 33.46 | 16.55 |

TABLE 4-continued

Pyruvate oxidase activities of various *S. aureus* strains

| Strain | Genotype | Specific Activity (μmol/mg min) | Standard Error N = 4 |
|---|---|---|---|
| *E. coli* BL21 (pET24d) | IPTG induced control | 59.20 | 34.20 |
| *E. coli* BL21 (pMF58) | IPTG induced cidC overexpression | 2212.00 | 190.18 |

To further verify the pyruvate oxidase activity of the cidC gene product, cidC was expressed from an IPTG inducible plasmid (pET24d) in *E. coli* and crude lysates were tested for pyruvate oxidase activity. As shown in Table 4, proteins derived from cells in which cidC expression was induced with IPTG exhibited a substantial increase in pyruvate oxidase activity (411 U/mg) compared to the sample containing vector alone (0.00 U/mg). Furthermore, proteins derived from uninduced cells also exhibited reduced activity relative to the induced cidC expression samples. In order to test the specificity of the assay different carbon sources were added to the reaction instead of sodium pyruvate using the *E. coli* (pMF58) protein sample. Of the carbon sources tested (glucose, glycerol, sodium lactate, potassium acetate, and phosphoenol pyruvate) the only one that possessed activity was the phosphoenol pyruvate assay and was approximately half of what was seen with sodium pyruvate in the assay. These data show that the cidC-encoded pyruvate oxidase is relatively specific for pyruvate.

Acetate concentrations in pyruvate oxidase assays. The pyruvate oxidase in *E. coli*, PoxB, catalyzes the reaction of pyruvate to produce acetate and carbon dioxide. To determine if CidC catalyzes a similar reaction, acetate concentrations were determined in the solution from the pyruvate oxidase assays in the *E. coli* strains overexpressing cidC. As shown in Table 5, a higher concentration of acetate was observed in the induced cidC expressing strain (5.16 mM) compared to *E. coli* (pET24d) (0.65 mM). These results demonstrate that the catalytic reaction of CidC is similar to PoxB's catalytic reaction with acetate as one of the end products.

TABLE 5

Pyruvate oxidase activities and acetate concentrations of *E. coli* strains overexpressing cidC.

| Strain | Genotype | Specific Activity (μmol/mg min) | Standard Error n = 4 | Average Acetic acid Conc. (mM) | Standard Error n = 4 |
|---|---|---|---|---|---|
| *E. coli* BL21 (pET24d) | IPTG induced control | 0.00 | 0.00 | 0.65 | 0.04 |
| *E. coli* BL21 (pMF58) | IPTG induced cidC overexpression | 822.00 | 110.07 | 5.16 | 0.01 |

In order to rule out acetyl phosphate or acetoin as end products from the CidC catalytic reaction, these two compounds were added to the cuvettes to determine if they are detected with the acetate concentration kit. Acetyl phosphate was used because one of the end products of the LpPOX catalytic reaction is acetyl phosphate (Sedewitz et al., *J Bacteriol* 160:273-278, 1984). The other compound that was looked at was acetoin because another protein that possessed high similarity to CidC was acetolactate synthase. Acetolactate synthase and acetolactate. dehydrogenase catalyzes the reactions of pyruvate to acetoin. These results revealed concentrations of 2.6 mM for the acetate control, 0.17 mM for acetyl phosphate, and 0.068 mM for acetoin. The concentrations of these three solutions were 2.5 mM when added to the cuvette for testing. These results suggest that this assay is specific for acetate and that the end product from the reaction CidC catalyzes is not acetyl phosphate or acetoin.

Growth, pH, and acetate assays. Acetate production during exponential growth results from the conversion of acetyl-CoA into acetate from the pyruvate dehydrogenase complex, which is known to be functional during exponential growth in aerobic conditions (Somerville et al., *Infect Immun* 71:4724-37, 2002). However, the pyruvate dehydrogenase complex is less efficient during the transition into stationary phase and therefore another enzyme would be necessary for the production of acetate. In *E. coli*, PoxB is believed to function at this point in growth, supplying the acetyl units for the transition into stationary phase (Abdel-Hamid et al., *Microbiology* 147: 1483-2498, 2001). To determine if CidC functions in a similar manner as PoxB a 16-hour time-course experiment measuring growth, pH, and acetic acid concentrations every two hours was performed on KB1058 and UAMS-1. When cultures were grown in NZY containing low-levels (17 mM) of glucose there were no differences in the acetate concentrations, pH, or growth between KB1058 and UAMS-1 (FIGS. 7A-D). However, when grown in the presence of elevated glucose (glucose concentrations greater than 20 mM, e.g., 35 mM glucose) all three tests revealed differences, starting at 8 hours, between KB1058 and UAMS-1 (FIGS. 7A-D). As the cultures approached stationary phase, the two strains began to show differences. At 10 to 16 hours there was an increase in pH which corresponds to a decrease in acetate concentration in KB1058. In contrast, UAMS-1 which has some pH increase but no decrease in acetate concentration, suggesting that CidC supplies acetate during late exponential and stationary phases of growth. The difference between the two strains at the 16 hour time point is 17.4 mM acetate and 1.5 pH units. These data further suggest that an end-product product of the CidC catalytic reaction is acetate, as well as, suggesting that CidC has a similar function to PoxB.

Figure 7:
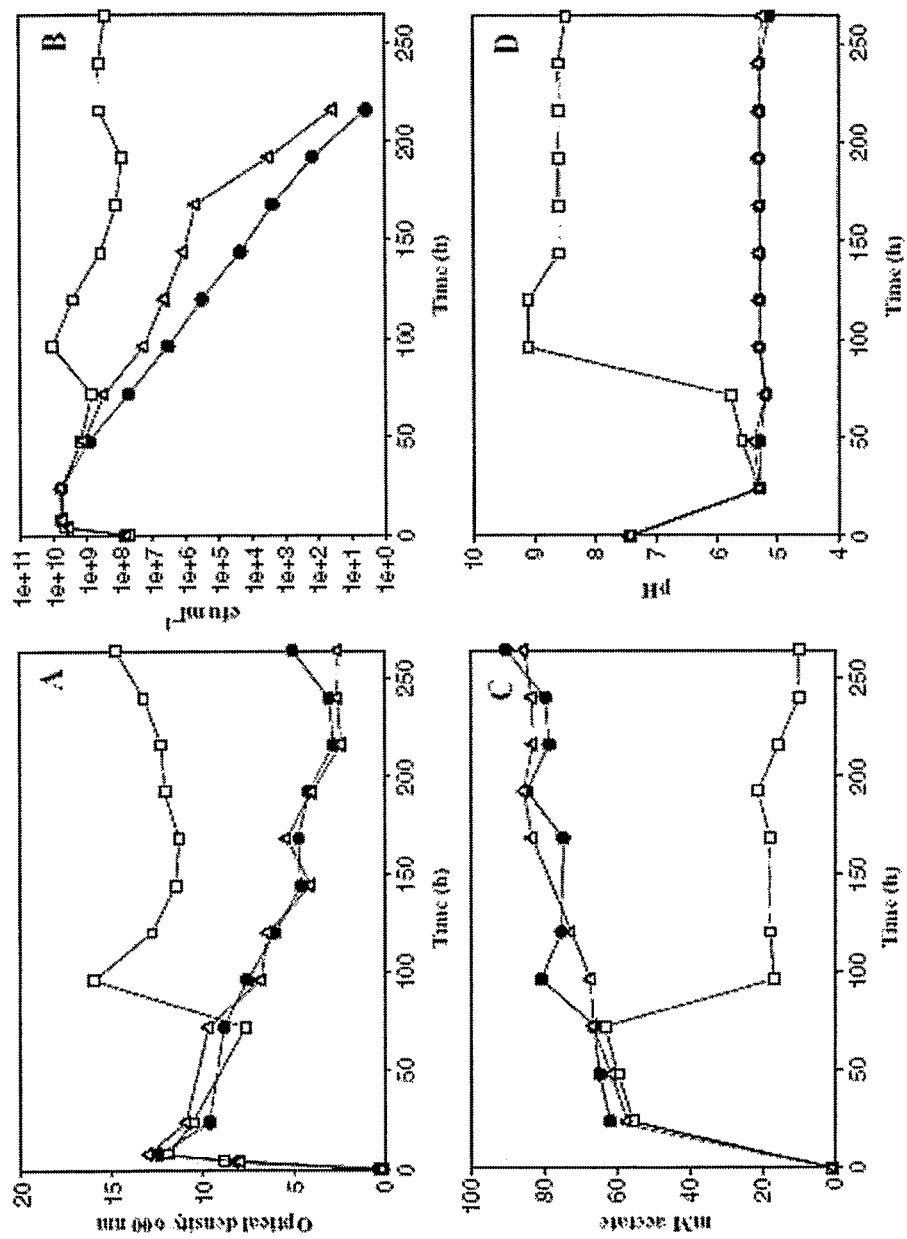
FIGS. 7A-D are a series of graphs showing stationary phase survival of the cidC mutant grown in the presence of 35 mM glucose. The OD$_{600}$ (FIG. 7A), viability (FIG. 7B), acetate concentration (FIG. 7C), and pH of the culture supernatants (FIG. 7D) were monitored ofver a 264 hour timecourse. The strains tested included UAMS-1 (pAS5) (closed circles), KB1058 (pAS5) (open squares), and KB1058 (pTP58) (open triangles).

Long term growth analysis of the cidC mutant compared to the wild type strain was performed to determine if the acetic acid produced by CidC was necessary for post-exponential phase growth and stationary phase killing. In contrast to an isogenic wild-type strain, which loses viability and culture density rapidly once stationary phase is reached, the cidC mutant strain remained viable, and even increased in biomass over greater than 264 hours in culture (FIGS. 7A and B).

Example 3

Induction of the cidABC Operon by CidR

The cidABC operon lies downstream from an open reading frame (ORF), designated cidR (GenBank accession no. AY581892). The gene product of the cidR gene is homologous to the LysR-type transcriptional regulator family of proteins (LTTR). The role of the cidR gene product in regulating expression of the cidABC operon was investigated in detail by creating an isogenic cidR mutant of the previously characterized *S. aureus* clinical isolate, UAMS-1. Northern blot analyses of the cidR mutant indicated that CidR enhances cidABC expression in the presence of acetic acid generated by the metabolism of excess glucose. These data also demonstrate that the cidR gene product affects the control of murein hydrolase activity by enhancing cidABC expression.

Finally, the cidR mutation was also shown to affect both antibiotic tolerance and survival of *S. aureus* in stationary phase.

Materials and Methods:

Bacterial strains and growth conditions. The bacterial strains used in this study are listed in Table 6. All *S. aureus* strains were grown in either tryptic soy broth (TSB; Difco Laboratories, Detroit, Mich.) or filter-sterilized NZY broth (3% (wt/vol) N-Z Amine A [Sigma Chemical Co., St. Louis, Mo.], 1% (wt/vol) yeast extract [Fisher Scientific, Fair Lawn, N.J.], pH 7.5), supplemented as necessary with 1.5% (wt/vol) granulated agar (Difco). *Escherichia coli* DH5α was grown in Luria-Bertani medium (Fisher Scientific). Liquid cultures were grown in Erlenmeyer flasks at 37° C. with shaking (250 rpm) in a volume that was no greater than 10% of the flask volume. All antibiotics were purchased from either Sigma Chemical Co. or Fisher Scientific and were used at the following concentrations: ampicillin (100 µg/ml), erythromycin (Em; 3 µg/ml), chloramphenicol (5 µg/ml), and tetracycline (Tc; 5 µg/ml).

and PstI sites of the plasmid, pDG1515 (Guerout-Fleury et al., *Gene* 167:335, 1995), upstream of a tetracycline (Tc) resistance cassette. This plasmid was designated pRB1. Next, a 458-bp DNA fragment spanning a region 3' to cidR (nt 2626145 to 2626602 of the *S. aureus* 8325 genome) was PCR amplified using the primers, cidR-Kpn (5'-CCCGGTAC-CATCCCTTTCTCGAGATGTCTAAATTG-3'; SEQ ID NO: 24) and cidA-Eco (5'-GGCTTTGTTCCGAATTCTG-TAGCGCA-3'; SEQ ID NO: 25), and ligated into the KpnI and EcoRI sites of pRB1, downstream of the Tc cassette. This plasmid, designated pRB2, was then digested with BamHI and KpnI to liberate a 3.17-kb fragment containing the Tc cassette along with the flanking cidR sequences, which was subsequently ligated into the BamHI and KpnI sites of pCL10 (Sau et al., *J. Bacteriol.* 179:1614-1621, 1997) to generate pRB3. This plasmid was then transformed into UAMS-1 strain by electroporation, spread onto tryptic soy agar (TSA) plates containing chloramphenicol, and incubated at 37° C. overnight. This was followed by growth at the nonpermissive temperature (43° C.) in the presence of tetracycline to select

TABLE 6

Strains and plasmids

| Strain or plasmid | Description | Reference or source |
|---|---|---|
| *S. aureus* | | |
| UAMS-1 | Clinical osteomyelitis isolate | Gillaspy et al., Infect. Immun. 63: 3373-3380, 1995. |
| KB1090 | rsbU+ UAMS-1cidR::Tc | This study |
| KB1050 | Tcr UAMS-1 cidA::Em | Rice et al., J. Bacteriol. 187: 813-821, 2005. |
| *E. coli* | | |
| DH5α | Emr Host strain for construction of recombinant plasmids | Hanahan, J. Mol. Biol. 166: 557-580, 1983. |
| Plasmids | | |
| pRB474 | Shuttle vector carrying the B. subtilis vegII promoter | Bruckner, Gene 122: 187, 1992. |
| pDG1515 | Cmr Source of Tcr cassette | Guerout-Floury et al., Gene 167: 335, 1995. |
| pCR2.1 | Tcr Ampr *E. coli* plasmid | Invitrogen |
| pSJ10 | Ampr pCR2.1 containing 1,465-bp cidR promoter region | This study |
| pSJ11 | CidR ORF cloned into BamHI and EcoRI sites of pRB474 | This study |

Abbreviations:
Tc$^r$; Em$^r$; Cm$^r$; Amp$^r$: tetracycline, erythromycin, chloramphenicol and ampicillin resistance, respectively.

DNA manipulations. Genomic DNA was isolated from *S. aureus* as described above. Plasmid DNA purification was performed using the Wizard Plus kits from Promega, Inc. (Madison, Wis.). Restriction enzymes and T4 DNA ligase used in this study were purchased from either New England Biolabs (Beverly, Mass.) or Invitrogen Life Technologies (Carlsbad, Calif.). Preparation and transformation of *E. coli* DH5α, and electroporation of DNA into *S. aureus* were accomplished using established procedures.

Allele replacement of the cidR gene in UAMS-1. A cidR mutation was generated in *S. aureus* UAMS-1 by allele replacement as follows. A 573-bp DNA fragment spanning a region 5' to cidR (nt 2626938 to 2627504 of the *S. aureus* 8325 genome; http://www.genome.ou.edu/staph.html) was PCR amplified using the primers EmhR1 (5'-GGCCGGATC-CTCACTTCTCTAGGGAAATTGC-3'; SEQ ID NO: 22) and EmhR2 (5'-GCGCCTGCAGACATGCCCATGTTTATAT-GTCC-3'; SEQ ID NO: 23) and was ligated into the BamHI for cells in which the plasmid had integrated into the chromosome via homologous recombination. To promote a second recombination event, a single colony was inoculated into antibiotic-free TSB medium and grown at 30° C. for 5 days with 1:1,000 dilutions into fresh TSB medium each day. After the fifth day, the culture was diluted and spread on TSA plates containing tetracycline to yield isolated colonies. The colonies were then screened for Tcr and Cms phenotypes. Verification that the cidR gene had been deleted was carried out by PCR amplification and Southern blot analyses. The confirmed mutant strain was designated KB1090 (Table 6).

Complementation of the cidR mutation in KB1090 was achieved by PCR-amplifying the cidR open reading frame (ORF) (nt 2626254 to 2627413 of the *S. aureus* 8325 genome) using the primers, cidR-F-BamHI (5'-CCCGGATCCG-TAAAAGCTCAATACCTCACCTCG-3'; SEQ ID NO: 26) and cidR-R-EcoRI (5'-CCCGAATTCG-GAAACGCTCTCTAAATTTCAC-3'; SEQ ID NO: 27). The resulting PCR product was ligated into the BamHI and EcoRI sites of the Gram-positive expression vector, pRB474 (Bruckner, Gene 122:187, 1992). This placed the expression of cidR under the control of the vegII promoter, a vegetative promoter from *Bacillus subtilis*. This recombinant plasmid was designated pSJ11.

Isolation of RNA. For RNA isolation, fresh overnight cultures of *S. aureus* strains were used to inoculate NZY broth to an optical density at 600 nm ($OD_{600}$) of 0.1. Cells were harvested during exponential growth (2 hours), early stationary phase (6 hours), and late stationary phase (12 hours). Total RNA was isolated from the cell pellets by using the RNeasy kit (Qiagen, Valencia, Calif.) and the FASTPREP FP120 instrument (BIO 101, Vista, Calif.), according to the manufacturer's recommended protocols.

Primer extension analysis. The transcription start site of cidR was mapped by primer extension analysis as described by Sambrook et al. (supra). Specifically, the reverse primer, cidR-probe (5'-GCCTCCTTGCTTAACGACTTC-3'; SEQ ID NO: 28), complementary to the 5' end of the cidR gene (nt 2627185 to 2627205 of the *S. aureus* 8325 genome), was end-labeled with [γ-32P]ATP (6,000 Ci·mmol-1) and used in the primer extension reaction. One hundred micrograms of total bacterial RNA, isolated from an exponential growth phase *S. aureus* UAMS-1 culture, were used as a template in the primer extension reaction. A DNA sequencing ladder of the cidR promoter region was obtained using the cidR-probe primer and a Sequenase Kit (United States Biochemical Corporation, Cleveland, Ohio) according to the manufacturer's recommendations for using an end-labeled primer in the sequencing reaction. The plasmid, pSJ10, containing 1,465 bp upstream of the putative GTG translational start site of cidR was used as a template in the sequencing reactions. The sequencing and primer extension products were run simultaneously through an 8% (wt/vol) denaturing polyacrylamide gel and the bands were visualized by autoradiography.

Northern blot analysis. Northern blot analyses were performed essentially as described in Sambrook (supra). DIG-labeled DNA probes were synthesized using a PCR-based DIG Probe Synthesis Kit (Roche), using primers cidA1-F (5'-CCCCATATGCACAAAGTCCAATTA-3'; SEQ ID NO: 3) and cidA1-R (5'-CCCCTCGAGTTCATAAGCGTCTA-CACC-3'; SEQ ID NO: 4) to synthesize cidA specific probe.

Detection of cidABC expression by RT-PCR. Reverse transcriptase (RT)-PCR was performed using routine procedures, with the following modifications. Briefly, cidABC cDNA was generated using Moloney murine leukemia virus (M-MuLV) reverse transcriptase (Fermentas, Hanover, Md.) and the reverse primer, cidC 1-R (5'-GCCGTTGTCGACAATTGT-GATAACCTTTCAATC-3'; SEQ ID NO: 29). The cidABC cDNA products were then detected by PCR using the primer pairs, cidA1-F (5'-AGACATATTTAGAAAGGGATC-CCGCCATGCACAAAGTCC-3'; SEQ ID NO: 30) and cidC1-R. The RT-PCR primers used for the detection of the gyrA transcripts were as described in Rice et al., *J. Bacteriol.* 185:813-821, 2003. PCR reactions for both cidABC and gyrA were carried out in 50-µl aliquots and consisted of 2 µl of cDNA, 0.2 µM of each primer, 10×PCR buffer (Invitrogen Life Technologies), 3 mM MgCl2, 0.2 µM dNTP, and 0.5 U of Taq polymerase (Invitrogen Life Technologies). Amplification was performed with an initial denaturation of 94° C. for 5 min., followed by 25 cycles of denaturation at 94° C. for 30 sec, annealing at 52° C. for 30 sec, and extension at 72° C. for 3 minutes, followed by a final extension step of 72° C. for 5 min. The cidA1-F/cidC1-R primers amplify a 2.9 kb product spanning cidABC and the gyrA-specific primers amplify a 100 bp product (GenBank accession no. D10489).

Murein hydrolase assays. Fresh overnight cultures of *S. aureus* strains were used to inoculate Erlenmeyer flasks containing 10 ml of NZY broth to an initial $OD_{600}$ of 0.1, and were grown for 16 hour at 37° C. and 250 rpm. The culture supernatants were collected by centrifugation and concentrated approximately 6-fold using a Centricon-3 concentrator (Millipore, Bedford, Mass.). Protein concentrations of the extracellular supernatants were determined using the Bradford Assay (Bio-Rad Laboratories, Hercules, Calif.), according to the manufacturer's recommendation. Quantitative cell wall hydrolysis assays were performed using established procedures as indicated above.

Antibiotic tolerance assays. Vancomycin- and rifampin-induced killing of UAMS-1 and KB1090 were assessed by dilution plating.

Determination of stationary-phase survival. Overnight cultures of *S. aureus* strains were used to inoculate 40 ml of NZY medium to an $OD_{600}$ of 0.1. Flasks were capped with bug stoppers (Whatman Inc., Clifton, N.J.), and were grown for up to 2 weeks at 37° C. and 250 RPM. Aliquots (0.3 ml) were taken at 24-hour intervals, and the CFU per milliliter were determined by plating serial dilutions of each sample on TSA plates. Acetic acid and glucose concentrations were determined using kits purchased from R-biopharm, Inc. (Marshall, Mich.) and were used according to the manufacturers' directions. The pH of the culture supernatants was determined using a Beckman, Inc. Φ300 pH meter (Palo Alto, Calif.).

Figure 8:
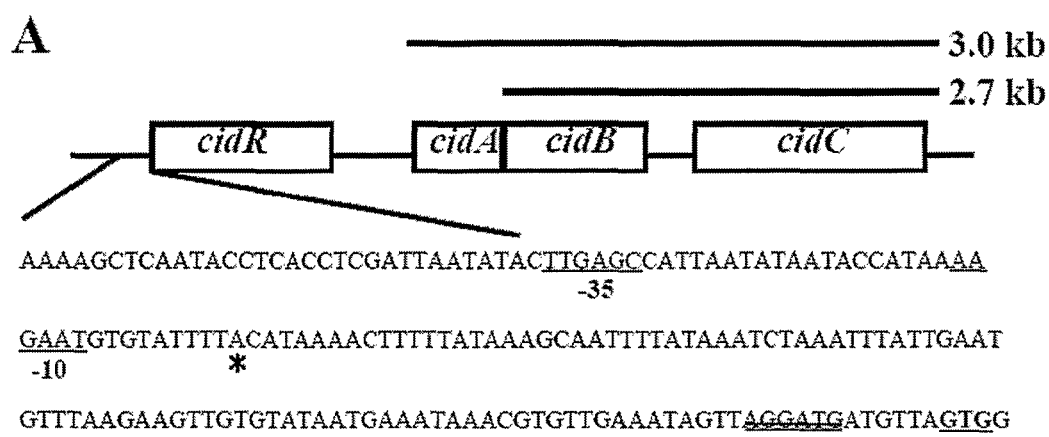
FIGS. 8A and B are a schematic illustration and a digital image, respectively, illustrating the cidR transcription start site, as determined by primer extension analysis. The sequence shown in FIG. 8A is set forth as SEQ ID NO:53.
FIG. 8B is a digital image illustrating primer extension of total cellular RNA (100 µg) (lane 1) from UAMS-1 yielded a 155-bp cDNA product, mapping the cidR transcription start site to an adenine residue located 103 bp upstream of the cidR GTG start codon. The sequence shown is the complement of nucleotides 69-78 of SEQ ID NO:53. The size of the extension product was determined by comparison with the DNA sequencing ladder of the cidR promoter region. Primer extension and sequencing reactions were performed with same primer.
Figure 8:
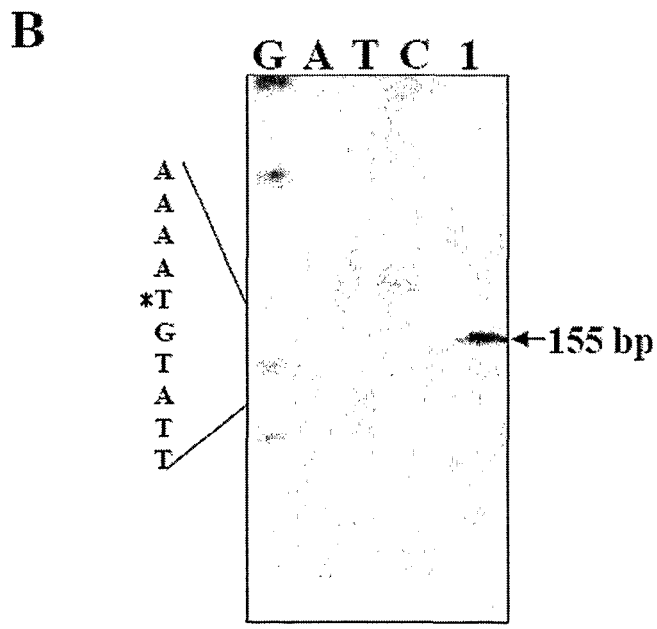

Results:

Identification of the *S. aureus* cidR gene. The cidABC operon is located immediately downstream of an open reading frame (ORF), designated cidR, encoding a LysR-type transcriptional regulator (LTTR) (FIG. 8A). The translation start site of the cidR gene is predicted to be a GTG codon (GenBank accession no. AY581892) based on its proximity to a putative ribosome-binding site (see FIG. 8A) as well as the high degree of amino acid sequence similarity of the resulting N-terminus with other known LTTRs. The amino acid sequence of the cidR gene product (CidR) contains 292 residues with a deduced molecular mass of 33.4 kDa and a pI of 5.39 (http://us.expasy.org/tools/pi_tool.html). Analysis of the CidR amino acid sequence revealed that it contains a conserved N-terminal helix-turn-helix (HTH) motif that is likely to be responsible for DNA binding, and a putative C-terminal regulatory domain, to which an inducer can bind. Unlike most LTTRs, which are usually divergently transcribed from a promoter that overlaps the promoter of their regulated target gene, the cidR gene is transcribed in the same direction as cidABC.

As shown in FIGS. 8A and B, the transcription start site (+1) for the cidR gene was determined by primer extension analysis to be an adenine residue located 103 bp upstream of the predicted cidR start codon. The sequence shown in FIG. 8A is set forth as SEQ ID NO:53. No canonical –10 and –35 elements (5'-TATAAT-3' and 5'-TTGACA-3', respectively) were identified in the sequences preceding the cidR transcription start site. However, the sequences 5'-AAGAAT-3' (9 bp upstream of the cidR +1) and 5'-TTGAGG-3' (19 bp upstream of the putative –10 element) both contain four out of six matches to the predicted σA-dependent –10 and –35 consensus sequences, respectively.

Figure 9:
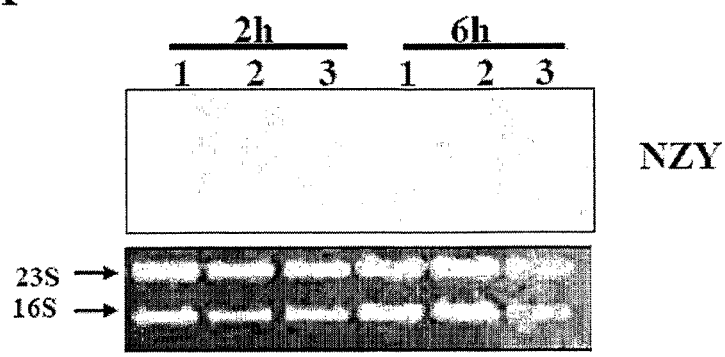
FIGS. 9A-C are digital images illustrating Northern blot analyses of cidABC transcription in UAMS-1, KB1090, and KB1090(pSJ11). Total cellular RNA samples from UAMS-1 (lane 1), KB1090 (lane 2), and KB1090(pSJ11) (lane 3) cells cultured in either NZY broth (FIG. 9A), NZY broth with 35 mM glucose (FIG. 9B), or NZY broth with 26 mM acetic acid (FIG. 9C) were isolated at 2 and 6 hours post-inoculum. Five micrograms of each RNA sample were separated in a 1% (wt/vol) agarose-formaldehyde gel, transferred to a nylon membrane, and hybridized to a cidA-specific DIG-labeled probe. The sizes of the transcripts were determined by comparison to a RNA ladder (Invitrogen) run on the same gel.
Figure 9:
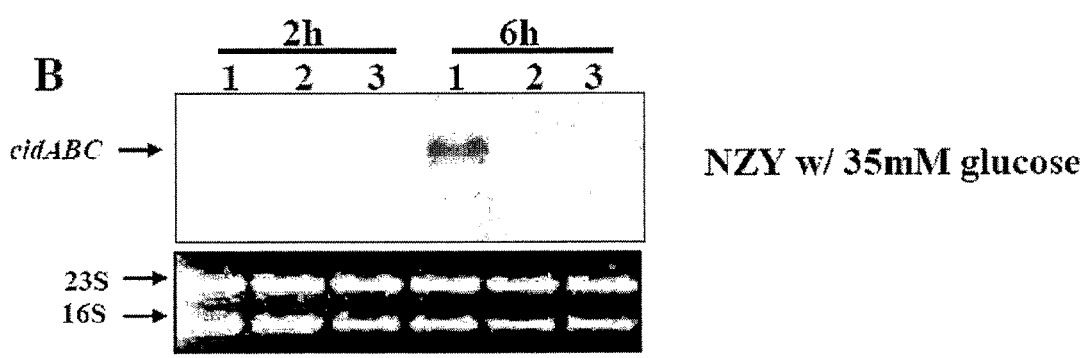
Figure 9:
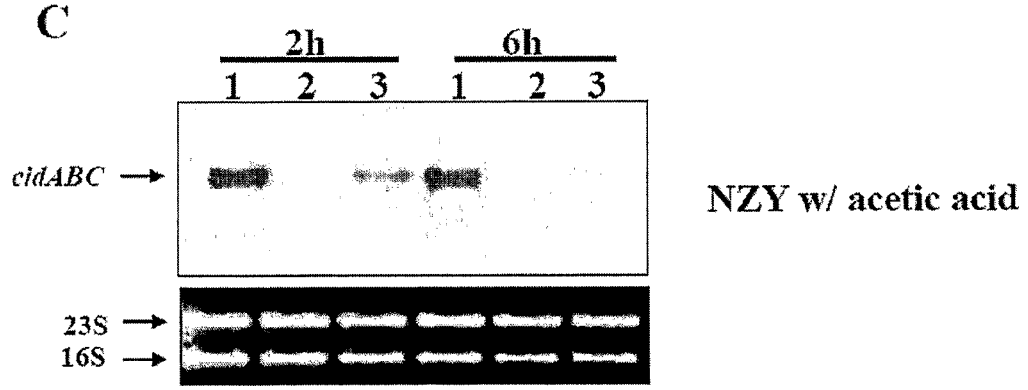

Positive regulation of cidABC transcription by CidR. To address whether cidABC and/or cidBC transcription is regulated by the cidR gene product, a cidR mutant derivative of UAMS-1 (designated KB1090) was generated by replacing 335 bp from the internal region of this gene with a tetracycline (Tc) resistance cassette. To determine the effect of the cidR mutation on expression of the cidR and cidABC genes, Northern blot analyses were performed on RNA samples isolated from cultures of either UAMS-1, KB1090 (cidR mutant), or KB1090(pSJ11) (the cidR mutant containing the cidR complementation plasmid) grown in NZY broth in either the presence or absence of 35 mM glucose. As shown in FIG. 9A, cidABC transcription was not detected both in the UAMS-1 or its isogenic cidR mutant KB1090 when the cultures were grown in NZY broth in the absence of glucose. Expression of cidABC was dramatically induced during the transition into stationary phase (6 hours growth) when UAMS-1 was grown in the presence of 35 mM glucose (FIG. 9B). However, under these same growth conditions the cidR mutant displayed a complete absence of cidABC transcripts at 6 hours of growth, indicating that the increase of cidABC expression observed in the presence of 35 mM glucose is dependent on the cidR gene product. The expression of cidABC in the strain KB1090 (pSJ11) was detectable at low levels at 6 hours in the presence of 35 mM glucose suggesting that the cidR mutation could be partially complemented by expression of cidR from a plasmid. This low-level complementation is likely due to the fact that cidR expression is under the control of the vegII promoter that is maximally active during exponential growth. In contrast to cidABC expression, the expression of cidBC was not affected by the cidR mutation both in the presence and absence of glucose.

A Northern blot analysis was performed on RNA samples from UAMS-1, KB1090, and KB1090 (pSJ11) grown in NZY supplemented with 26 mM acetic acid to determine whether acetic acid induction of high-level cidABC expression is mediated via CidR. Consistent with previously-observed results, growth of UAMS-1 in NZY broth supplemented with acetic acid resulted in dramatically increased expression of cidABC, at 2 hours and 6 hours after inoculation (FIG. 9C). In contrast, growth of KB1090 in acetic acid-supplemented NZY broth showed no detectable cidABC transcripts at either time point. Furthermore, cidABC expression was restored in KB1090 (pSJ11) grown in media supplemented with acetic acid, especially at 2 hours growth when the vegII promoter is thought to be most active (FIG. 9C). Collectively, these results indicate that high-level expression of cidABC in response to acetic acid accumulation generated by glucose catabolism is mediated by cidR gene product.

Figure 10:
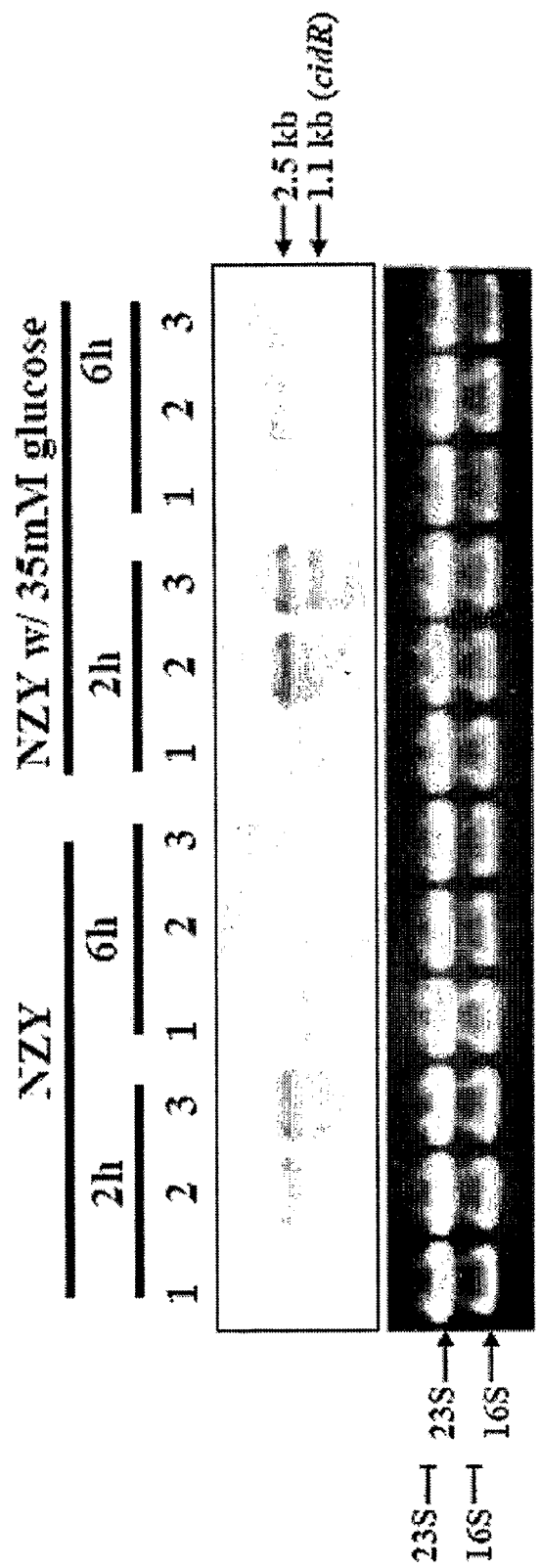
FIG. 10 is a digital image of a Northern blot analysis of cidR transcription in UAMS-1, KB1090, and KB 1090 (pSJ11). Total cellular RNA samples from UAMS-1 (lane 1), KB1090 (lane 2), and KB1090 (pSJ11) (lane 3) cells cultured in either NZY broth or NZY broth with 35 mM glucose were isolated at 2 and 6 hours post-inoculum. Five micrograms of each RNA sample were separated in a 1% (wt/vol) agarose-formaldehyde gel, transferred to a nylon membrane, and hybridized to a cidR-specific DIG-labeled probe.

As shown in FIG. 10, a Northern blot analysis revealed that the cidR gene is transcribed as a 1.1-kb transcript whose expression is induced only during early exponential growth (2 hours growth) in the wild-type *S. aureus* UAMS-1 both in the presence and absence of glucose. In the cidR mutant (KB1090), a 2.5-kb read-through transcript spanning the 5' end of cidR ORF and Tc cassette was also detected only during early exponential growth, indicating the read-through transcript is under the control of the cidR promoter. Expression of the read-through transcript in KB1090 containing the complementation plasmid, pSJ11, was not affected by the complementation of cidR in trans. These data suggest that cidR expression is not negatively autoregulated.

Figure 11:
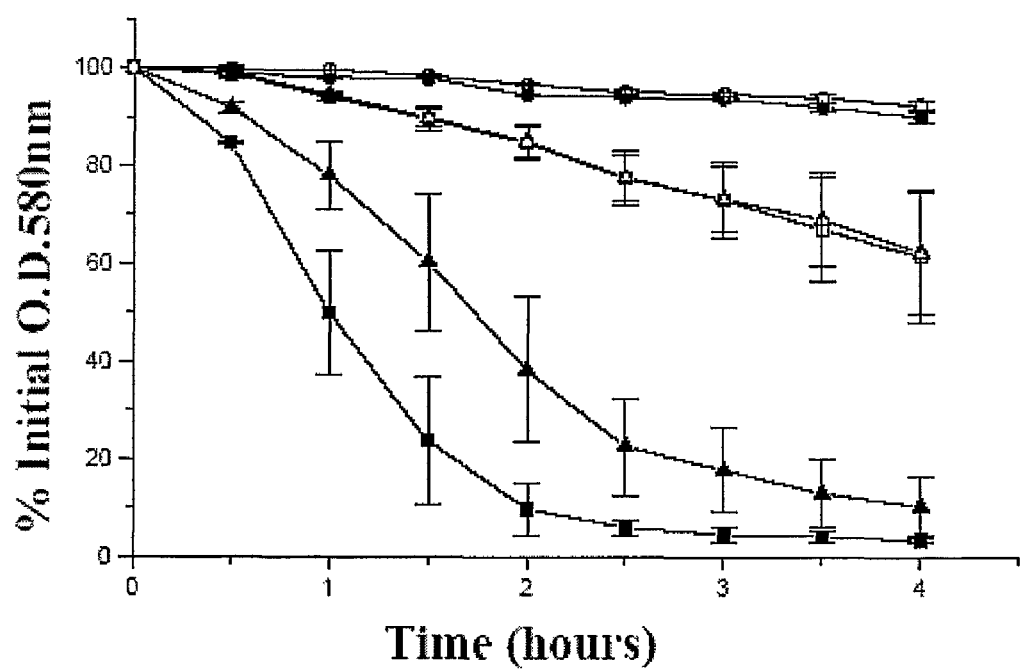
FIG. 11 is a line graph representing results of quantitative murein hydrolase assays of UAMS-1, KB1050, and KB1090. One hundred micrograms of extracellular proteins isolated from 16-hour cultures of UAMS-1 (wild-type; squares), KB1050 (cidA mutant; circles), and KB1090 (cidR mutant; triangles) grown either in the presence of 35 mM glucose (closed symbols) or in the absence of glucose (open symbols) were each added to a 1.0 mg/ml suspension of *M. luteus* cells, and the murein hydrolase activity of each sample was measured as a decrease in turbidity over a 4-hour time course experiment. These data are the average of three independent experiments. The error bars on the graph correspond to the standard errors of the means.

Effect of the cidR mutation on murein hydrolase activity. Murein hydrolase activity was measured to determine whether the cidR mutant, KB1090 exhibit reduced extracellular murein hydrolase activity. As discussed above, the extracellular murein hydrolase activity of UAMS-1 was dramatically increased when grown in the presence of glucose, whereas the activity of KB1050 was almost undetectable and unaffected by the presence of glucose in the growth media (FIG. 11). In contrast, the KB1090 strain produced normal levels of extracellular murein hydrolase activity compared to UAMS-1 when both strains were grown in the absence of glucose. However, when grown in the presence of glucose, the KB1090 displayed a moderate decrease in murein hydrolase activity compared to the activity produced by UAMS-1. KB1090 and UAMS-1 display similar growth rates either in the presence or absence of glucose, ruling out the possibility that the differences in extracellular murein hydrolase activity observed are due to growth rate effects. These observations correlated well with the Northern blot analyses in FIGS. 9A and B, in that cidABC expression is induced only in UAMS-1 in the presence of glucose, whereas KB1090 showed no induction of cidABC transcription in the presence of glucose. The decreased extracellular murein hydrolase activity of KB1090 in the presence of glucose was partially complemented in a strain KB1090 (pSJ11) that expresses cidR from a plasmid, consistent with the partial complementation of glucose-inducible cidABC transcription observed in this strain (FIGS. 9B and C).

Figure 12:
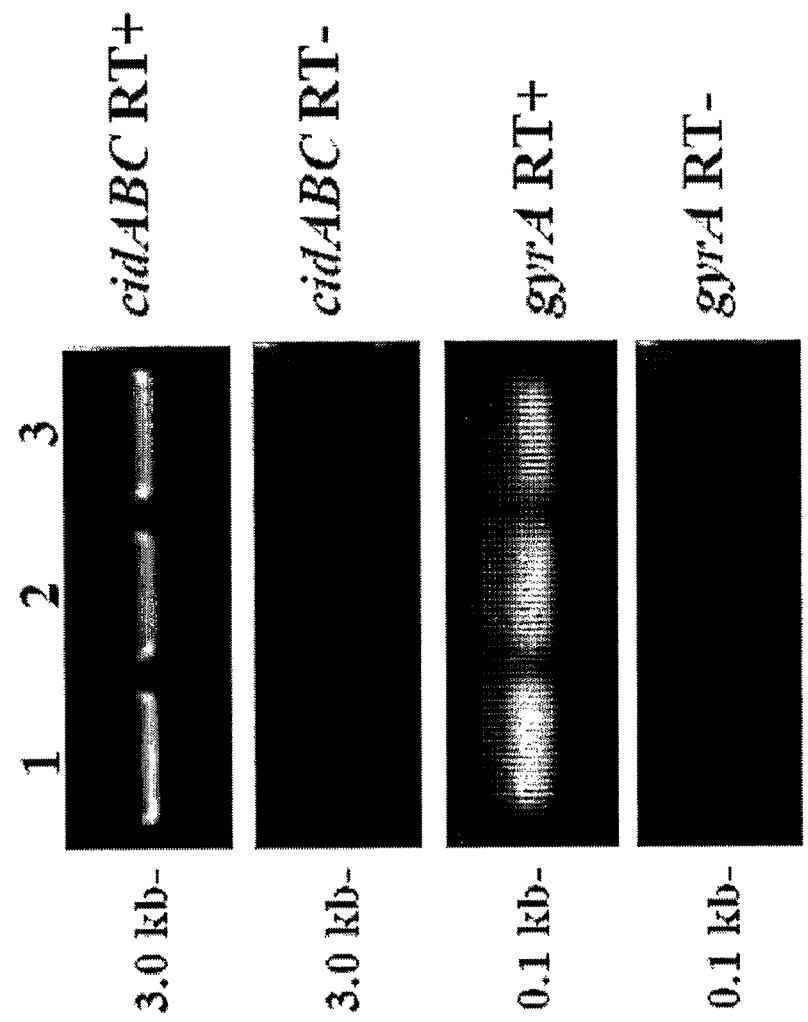
FIG. 12 is a set of digital images illustrating RT-PCR analysis of cidABC expression. RNA samples were isolated from early-exponential growth phase cultures of UAMS-1 (lane 1), KB1090 (lane 2), and KB1090 (pSJ11) (lane 3) grown in NZY broth and were subjected to RT-PCR to detect transcription of cidABC and gyrA. The corresponding gels are labeled as cidABC RT+ and gyrA RT+, respectively. Control reactions (labeled cidABC RT– and gyrA RT–) without RT enzyme were also performed to demonstrate the lack of contaminating genomic DNA in the templates.

Despite its inability to induce cidABC expression, the KB1090 strain still displayed an increase in murein hydrolase activity when grown in the presence of glucose (FIG. 11). One possible explanation to account for this is that the cidR gene product is required for high level expression of cidABC but that glucose-inducible expression is mediated by some other regulatory protein. To test whether the low-level expression of cidABC observed in the absence of glucose is affected by the cidR mutation, a reverse transcriptase (RT)-PCR analysis was performed on RNA samples isolated from UAMS-1, KB1090, and KB1090 (pSJ11) grown in the absence of glucose. As shown in FIG. 12, cidABC expression was identical in all three strains tested, indicating that low-level transcription of cidABC still occurs in the cidR mutant.

Figure 14:
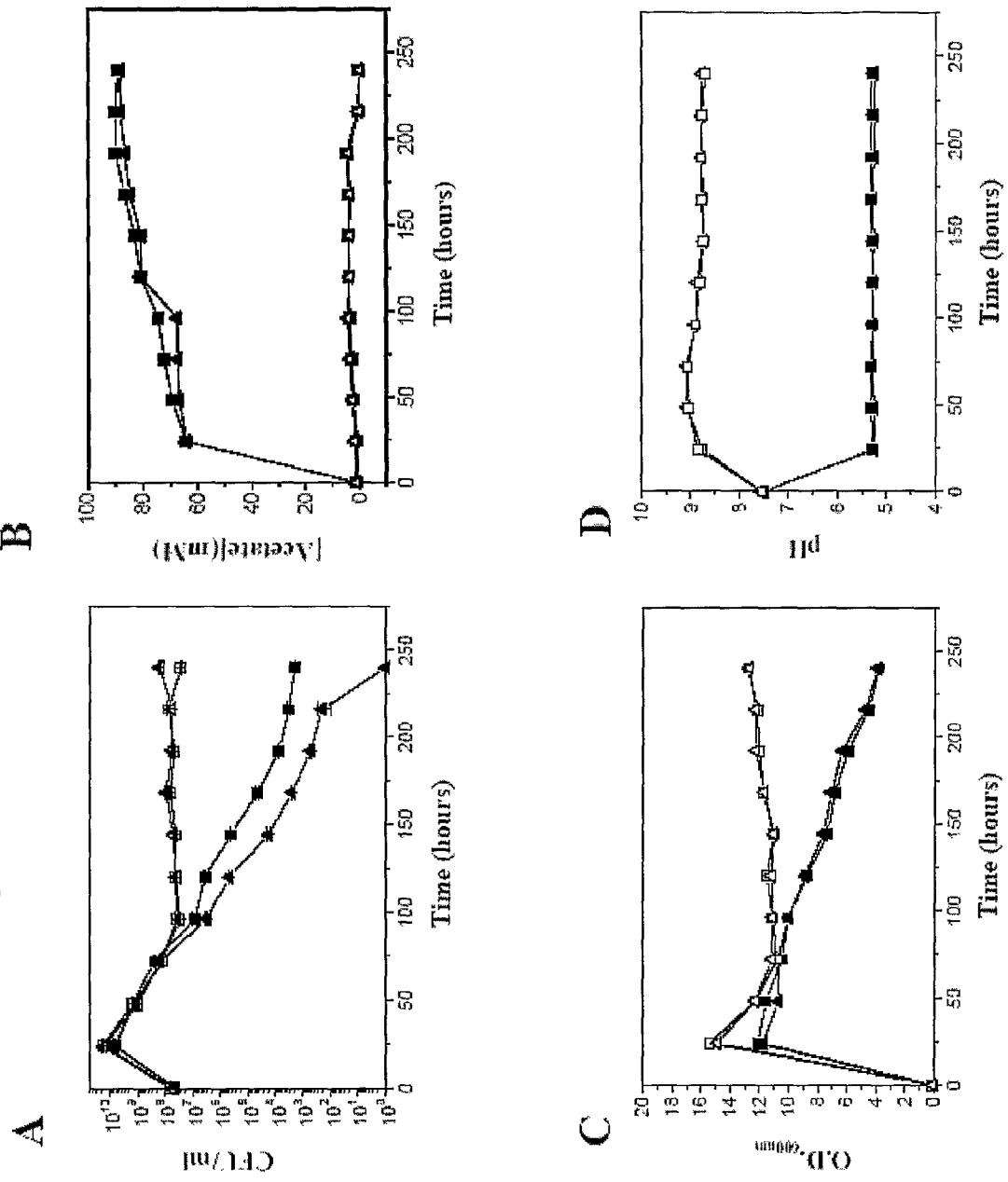
FIGS. 14A-D are line graphs illustrating the effect of cidR on survival in stationary phase. At 24-hour intervals, aliquots of UAMS-1 (wild-type; squares) or KB1090 (cidR mutant; triangles) cultures grown in either the presence (closed symbols) or absence (open symbols) of 35 mM glucose were removed and the CFU per milliliter (FIG. 14A), acetate concentration (FIG. 14B), OD600 (FIG. 14C), and pH of the culture supernatants (FIG. 14D) were measured over a 240-hour time-course experiment. The CFU per milliliter of each culture (FIG. 14A) was determined by dilution plating on tryptic soy agar in triplicate, and the error bars in panel A represent standard errors of means from a single experiment.

Effect of cidR on stationary phase survival. As discussed above, mutations in either the cidA or cidC gene had a dramatic impact on the stationary phase survival, lysis, and acetic acid metabolism of cells grown in the presence of excess glucose. To determine the effects of cidR on stationary phase survival, the UAMS-1 and KB1090 strains were cultured for 240 hours either in the presence or absence of 35 mM glucose, and aliquots of these cultures were taken at 24-hour intervals to determine the pH, acetic acid concentration, OD600, and colony forming units (CFU) per milliliter. As shown in FIG. 14A, when the cultures were grown in the absence of glucose, both UAMS-1 and KB1090 retained similar levels of cell viabilities throughout the experiment. However, in the presence of 35 mM glucose, KB1090 consistently displayed approximately one-log lower viable cell counts relative to UAMS-1 at time points measured after 125 hours growth. By 240-hours growth, the number of viable cells present in the KB1090 culture had dropped to undetectable levels, whereas the viability of the UAMS-1 culture remained at approximately 103 CFU/ml. Both UAMS-1 and KB1090 grown in the absence of glucose displayed similar rates of lysis during the time course of this assay as measured by $OD_{600}$ (FIG. 14C). The $OD_{600}$ was also similar for both strains grown in the presence of glucose, but these cultures displayed increased rates of lysis compared to the no-glucose cultures. These results indicate that the cidR mutation affects stationary-phase viability but not lysis.

Figure 13:
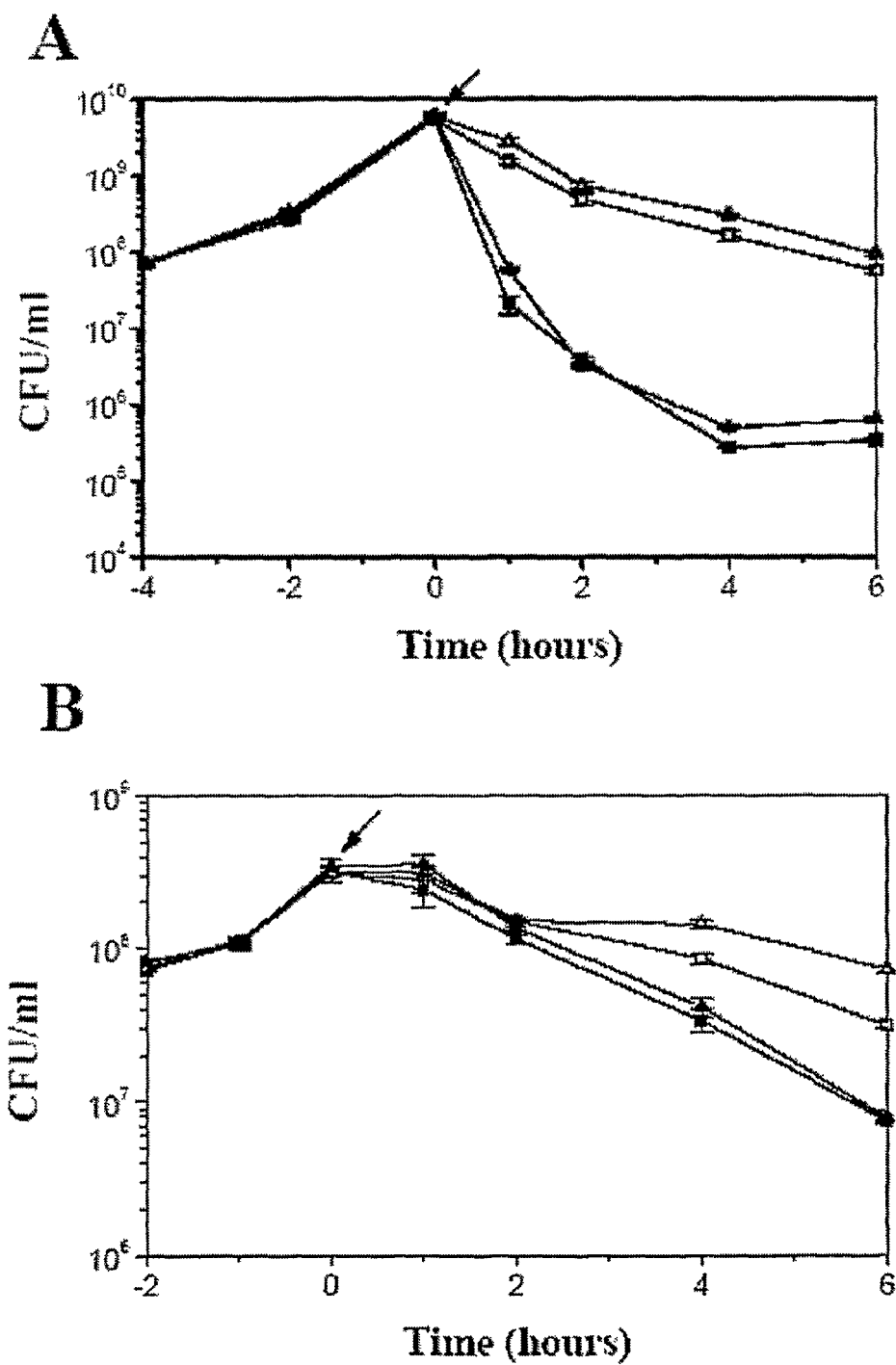
FIGS. 13A and B are line graphs illustrating the effect of cidR on antibiotic tolerance. Rifampin (2 µg/ml) or vancomycin (40 µg/ml) was added to cultures of UAMS-1 (wild-type; squares) and KB1090 (cidR mutant; triangles) cells grown in NZY broth in either the presence of 35 mM glucose (closed symbols) or in the absence of glucose (open symbols), and viable cell counts were determined on TSA plates. These data represent the average of three independent experiments, and error bars correspond to the standard errors of the means. Graphs represent the CFU per milliliter of each culture before and after addition of rifampin (FIG. 13A) and vancomycin (FIG. 13B). The time at which each antibiotic was added to the cultures is indicated by an arrow.

Growth in the presence of 35 mM glucose resulted in the accumulation of high levels of acetic acid (FIG. 14B) and acidification of the culture medium to pH 5.3 (FIG. 14D). As shown in FIGS. 14C and D, the cidR mutation had no effect on the ability of the cells to secrete acetate into the culture medium and, thus, also did not affect the pH. As the cidR mutation has been shown to be involved in the expression of cidABC (see above), the lack of effect on acetic acid accumulation and pH is likely due to the constitutive, high-level, sigma B-dependent expression of the cidBC transcripts. FIGS. 13A and B illustrate the effect of cidR on antibiotic tolerance.

Example 4

The alsSD Operon is Regulated by CidR

CidR differentially regulates the cidABC operon. To determine whether CidR controles transcription and/or activity of additional loci involved in acetic acid metabolism, microarray analysis was performed. CidR was implicated in the regulation of only a small set of *S. aureus* genes, including cidA and lrgAB, which are involved in acetic acid metabolism and cell death pathways. In addition, CidR was found to regulate alsD and alsD. The alsS and alsD genes encode an α-acetolactate synthase and an α-acetolactate decarboxylase, respectively, which are involved in acetoin production.

Materials and Methods:

Bacterial strains and growth conditions. The bacterial strains used in this study are listed in Table 7. All *S. aureus* strains were grown in either tryptic soy broth (TSB; Difco Laboratories, Detroit, Mich.) or filter-sterilized NZY broth (3% [wt/vol] N-Z Amine A [Sigma Chemical Co., St. Louis, Mo.], 1% [wt/vol] yeast extract [Fisher Scientific, Fair Lawn, N.J.], pH 7.5), supplemented as necessary with 1.5% (wt/vol) granulated agar (Difco). *Escherichia coli* DH5α was grown in Luria-Bertani medium (Fisher Scientific). Liquid cultures were grown in Erlenmeyer flasks at 37° C. with shaking (250 rpm) in a volume that was no greater than 10% of the flask volume. All antibiotics were purchased from either Sigma Chemical Co. or Fisher Scientific and were used at the following concentrations: ampicillin (Ap; 100 μg/ml), erythromycin (Em; 3 μg/ml), spectinomycin (Sp; 50 μg/ml), and tetracycline (Tc; 5 μg/ml).

late stationary phase (12 hours). Total RNA was isolated from the cell pellets by using the RNAEASY® RNA isolation kit (Qiagen, Valencia, Calif.) and the FASTPREP® FP120 instrument (BIO 101, Vista, Calif.), according to the manufacturer's recommended protocols.

Microarray analysis. To identify other genes controlled by the CidR regulator, RNA samples from wild-type *S. aureus* strain (UAMS-1) and the cidR mutant (KB1090) were isolated and analyzed by microarray analysis. The GENECHIP® array used contain a comprehensive representation of the *S. aureus* genome compiled using the sequence data from six of the *S. aureus* genomes that are available. The GENECHIP® arrays also contain 11 exogenous sequences derived from the *E. coli* or *B. subtilis* bioB, bioC, bioD, cre and dap genes. More specifically, sequences representing the 5', central, and 3' regions of dap and bioB genes are separately tiled onto the GENECHIP® array. Likewise, sequences of the 5' and 3' regions of cre and bioC are independently located on the GENECHIP® array. These genes have been subdivided into smaller sections to access the completeness of labeling reactions. Labeling reactions also include 1.0 pmole of in vitro transcripts that are complementary to the exogenous genes. These transcripts, termed spike-ins, are included at various concentrations (0.1-2.0 pmole) and are subsequently used to determine both the upper and lower limits of detection in the system. Additionally, they are directly used to normalize for differences in labeling efficiencies and pipetting errors across all samples hybridized to individual GENECHIP® arrays. Finally, plotting the signal intensity produced by each spike-in transcript by the amount of each transcript provides an estimation of the amount of each mRNA species measured on the GENECHIP® array.

To normalize for systematic variations, the raw data generated for each ORF (average difference value) was divided by the median average difference value for each GENE-

TABLE 7

Strains and plasmids

| Strain or plasmid | Description[a] | Reference or source |
|---|---|---|
| *S. aureus* | | |
| UAMS-1 | Clinical osteomyelitis isolate, rsbU+ | Gillaspy et al., Infect. Immun. 63: 3373-3380, 1995. |
| KB1090 | UAMS-1 cidR::Tc; Tc[r] | Described above |
| KB1097 | UAMS-1 alsSD::Em; Em[r] | This study |
| KB1050 | UAMS-1 cidA::Em; Em[r] | Rice et al., J. Bacteriol. 187: 813-821, 2005. |
| *E. coli* | | |
| DH5α | Host strain for construction of recombinant plasmids | Hanahan, J. Mol. Biol. 166: 557-580, 1983. |
| Plasmids | | |
| pDG647 | Source of Emr cassette; Em[r] Ap[r] | Guerout-Floury et al., Gene 167: 335, 1995. |
| pCL52.2 | Temperature-sensitive shuttle vector; Tc[r] Sp[r] | Sau et al., J. Bacteriol. 179: 1614-1621, 1997. |
| pCR2.1 | *E. coli* plasmid; Amp[r] | Invitrogen |
| pSJ11 | pRB474 containing cidR ORF | Hanahan, J. Mol. Biol. 166: 557-580, 1983. |

Abbreviations:
Tc[r]; Em[r]; Cm[r]; Amp[r]: tetracycline, erythromycin, chloramphenicol and ampicillin resistance, respectively.

Isolation of RNA. Fresh overnight cultures of *S. aureus* strains were used to inoculate NZY broth to an optical density at 600 nm ($OD_{600}$) of 0.1. Cells were harvested during exponential growth (2 hours), early stationary phase (6 hours), and CHIP® array. Normalized replicates were averaged together and genes demonstrating a two-fold or greater change in expression were subjected to an ANOVA analysis with a P-cutoff value of 0.05. Additionally, genes will have had to been determined to be "present" by Affymetrix algorithms in the upregulated sampling time. Using this approach with these GENECHIP® arrays has demonstrated a false positive rate of only 0.025% between sample replicates. For biological replicates the false positive rate has been shown to be only 0.7%.

DNA manipulations. Genomic DNA was isolated from *S. aureus* as described above. Plasmid DNA purification was performed using the WIZARD® Plus plasmid isolation kits from Promega, Inc. (Madison, Wis.). Restriction enzymes and T4 DNA ligase used in this study were purchased from either New England Biolabs (Beverly, Mass.) or Invitrogen Life Technologies (Carlsbad, Calif.). Preparation and transformation of *E. coli* DH5α were accomplished using established methods. Electroporation of DNA into *S. aureus* was carried out as described above.

Allele replacement of the alsSD operon in UAMS-1. An alsSD mutation was generated in *S. aureus* UAMS-1 using the following strategy. First, a 668-bp DNA fragment spanning a region 5' to alsS (nt 2292436 to 2293160 of the *S. aureus* 8325 genome; http://www.genome.ou.edu/staph.html) was PCR amplified using the primers alsS-Eco (5'-CCCGAATTCGTCACAGTTA-GATCTAAGTCTTGCTG-3'; SEQ ID NO: 31) and alsS-Bam (5'-AATACAGGATCCCCTTCAGATGTAGC-3'; SEQ ID NO: 32) and was ligated into the EcoRI and BamHI sites of the plasmid, pDG647, upstream of an erythromycin (Em) resistance cassette. This plasmid was designated pSJ13. Next, a 706-bp DNA fragment spanning a region 3' to alsD (nt 2289971 to 2290666 of the *S. aureus* 8325 genome) was PCR amplified using the primers, alsD-Cla (5'-CCCATCGATTG-CATGTACGTATGATGCCGGCA-3'; SEQ ID NO: 33) and alsD-Pst (5'-CCCCTGCAGTAGTTTTAT-AGGGCAAGCGCTGA-3'; SEQ ID NO: 34), and ligated into the ClaI and PstI sites of pSJ13, downstream of the Em cassette. This plasmid, designated pSJ14, was then digested with EcoRI and HindIII to liberate a 2.97-kb fragment containing the Em cassette along with the flanking alsS and alsD sequences, which was subsequently ligated into the EcoRI and HindIII sites of pCL52.2 to generate pSJ15. This plasmid was then transformed into UAMS-1 strain by electroporation, spread onto tryptic soy agar (TSA) plates containing erythromycin, and incubated at 37° C. overnight. This was followed by growth at the nonpermissive temperature (43° C.) in the presence of tetracycline to select for cells in which the plasmid had integrated into the chromosome via homologous recombination. To promote a second recombination event, a single colony was inoculated into antibiotic-free tryptic soy broth (TSB) and grown at 30° C. for 5 days with 1:1,000 dilutions into fresh TSB each day. After the fifth day, the culture was diluted and spread on TSA plates containing tetracycline to yield isolated colonies. The colonies were then screened for $Em^r$ and $Tc^s$ phenotypes. Verification that the alsS and alsD genes had been deleted was carried out by PCR amplification and Southern blot analyses. The confirmed mutant strain was designated KB1097 (Table 7).

Northern blot analysis. Northern blot analyses were performed essentially as described in Sambrook (supra). DIG-labeled DNA probes were synthesized using a PCR-based DIG Probe Synthesis Kit (Roche), using primer pairs cidA1-F (5'-CCCCATATGCACAAAGTCCAATTA-3'; SEQ ID NO: 3) and cidA1-R (5'-CCCCTCGAGTTCATAAGCGTCTA-CACC-3'; SEQ ID NO: 4), lrgA1-F (5'-CCCCATATG-GTCGTGAAACAACAAAAGACGC-3'; SEQ ID NO: 35) and lrgA1-R (5'-CCCCTCGAGATCATGAGCTTGTGC-CTCCTC-3'; SEQ ID NO: 36), alsS-F (5'-AGTACACTG-CAGCCGATATG-3'; SEQ ID NO: 37) and alsS-R (5'-CTAT-AGGATCATAACCGATTG-3'; SEQ ID NO: 38), and alsD-F (5'-GGTACATTAGGCACATTAATGGC-3'; SEQ ID NO: 39) and alsD-R (5'-CTCTAATTTCGTCTGCAATATC-3'; SEQ ID NO: 40) to synthesize cidA-, lrgA-, alsS-, alsD-specific probes, respectively.

Murein hydrolase assays. Fresh overnight cultures of *S. aureus* strains were used to inoculate Erlenmeyer flasks containing 10 ml of NZY broth to an initial $OD_{600}$ of 0.1, and were grown for 16 hours at 37° C. and 250 rpm. The culture supernatants were collected by centrifugation and concentrated approximately 6-fold using a Centricon-3 concentrator (Millipore, Bedford, Mass.). Protein concentrations of the extracellular supernatants were determined using the Bradford Assay (Bio-Rad Laboratories, Hercules, Calif.), according to the manufacturer's recommendation. Quantitative cell wall hydrolysis assays and zymogram analysis were performed as described above.

Determination of stationary-phase survival. Overnight cultures of *S. aureus* strains were used to inoculate 40 ml of NZY medium to an $OD_{600}$ of 0.1. Flasks were capped with bug stoppers (Whatman Inc., Clifton, N.J.), and were grown for up to 2 weeks at 37° C. and 250 RPM. Aliquots (0.3 ml) were taken at 24-hour intervals, and the CFU per milliliter were determined by plating serial dilutions of each sample on TSA plates.

Voges-Proskauer tests. The VP test of liquid *S. aureus* cultures grown in NZY medium containing 35 mM glucose was performed according to established procedures (see, e.g., Blomqvist et al., *J Bacteriol.* 175:1392-404, 1993): 0.25 ml of 0.3% creatine, 0.3 ml of freshly prepared 5% α-naphthol in absolute alcohol, and 0.15 ml of 40% KOH were added to 0.6 ml of bacterial culture supernatant. Formation of red color was monitored for 30 minutes, and the $OD_{540}$ was measured.

Results:

Identification of CidR-regulated genes. To identify genes controlled by the CidR regulator, RNA samples were isolated from cultures of the cidR mutant (KB1090) and its parental strain (UAMS-1) grown in NZY broth in the presence of 35 mM glucose and analyzed by a microarray analysis. Microarray analysis revealed that the cidR mutation affects only a small number of genes, including cidA, lrgAB, alsS and alsD. Consistent with results described above, transcription of cidA gene was highly induced in the presence of excess amount of glucose at early stationary growth phase via CidR-mediated manner. Although the cidA gene is cotranscribed as a cidABC transcript, the cidB and cidC genes were not shown to be highly upregulated in UAMS-1 compared to the expression in KB1090, suggesting the cidBC is still highly expressed in KB1090 in the absence of the cidR gene product. Specifically, cidA gene expression was increased more than 40 fold in UAMS-1 compared to the expression in KB1090 when the cells were grown in the presence of glucose. In addition, the lrgAB genes were shown to be upregulated (approximately 15-fold increase) by CidR in the presence of glucose. The alsSD genes, the newly identified CidR-regulated genes, encode α-acetolactate synthase and α-acetolactate decarboxylase, respectively, involved in acetoin production. Expression of the alsSD genes were upregulated by the cidR gene product approximately 30 fold in the presence of glucose. Taken together, these data suggest that the cidR forms a regulon by regulating expression of multiple unlinked genes.

Figure 15:
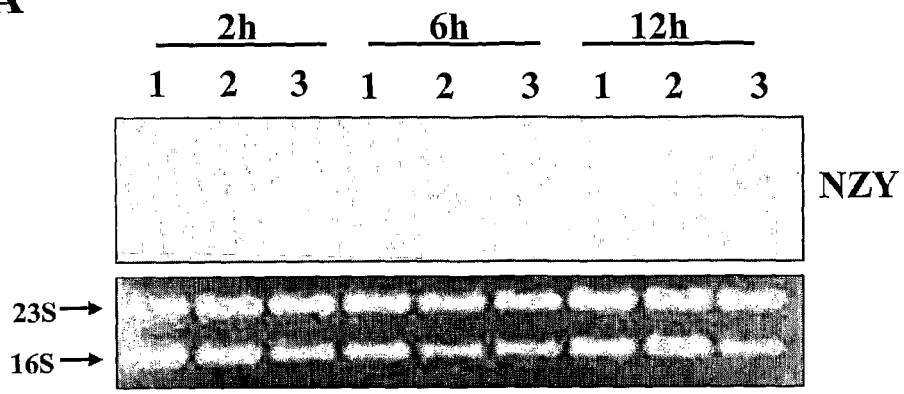
FIGS. 15A-C are digital images illustrating Northern blot analyses of alsSD transcription in UAMS-1, KB1090, and KB1090 (pSJ11). Total cellular RNA samples from UAMS-1 (lane 1), KB1090 (lane 2), and KB1090 (pSJ11) (lane 3) cells cultured in either NZY broth (FIG. 15A), NZY broth with 35 mM glucose (FIG. 15B), or NZY broth with 26 mM acetic acid (FIG. 15C) were isolated at 2, 6, and 12 hours post-inoculum. Five micrograms of each RNA sample were separated in a 1% (wt/vol) agarose-formaldehyde gel, transferred to a nylon membrane, and hybridized to an alsS-specific DIG-labeled probe.
Figure 15:
Figure 15:
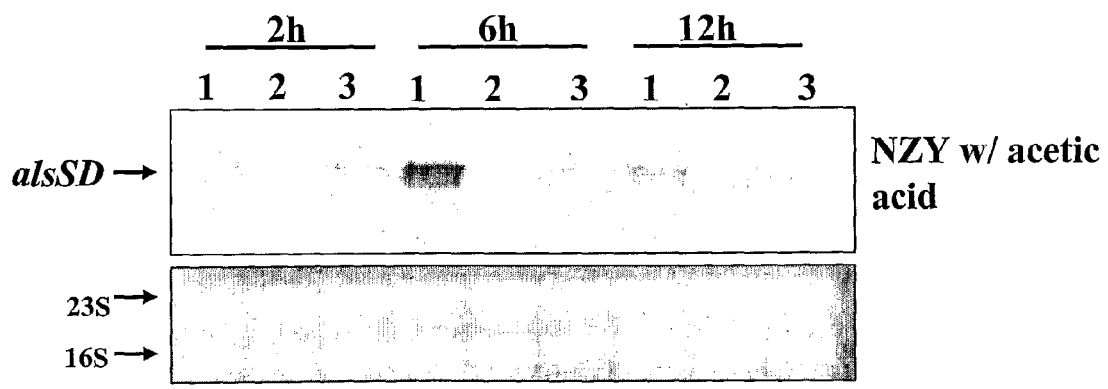

Positive regulation of alsSD transcription by CidR. Microarray analysis identified additional CidR-regulated genes, alsS and alsD, encoding proteins (α-acetolactate synthase and α-acetolactate decarboxylase, respectively) involved in acetoin production. To confirm the transcriptional regulation of the alsS and alsD genes by the cidR gene product, Northern blot analyses were performed on RNA samples isolated from cultures of either UAMS-1, KB1090 (cidR mutant), or KB1090 (pSJ11) (the cidR mutant containing the complementation plasmid) grown in NZY broth in either the presence or absence of 35 mM glucose. As shown in FIG. 15A, alsS transcription was not detected in the UAMS-1 or its isogenic cidR mutant KB1090 when the cultures were grown in NZY broth in the absence of glucose. Unexpectedly, a DNA probe specific for the 5' region of the alsS gene hybridized to a 2.5-kb transcript that was maximally expressed as the UAMS-1 culture reached stationary phase of growth in the presence of 35 mM glucose (FIG. 15B). The size of this transcript indicated that the alsS and alsD genes, each open reading frame (ORF) spanning 1,661 and 705 nucleotides, respectively, are coexpressed as a single transcript. Subsequent Northern blot analysis on the same RNA samples with an alsD-specific DNA probe confirmed that the alsS and alsD genes are coexpressed as a 2.5-kb transcript. However, the cidR mutant displayed a complete absence of alsSD transcript even in the presence of glucose (FIG. 15B), suggesting that the high-level alsSD expression observed in this growth condition is dependent on the cidR gene product. The expression of alsSD in the strain KB1090 (pSJ11) was only detectable at low levels at 2 and 6 h of growth even in the presence of 35 mM glucose. This low-level complementation of alsSD expression in KB1090 (pSJ11) only during exponential and early stationary growth in the presence of glucose is likely due to the fact that cidR expression is under the control of the vegII promoter that is maximally active during exponential growth. Growth phase dependent complementation in KB1090 (pSJ11) was also observed in the previous Northern blot analysis detecting cidABC expression in the presence of glucose. High-level expression of cidABC in response to acetic acid accumulation generated by glucose catabolism is mediated by cidR gene product. Therefore, a Northern blot analysis was also performed on RNA samples from UAMS-1, KB1090, and KB1090 (pSJ11) grown in NZY supplemented with 26 mM acetic acid to determine whether acetic acid induction of high-level alsSD expression is induced via CidR. Similar to cidABC expression, growth of UAMS-1 in ZNY broth supplemented with acetic acid resulted in dramatically increased expression of alsSD at all time points tested (FIG. 15C). In contrast, growth of KB1090 in acetic acid-supplemented NZY broth showed no detectable alsSD transcripts at any of the time points. Furthermore, alsSD expression was restored in KB1090 (pSJ11) grown in media supplemented with acetic acid, especially at 2 and 6 h growth when the vegII promoter is thought to be still active (FIG. 15C). Collectively, these results demonstrate that high-level expression of alsSD in response to acetic acid accumulation generated by glucose catabolism is also mediated by cidR gene product.

Figure 16:
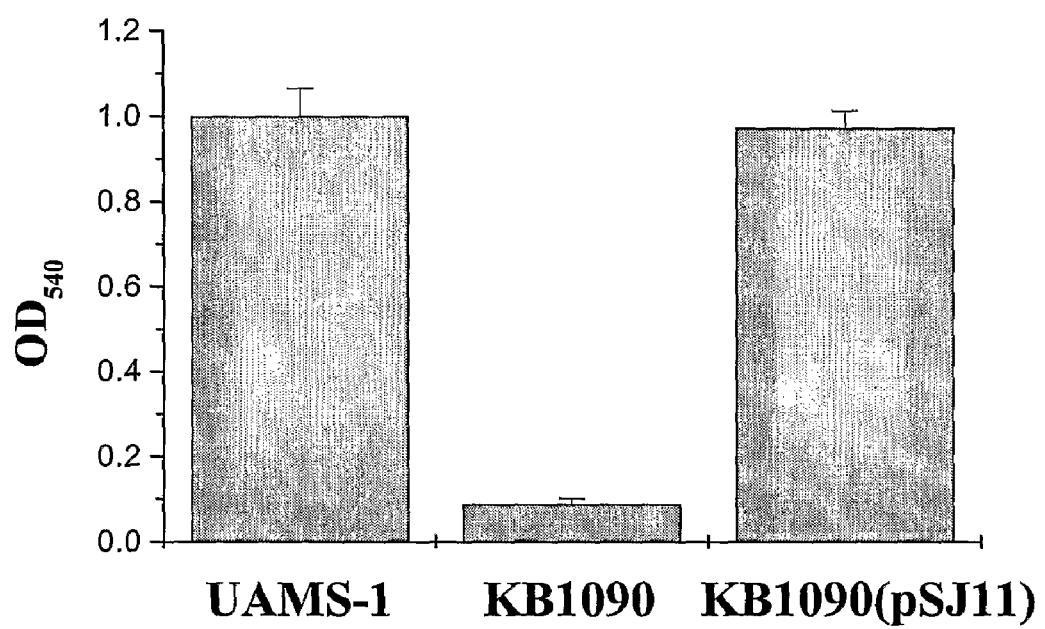
FIG. 16 is a bar graph representing acetoin production by UAMS-1, KB1090, and KB1090 (pSJ11) in the presence of glucose. Six hundred microliters of supernatants from 16-hour cultures of UAMS-1, KB1090, and KB1090 (pSJ11) grown in the presence of 35 mM glucose were each used to determine acetoin production levels. The development of a red color was monitored for 30 minutes at room temperature, and the $OD_{540}$ was measured. The levels of acetoin production in KB1090 and KB1090 (pSJ11) culture supernatants were normalized to that of wild-type stain UAMS-1. These data are the average of three independent experiments. The error bars on the graph correspond to the standard errors of the means.

Effect of the cidR mutation on acetoin production in *S. aureus*. The alsSD operon, which encodes an α-acetolactate synthase and an α-acetolactate decarboxylase, is responsible for acetoin production in certain bacterial species. As shown in FIGS. 15B and C, the cidR mutant derivative of strain UAMS-1 (KB1090) exhibited no detectable alsSD transcripts even when grown in the presence of glucose or acetic acid. To determine whether the cidR mutant, as a positive regulator of alsSD expression, exhibited reduced acetoin production ability, overnight culture supernatants of UAMS-1, KB1090, and KB1090 (pSJ11) grown in the presence of 35 mM glucose were used to determine levels of acetoin production. As shown in FIG. 16, KB1090 produced dramatically decreased amount of acetoin compared to UAMS-1 when grown in the presence of 35 mM glucose. Specifically, level of acetoin production in KB1090 decreased approximately 10 fold relative to that of UAMS-1. The decreased production of acetoin in KB1090 in the presence of glucose was well complemented in strain KB1090 (pSJ11) that expresses cidR from the plasmid. These observations correlated well with the Northern blot analysis shown in FIG. 15B, in that alsSD expression is induced only in UAMS-1 in the presence of glucose, whereas KB1090 showed no induction of alsSD transcription in the presence of glucose. Taken together, these observations demonstrate that cidR gene product enhances production of acetoin by positively regulating transcription of the alsSD operon in the presence of acetic acid produced from glucose catabolism.

Figure 17:
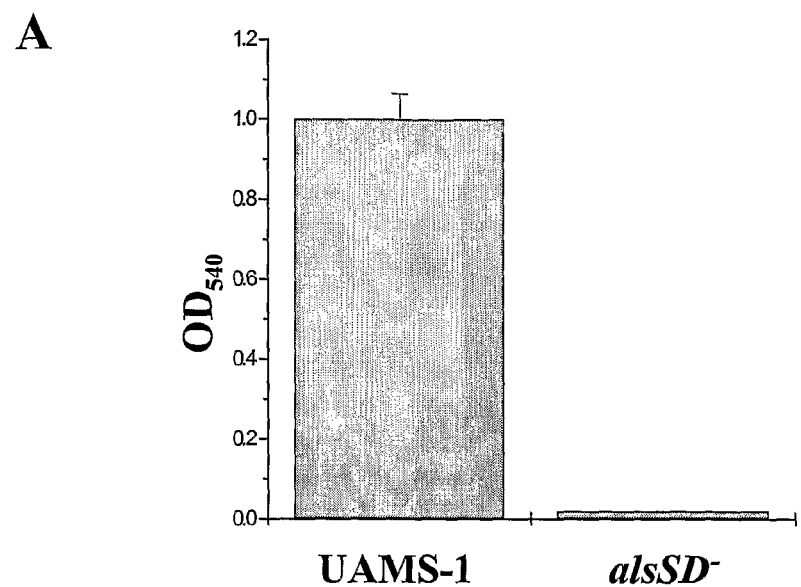
FIGS. 17A and B are a bar graph representing acetoin production and a digital image illustrating a Northern blot analyses (respectively) of UAMS-1 and KB1097.
(FIG. 17B) Total cellular RNA samples from UAMS-1 and KB1097 cells cultured in NZY broth with 35 mM glucose were isolated at 2 and 6 hours post-inoculum. Five micrograms of each RNA sample were separated in a 1% (wt/vol) agarose-formaldehyde gel, transferred to a nylon membrane, and hybridized to alsS-, lrgA-, or cidA-specific DIG-labeled probes.
Figure 17:
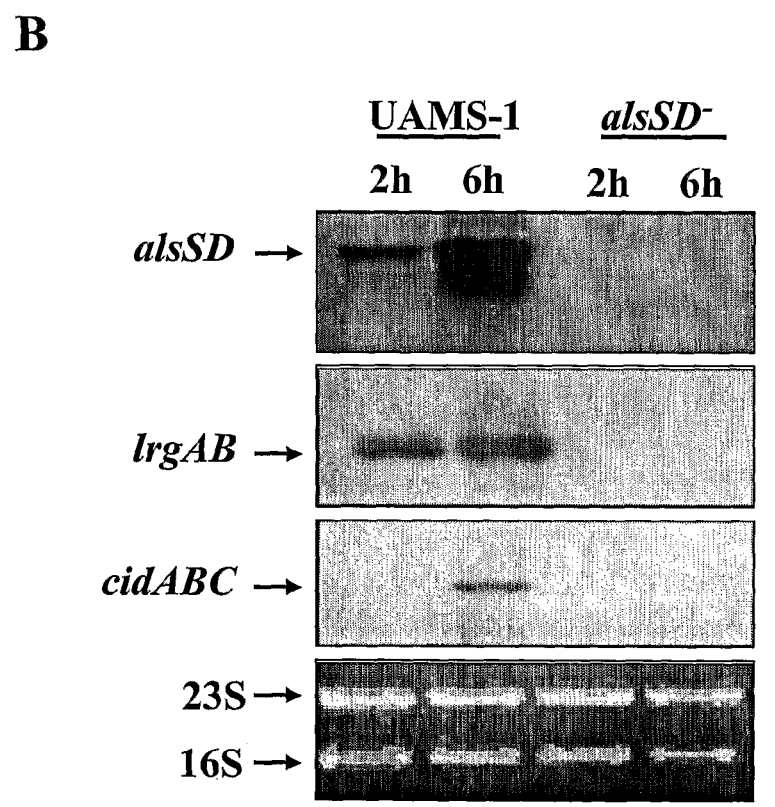

Effect of the alsSD mutation on transcription of cid and lrg operons. The cidR gene, whose product is homologous to the LysR-type transcriptional regulator family of proteins (LTTR), positively regulates expression of cidABC, lrgAB, and alsSD operons in the presence of glucose. Many LTTRs positively regulate transcription of their target genes whose products are enzymes involved in various metabolic pathways, and some of the pathway intermediates serve as coinducers for the target gene expression. Thus, the alsSD operon which is involved in acetoin production in the presence of glucose, affects transcription of the cid and lrg operons, e.g., by providing a coinducer for CidR-mediated cidABC and lrgAB expressions. To determine whether alsSD regulates expression of the cidABC and lrgAB operone, an alsSD mutant derivative of UAMS-1 (designated KB1097) was generated by replacing 1.76 kb from the internal region of the operon with an erythromycin (Em) resistance cassette. As a result of mutation in alsSD, acetoin production in the alsSD mutant was completely impaired even in the presence of glucose (FIG. 17A). To determine the effect of the alsSD mutation on expression of the cidABC and lrgAB genes, Northern blot analyses were performed on RNA samples isolated from cultures of either UAMS-1 or KB1097 grown in NZY supplemented with 35 mM glucose. Expression of cidABC was significantly induced during the transition into stationary phase (6 hours growth) and lrgAB expression was also induced both at 2 and 6 hours growth when UAMS-1 was grown in the presence of 35 mM glucose (FIG. 17B). However, under these same growth conditions the alsSD mutant displayed a complete absence of both cidABC and lrgAB transcripts, demonstrating that the dramatic increase of cidABC and lrgAB expression observed in the presence of 35 mM glucose is dependent on the presence of an intact alsSD genes.

Figure 18:
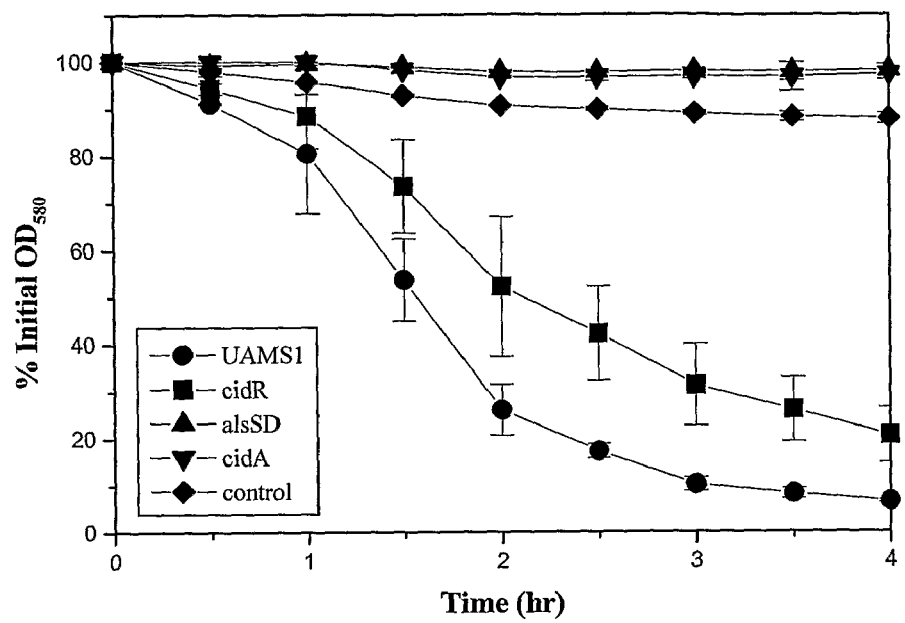
FIGS. 18A and B are a line graph and a digital image, respectively.
FIG. 18B is a digital image illustrating a zymogram analysis of extracellular murein hydrolase activities of UAMS-1, KB1050, KB1090, and KB1097.
Figure 18:
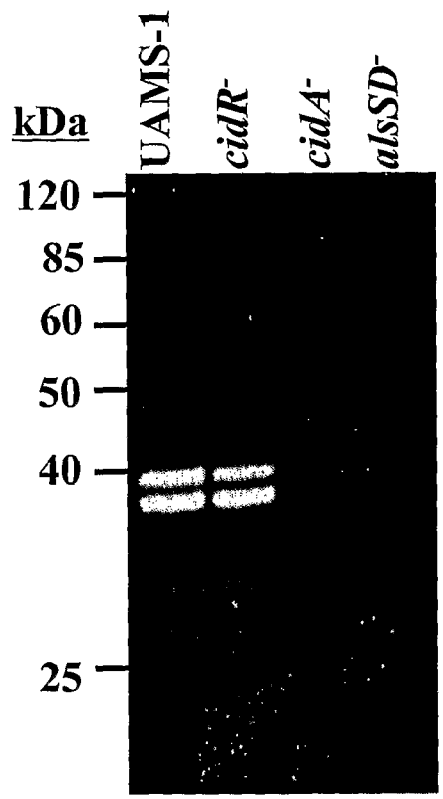

The alsSD genes affect murein hydrolase activity. To determine whether extracellular murein hydrolase activity regulated by cidABC and lrgAB expression was affected in the alsSD mutant, KB1097, extracellular murein hydrolase activity was evaluated. When grown in the presence of 35 mM glucose, KB1090 displayed a moderate decrease in extracellular murein hydrolase activity compared to the activity produced by UAMS-1, whereas the activity of the cidA mutant was almost undetectable (FIG. 18A). The alsSD mutant also displayed a near-complete loss of extracellular murein hydrolase activity in the presence of glucose (FIG. 18A), solubilizing less than 5% of the *M. luteus* cell walls. This loss of murein hydrolase activity was confirmed by zymogram analysis of the culture supernatants of UAMS-1, KB1090, KB1050, and KB1097 grown in the presence of glucose (FIG. 18B). Thus, like the cidA gene, whose product has a positive effect on murein hydrolase activity, the alsSD genes have a positive impact on murein hydrolase activity.

Figure 19:
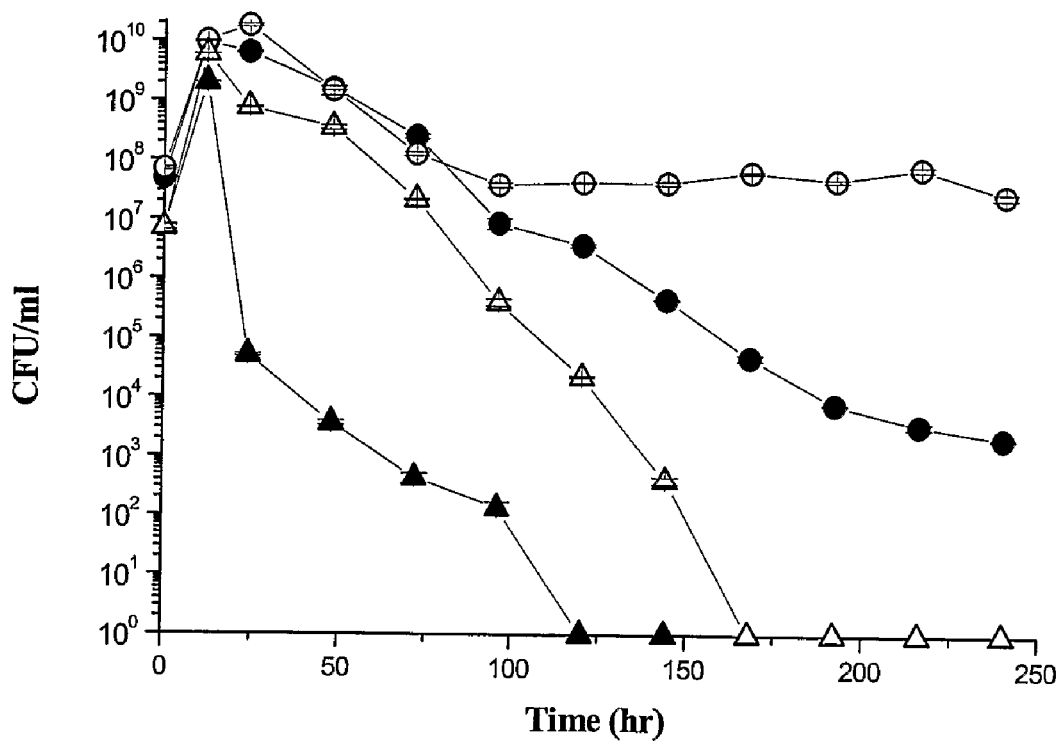
FIG. 19 is a line graph representing stationary-phase survival of UAMS-1 and KB1097. At 24-hour intervals, aliquots of UAMS-1 (Wild-type; circles) or KB1097 (alsSD mutant; triangles) cultures grown in either the presence (closed symbols) or absence (open symbols) of 35 mM glucose were removed and CFUs per milliliter were measured over 240-hr time-course experiment. The CFU per milliliter of each culture was determined by dilution plating on tryptic soy agar in triplicate, and the error bars represent standard errors of means from a single experiment. All these data are from a single representative experiment and were reproduced three times.

The impact of alsSD on stationary phase survival. To determine the effects of alsSD on stationary phase survival, the UAMS-1 and KB1097 strains were cultured for 240 hours either in the presence or absence of 35 mM glucose. When grown in the absence of glucose, the UAMS-1 retained high level of cell viability (>$10^7$ CFU/ml) (FIG. 19). Growth in the presence of 35 mM glucose caused significant decrease in viability (approximately $10^3$ CFU/ml at 240-hours growth) in the UAMS-1 culture. Surprisingly, the alsSD mutant also displayed a complete loss of viability from 168 hours growth when grown in the absence of glucose. In the presence of glucose, the alsSD mutant exhibited even more rapid loss of viability compared to the growth in the absence of glucose. By 120-hours growth, the number of viable cells present in the KB1097 culture had dropped to undetectable levels in the presence of 35 mM glucose, whereas the viability remained at approximately $10^4$ CFU/ml in the absence of glucose. These results indicate that the alsSD genes have a dramatic impact on cell viability in stationary phase both in the presence and absence of glucose.

Example 5

Construction of *Bacillus anthracis* cidR, cidA and cidAB Mutants

To confirm that acetic acid metabolism and murein hydrolase activity were regulated in a comparable manner in other bacterial species, mutations in cidR, cidA, and cidAB were made in the Gram-positive species *Bacillus anthracis*.

Materials and Methods:

Generation of *Bacillus anthracis* cid mutants. A 1100-bp DNA fragment spanning a region 3' to cidR was amplified with the primers cid1F 5'-CTCGGTACCCGTTTTCAGTTC-CTTCTATGTCA-3'; SEQ ID NO: 41 and cid1R 5'-ATAG-GATCC AGATCTCTTGTAGCAGCAGGGATT-3'; SEQ ID NO: 42 and cloned into pLC1 following digestion with KpnI and BamHI. A 1809-bp DNA fragment spanning of 5' to cidR was amplified with the primers cid2F 5'-TTCGGATCCCTC-GAGACTAGTTGTAACTCCTCTGCCACT-3'; SEQ ID NO: 43 and Cid2R 5'-ATAGTCGACACGCGT-GCTTTCATCCTTCCGTTTA-3'; SEQ ID NO: 44 and cloned into pLC1 following digestion with BamHI and SalI. A 1158-bp DNA fragment of the spectinomycin gene was amplified from pDG1726 with primers SPC-F 5'-GT-GAGATCTATCGATTTTCGTTCGTGAATACATGTT-3'; SEQ ID NO: 45 and SPC-R 5'-GTCCTCGAGCATATG-CAAGGGTTTATTGTTTTCT-3'; SEQ ID NO: 46 and cloned into pLC1 (pJA5) following treatment with BglII and XhoI. Since adenine methylated plasmid caused very low efficiency of transformation in *B. anthracis*, de-methylated plasmid was prepared from dam-*E. coli* JM110 and was electroporated into *B. anthracis*. Transformed *B. anthracis* was spread onto Brain Heart Infusion (BHI) agar plates containing Kanamycin (50 ug/ml), and incubated at 37° C. overnight. A colony was grown overnight at 37° C. in BHI broth with spectinomycin (SPC) (100 ug/ml), then subcultured into antibiotic-free BHI broth and grown at for 30° C. for several days, with 1:1000 dilutions into fresh antibiotic-free medium each day. After the third day, dilutions of the culture were spread on BHI agar plates with SPC (100 ug/ml) to have isolated colonies and subsequently screened for $SPC^R$ and $Kan^S$. The cidR deletion mutation was confirmed by PCR.

To disrupt the cidA gene, a knockout plasmid (pJA10) was constructed by replacement of 5' end and 3' end fragments of pJA5. 5' end fragment of pJA5 was replaced with 1224 bp of Cid-3F (KpnI) 5'-ATC GGTACCACATCGCACTACAATCGG-3'; SEQ ID NO: 47 Cid-3R (BglII) and 5'-GTCAGATCT TCATACAGTAAC-CACCTCT-3'; SEQ ID NO: 48. 3' fragment of pJA5 was replaced with 1277 bp of Cid-4F (SpeI) 5'-GTG ACTAGTTTGCTACTAAAGCGGAAAGG-3'; SEQ ID NO: 49 and cid2R (MluI) 5'-GTG ACGCGTGCTTTCATCCTTCCGTTTA-3'; SEQ ID NO: 50. CidA knock mutant was constructed as described above and confirmed by PCR.

To dirupt the cidA and cidB genes simultaneously, a cidAB knockout plasmid (pJA11) was constructed by replacing the 3' fragment of the cidA knockout plasmid (pJA10) with a cidB 3' fragment. The cidB 3' fragment (889 bp) was amplified using primers Cid-6F (SpeI) 5'-GTC ACTAGTCTGTAGAGGGAACAATCGC-3'; SEQ ID NO: 51 and Cid-6R (MluI) 5'-ATGACGCGTATCGGATAT GAAAGCTGACC-3'; SEQ ID NO: 52. The cidAB knockout mutant (KB2055) was constructed as above and confirmed by PCR.

Figure 20:
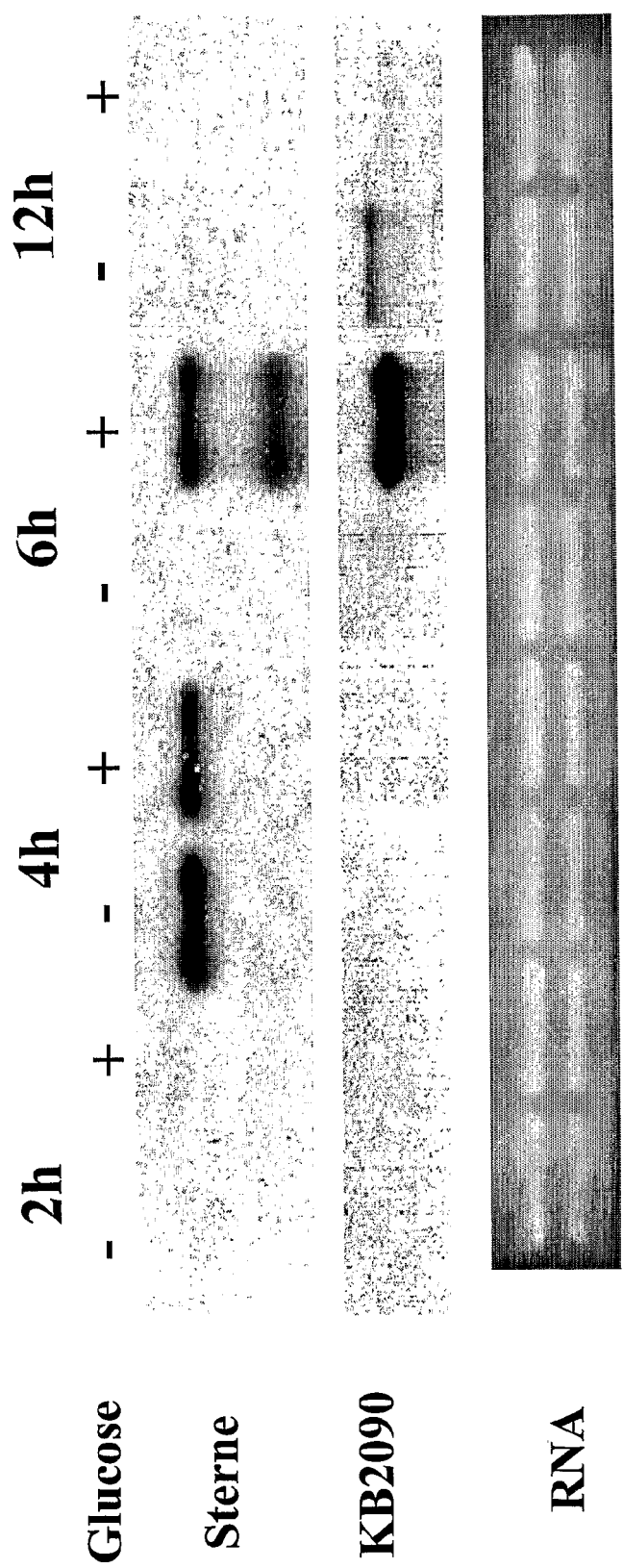
FIG. 20 is a digital image of a Northern blot analysis of cidAB transcription in *Bacillus anthracis*. Total cellular RNA samples from wild type (Sterne) and a cidR mutant (KB2090) cultured in either NZY broth or NZY broth with 35 mM glucose were isolated at various times post-inoculum. Five micrograms of each RNA sample were separated in a 1% (wt/vol) agarose-formaldehyde gel, transferred to a nylon membrane, and hybridized to a cidB-specific DIG-labeled probe. Expression of cidAB is most abundant at 4 hours of growth in both wild type (Sterne) and cidR deletion mutants. Expression is induced by glucose at 6 hours of growth, demonstrating that glucose induces cidAB expression in a cidR independent manner. The lower panel demonstrates that equivalent amounts of RNA were used in each amplification reaction. Similar results were observed using a cidA-specific probe demonstrating that cidA and cidB are cotranscribed.
Figure 21:
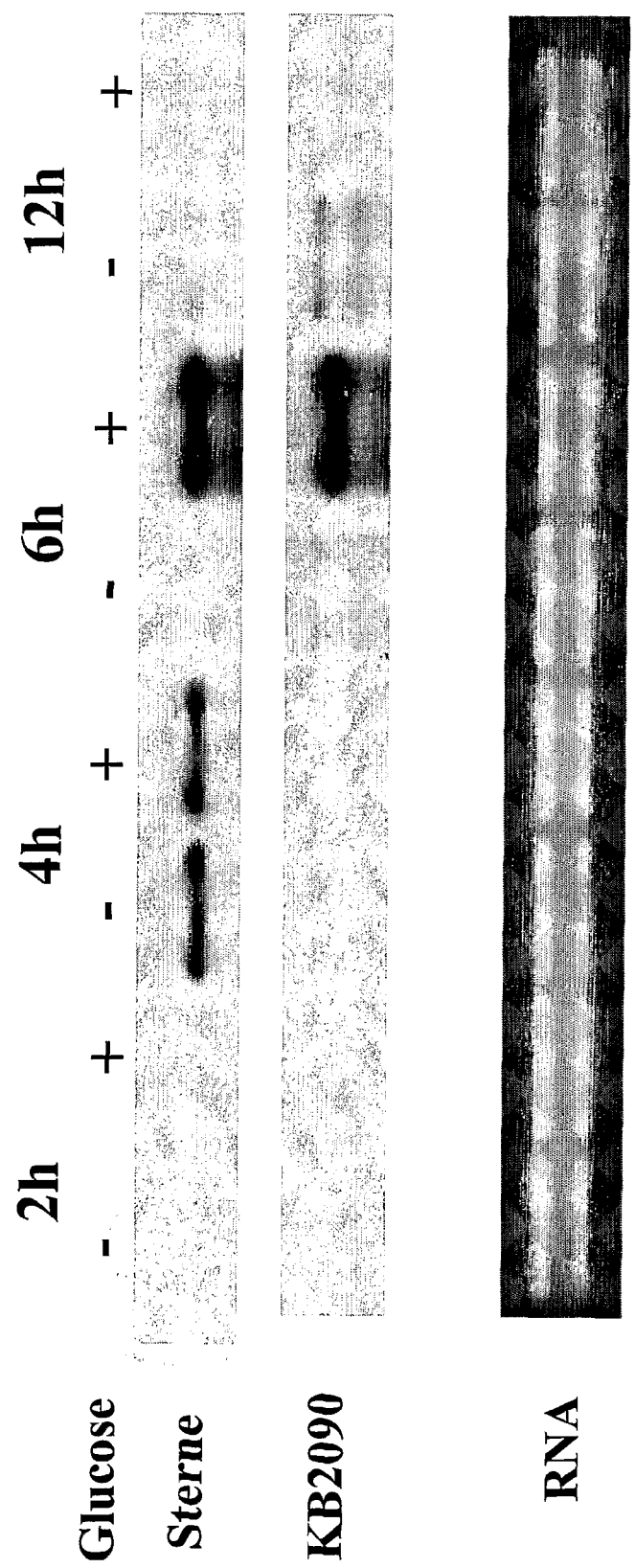
FIG. 21 is a digital image of a Northern blot analysis of lrgAB transcription in *Bacillus anthracis*. Total cellular RNA samples from wild type (Sterne) and a cidR mutant (KB2090) cultured in either NZY broth or NZY broth with 35 mM glucose were isolated at various times post-inoculum. Five micrograms of each RNA sample were separated in a 1% (wt/vol) agarose-formaldehyde gel, transferred to a nylon membrane, and hybridized to a lrgB-specific DIG-labeled probe. Expression of lrgAB is most abundant at 2 to 4 hours of growth in wild type (Sterne). Expression of lrgAB is suppressed in the cidR mutant at 2 but not 4 hours of growth in the absence of glucose. The lower panel demonstrates that equivalent amounts of RNA were used in each amplification reaction. Similar results were observed using a lrgA-specific probe demonstrating that lrgA and lrgB are cotranscribed.

Results:

Northern blot analysis. Previous studies of cidABC and lrgAB transcription in *S. aureus* indicated that these operons are induced by growth in the presence of excess glucose. To examine the expression of the cidAB and lrgAB operons in *B. anthracis*, a Northern blot analysis was performed to analyze cidAB expression during growth in *B. anthracis* wild type and cidR mutant at various time points. As shown in FIG. 20, expression of the cidAB operon is most abundant at 4 hours of growth. Whereas lrgAB transcription is most abundant at 2 and 4 hours of growth (FIG. 21). Transcription of cidAB is induced with glucose (35 mM) at 6 hours in both wild type (Sterne strain) and cidR mutant (FIG. 20), indicating the presence of cidR-independent transcriptional regulation of cidAB. Transcription of lrgAB in the cidR mutant is suppressed at 2 hours growth, but not suppressed at 4 hours in the absence of glucose (FIG. 21). These results indicate that the cidAB genes as well as lrgAB genes are co-transcribed and regulated by CidR and glucose.

Figure 22:
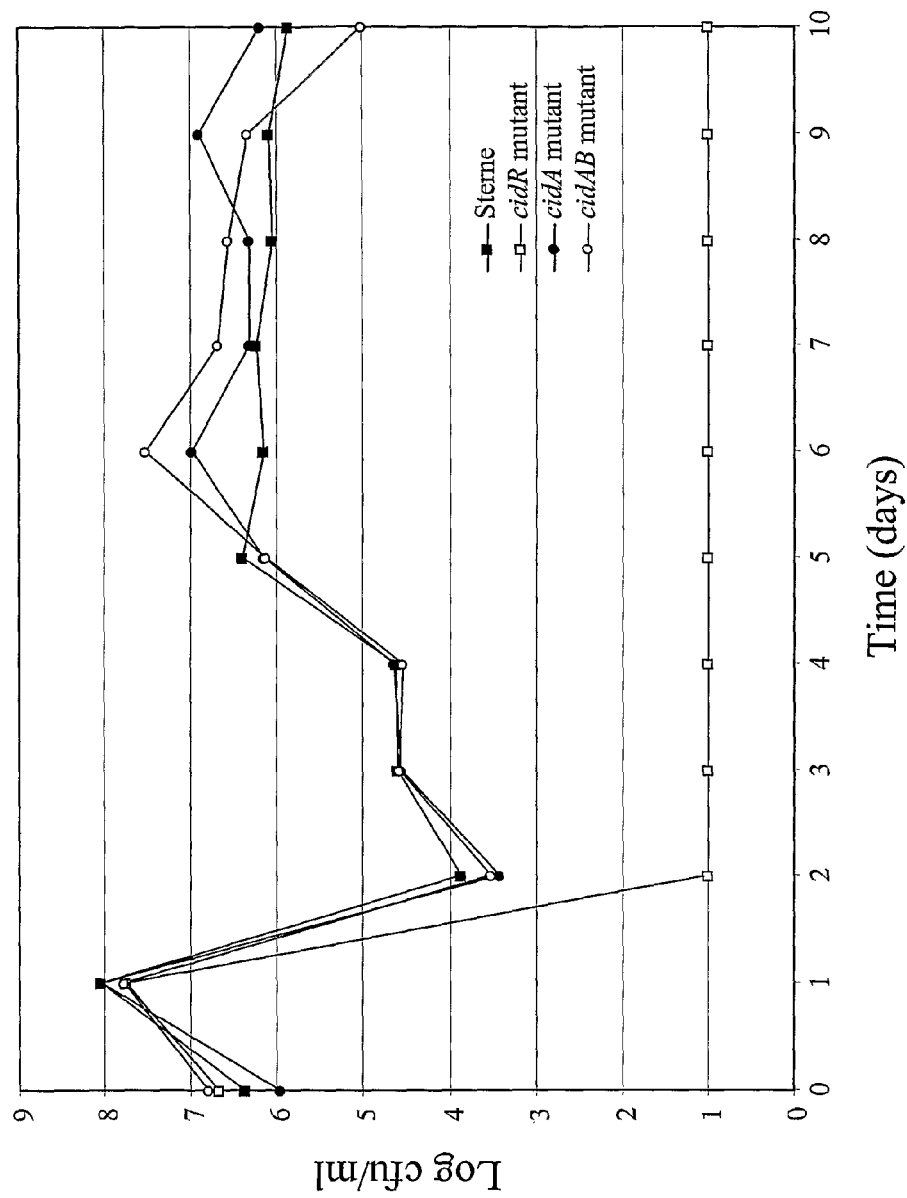
FIG. 22 is a line graph illustrating long term survival of wild type *Bacillus anthracis* (Sterne), and cidA, cidAB, and cidR mutants. The cidR mutant died within 48 hours in the absence of glucose, and within 24 hours in the presence of high glucose.

Long-term survival assay. The effect of *B. anthracis* mutants on long term viability was assessed by comparing *B. anthracis* wild type (Sterne) and cidR, cidA, cidAB mutants. As shown in FIG. 22, the cidR mutant died within 48 hours in the absence of glucose, and within 24 hours in the presence of glucose. Thus, the *B. anthracis* cidR gene, similar to the cidR gene of *S. aureus*, affects long-term survival in stationary phase.

Figure 23:
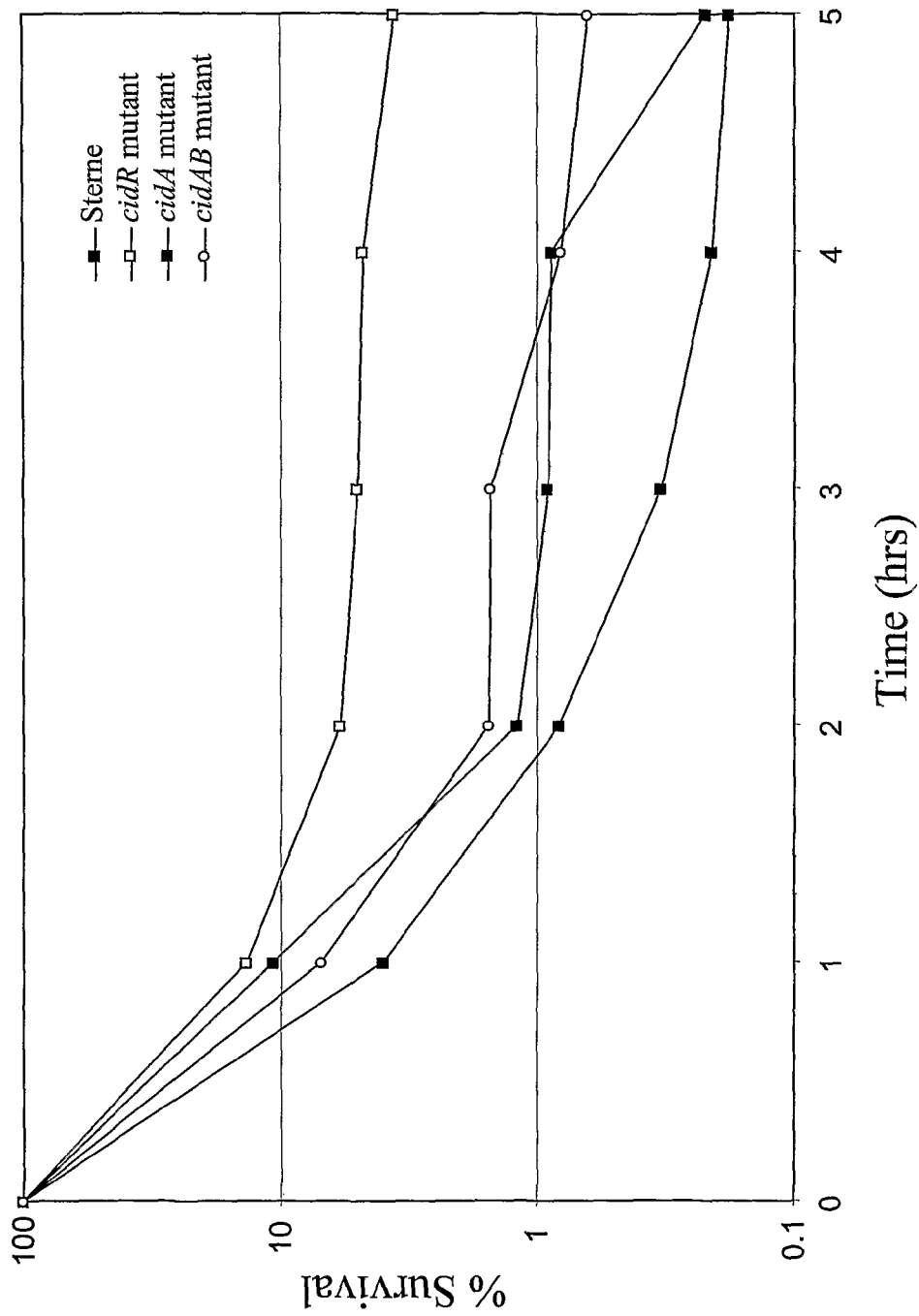
FIG. 23 is a line graph illustrating a comparison of antibiotic sensitivity in wild type *Bacillus anthracis* (Sterne), and cidA, cidAB, and cidr mutants. The cidR mutants showed substantially increased resistance to the antibiotic vancomycin as compared to wild type *Bacillus anthracis*.

Effects of cidR on antibiotic tolerance. Mutation in the lrgAB operon enhanced penicillin-induced killing in exponentially growing cultures of *S. aureus*, whereas mutation in cidA decreased killing by penicillin, vancomycin and rifampicin. Therefore, the effect of cidR mutation on antibiotic-induced killing in *B. anthracis* was assessed by comparing the viability of 2 hour culture of wild type *B. anthracis* (Sterne) and a cidR mutant after exposure to vancomycin (10 μg/ml). As shown in FIG. 23, the cidR mutant (and the cidA mutant to a lesser extent) demonstrated increased tolerance to the killing effects of vancomycin.

Example 6

Identification of Agents that Induce cidABC

A reporter construct was produced (FIG. 24) that incorporates an optically detectable reporter operably linked to the transcription regulatory region of the cidABC operon. Approximately 1 kb of the *Staph. aureus* cidABC promoter (SEQ ID NO: 19), flanked by EcoRI and XbaI restriction sites, was ligated adjacent to a promoterless gfp gene. The polynucleotide sequence encoding GFP is provided in SEQ ID NO: 20. This construct exhibits glucose-inducible GFP expression, and is useful for the identification of agents that induce expression of the cidABC operon.

This disclosure provides mutant bacteria having a reduced capacity to produce acetate, which mutants are defective in a cidABC operon, gene, or homolog thereof. The disclosure further provides methods of exploiting such mutant bacteria to produce high yield cultures, as well as to produce high levels of product from such cultures. Additionally, this disclosure provides methods for identifying agents that increase the sensitivity of bacteria to the killing effects of antibiotics. Although the invention has been described in connection with specific preferred embodiments, it will be understood that the invention as claimed should not be unduly limited to such specific embodiments. It will be apparent that the precise details of the methods described may be varied or modified without departing from the spirit of the described invention, and without undue experimentation. We claim all such modifications, equivalents, and variations that fall within the scope and spirit of the claims below.

The invention claimed is:
1. An isolated bacterial cell comprising an inactivating mutation in a *Staphylococcus aureus* cidC gene encoding the amino acid sequence set forth as SEQ ID NO: 2, which mutation measurably reduces acetate production by the cell when the cell is grown in medium comprising a metabolizable carbon source.

2. The isolated bacterial cell of claim 1, wherein the mutation measurably reduces acetate production by the cell, in comparison to an isogenic cell not comprising the mutation, when grown in medium comprising glucose.

3. The isolated bacterial cell of claim 1, wherein the mutation in a cidC gene is a knockout mutation.

4. A method for producing a polypeptide, comprising:
culturing the isolated bacterial cell of claim 1, and
isolating the polypeptide from the culture medium;
wherein the mutant bacterial cell further comprises a nucleic acid encoding the polypeptide.

5. A method for increasing yield in a bacterial cell culture, wherein increased yield is measured as an increase in bacterial biomass, an increase in production of a product, an increase in turbidity, an increase in optical density, or a combination of two or more thereof, comprising culturing the isolated bacterial cell of claim 1, wherein the mutation measurably reduces acetate production by the bacterial cell in comparison to an isogenic cell not having the mutation, and wherein the reduced acetate production results in increased yield.

6. An isolated bacterial cell comprising an inactivating mutation in a gene encoding a *Staphylococcus* pyruvate oxidase polypeptide, wherein the pyruvate oxidase has at least 95% sequence identity with the amino acid sequence set forth as SEQ ID NO: 2, which inactivating mutation measurably reduces acetate production by the cell when the cell is grown in culture medium comprising a metabolizable carbon source.

7. The isolated bacterial cell of claim 6, wherein the mutation measurably reduces acetate production by the cell, in comparison to an isogenic cell not comprising the inactivating mutation, when grown in medium comprising glucose.

8. The isolated bacterial cell of claim 6, wherein the inactivating mutation is a knockout mutation.

9. A method for producing a polypeptide, comprising:
cultivating the isolated bacterial cell of claim 6 in a culture medium; and
isolating the polypeptide from the culture medium;
wherein the isolated bacterial cell further comprises a nucleic acid encoding the polypeptide.

10. A method for increasing yield in a bacterial cell culture, wherein increased yield is measured as an increase in bacterial biomass, an increase in production of a product, an increase in turbidity, an increase in optical density, or a combination of two or more thereof, the method comprising culturing the isolated bacterial cell of claim 6; wherein the inactivating mutation measurably reduces acetate production by the bacterial cell in comparison to an isogenic cell not having the inactivating mutation, and wherein the reduced acetate production results in increased yield.

11. An isolated bacterial cell comprising an inactivating mutation in a gene encoding a *Staphylococcus* pyruvate oxidase polypeptide, wherein the pyruvate oxidase has at least 98% sequence identity with the amino acid sequence set forth as SEQ ID NO: 2, which inactivating mutation measurably reduces acetate production by the cell when the cell is grown in culture medium comprising a metabolizable carbon source.

12. The isolated bacterial cell of claim 11, wherein the inactivating mutation measurably reduces acetate production by the cell, in comparison to an isogenic cell not comprising the inactivating mutation, when grown in medium comprising glucose.

13. The isolated bacterial cell of claim 11, wherein the inactivating mutation is a knockout mutation.

14. A method for producing a polypeptide, comprising:
cultivating the isolated bacterial cell of claim 11 in a culture medium; and
isolating the polypeptide from the culture medium,
wherein the isolated bacterial cell further comprises a nucleic acid encoding the polypeptide.

15. A method for increasing yield in a bacterial cell culture, wherein increased yield is measured as an increase in bacterial biomass, an increase in production of a product, an increase in turbidity, an increase in optical density, or a combination of two or more thereof, the method comprising culturing the isolated bacterial cell of claim 11; wherein the inactivating mutation measurably reduces acetate production by the bacterial cell in comparison to an isogenic cell not having the inactivating mutation, and wherein the reduced acetate production results in increased yield.

* * * * *